(12) United States Patent
Liu et al.

(10) Patent No.: US 10,208,047 B2
(45) Date of Patent: Feb. 19, 2019

(54) TERTIARY ALCOHOL IMIDAZOPYRAZINE BTK INHIBITORS

(71) Applicants: Jian Liu, Edison, NJ (US); Joseph A. Kozlowski, Princeton, NJ (US); Brian M. Andresen, Sharon, MA (US); Sobhana Babu Boga, Scotch Plains, NJ (US); Xiaolei Gao, Bridgewater, NJ (US); Deodial Guy Guiadeen, Chesterfield, NJ (US); Jiaqiang Cai, Shanghai (CN); Shilan Liu, Shanghai (CN); Dahai Wang, Shanghai (CN); Hao Wu, Shanghai (CN); Chundao Yang, Shanghai (CN)

(72) Inventors: Jian Liu, Edison, NJ (US); Joseph A. Kozlowski, Princeton, NJ (US); Brian M. Andresen, Sharon, MA (US); Sobhana Babu Boga, Scotch Plains, NJ (US); Xiaolei Gao, Bridgewater, NJ (US); Deodial Guy Guiadeen, Chesterfield, NJ (US); Jiaqiang Cai, Shanghai (CN); Shilan Liu, Shanghai (CN); Dahai Wang, Shanghai (CN); Hao Wu, Shanghai (CN); Chundao Yang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/538,910

(22) PCT Filed: Dec. 17, 2015

(86) PCT No.: PCT/US2015/066233
§ 371 (c)(1),
(2) Date: Jun. 22, 2017

(87) PCT Pub. No.: WO2016/109222
PCT Pub. Date: Jul. 7, 2016

(65) Prior Publication Data
US 2017/0342076 A1    Nov. 30, 2017

(30) Foreign Application Priority Data

Dec. 31, 2014 (WO) ................ PCT/CN2014/095764

(51) Int. Cl.
| | | |
|---|---|---|
| *C07D 487/04* | (2006.01) | |
| *A61K 31/4985* | (2006.01) | |
| *A61K 45/06* | (2006.01) | |

(52) U.S. Cl.
CPC ........ *C07D 487/04* (2013.01); *A61K 31/4985* (2013.01); *A61K 45/06* (2013.01)

(58) Field of Classification Search
CPC .................................................. C07D 487/04
See application file for complete search history.

(56) References Cited

U.S. PATENT DOCUMENTS

| | | |
|---|---|---|
| 8,673,925 B1 | 3/2014 | Goldstein |
| 2009/0286768 A1 | 11/2009 | Crew et al. |
| 2014/0336206 A1 | 11/2014 | Honigberg et al. |

FOREIGN PATENT DOCUMENTS

| | | |
|---|---|---|
| WO | WO2005037836 A2 | 4/2005 |
| WO | WO2007075554 | 7/2007 |
| WO | WO2009143051 | 11/2009 |
| WO | WO2010126960 A1 | 11/2010 |
| WO | WO2013010380 A1 | 1/2013 |
| WO | WO2013010868 | 1/2013 |

OTHER PUBLICATIONS

De Lucca et al. J.Med.Chem. vol. 59, pp. 7915-7935 (2016).*

* cited by examiner

*Primary Examiner* — Emily A Bernhardt
(74) *Attorney, Agent, or Firm* — Matthew A. Leff; Laura M. Ginkel

(57) ABSTRACT

The present invention provides Bruton's Tyrosine Kinase (Btk) inhibitor compounds according to Formula I, or pharmaceutically acceptable salts thereof, Formula I or to pharmaceutical compositions comprising these compounds and to their use in therapy. In particular, the present invention relates to the use of Btk inhibitor compounds of Formula I in the treatment of Btk mediated disorders.

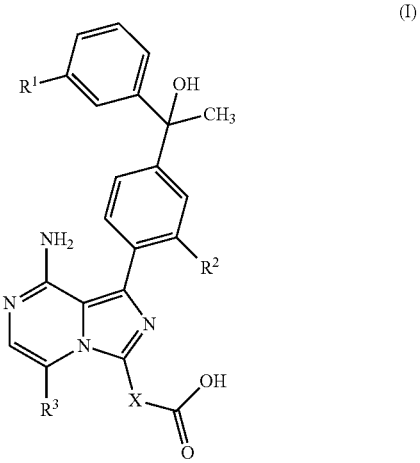

(I)

8 Claims, No Drawings
Specification includes a Sequence Listing.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15
```

TERTIARY ALCOHOL IMIDAZOPYRAZINE BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll-like receptor signaling was suggested.

Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors, e.g. Imidazo[1,5-f][1,2,4]triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoiesis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

Definitions

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", "alkylene", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms (1-6C)alkyl or from 1 to 3 carbon atoms (1-3C)alkyl. In one embodiment, an alkyl group is linear.

In another embodiment, an alkyl group is branched. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl.

"Alkoxy" refers to an alkyl-O— group represented by a linear or branched alkyl group of indicated number of carbon atoms attached through an oxygen bridge; for example "(1-3C)Alkoxy" includes —OCH$_3$, —OCH$_2$CH$_3$, —OCH(CH$_3$)$_2$, and the like.

Unless otherwise specifically noted as only "unsubstituted" or only "substituted", alkyl groups are unsubstituted or substituted with 1 to 3 substituents on each carbon atom.

The term "amount effective" or "effective amount" as used herein, refers to an amount of the compound of Formula I and/or an additional therapeutic agent, or a composition thereof, that is effective in producing the desired therapeutic, ameliorative, inhibitory or preventative effect when administered to a subject suffering from a BTK-mediated disease or disorder. In the combination therapies of the present invention, an effective amount can refer to each individual agent or to the combination as a whole, wherein the amounts of all agents administered are together effective, but wherein the component agent of the combination may not be present individually in an effective amount.

The term "cycloalkyl," as used herein, refers to a saturated mono- or multicyclic ring system containing up to 10 ring carbon atoms, and no heteroatom. In a like manner the term "(C$_{3-6}$) cycloalkyl" or (3-6C)cycloalkyl" refers to a saturated ring having from 3 to 6 ring carbon atoms. Non-limiting examples of monocyclic cycloalkyls include cyclopropyl, cyclobutyl, cyclopentyl, and cyclohexyl. In one embodiment, the cycloalkyl is cyclopropyl.

The term "heterocycloalkyl", as used herein, refers to a monocyclic ring having a 5- or 6-membered saturated ring system having 1 or 2 heteroatoms selected from N and/or O such that the heterocycloalkyl may be linked through a carbon or nitrogen atom. The heterocycloalkyl may be non-limiting examples of heterocycloalkyls include tetrahydrofuran, tetrahydropyran and piperidine. Additionally, heterocycloalkyl may refer to a multicyclic ring system having up to 10 carbon atoms with 1 or 2 heteroatoms selected from N and/or O.

The multicyclic ring system of the cycloalkyl and heterocycloalkyl groups may be composed of two or more rings that may be joined together to form a bridged ring system. Non-limiting examples of bridged groups include C$_6$-C$_9$ bridged cycloalkyls such as, for example, the following:

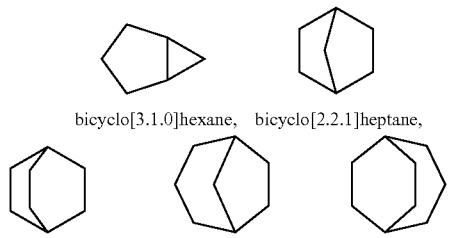

bicyclo[3.1.0]hexane, bicyclo[2.2.1]heptane, bicyclo[2.2.2]octane, bicyclo[3.2.1]octane, bicyclo[3.2.2]nonane, and -continued

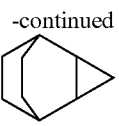

tricyclo[3.2.2.0$^{2,4}$]nonanyl, or any of these bridged groups substituted with 1 or 2 heteroatoms selected from N or O.

The term "halogen", as used herein, refers to fluorine, chlorine, bromine or iodine. Fluorine, chlorine or bromine being preferred halogens; fluorine being more preferred.

The term "C$_0$" as employed in expressions such as "(C$_{0-6}$)alkylene" means a direct covalent bond; or when employed in expressions such as "(C$_{0-6}$)alkyl" means hydrogen. Similarly, when an integer defining the presence of a certain number of atoms in a group is equal to zero, it means that the atoms adjacent thereto are connected directly by a bond; for example, in the structure

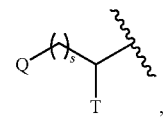

wherein s is an integer equal to zero, 1 or 2, the structure is

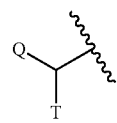

when s is zero; or it means that the indicated atom is absent; for example —S(O)$_0$— means —S—.

Unless expressly stated to the contrary, all ranges cited herein are inclusive. For example, a heterocycloalkyl described as containing from "1 to 4 heteroatoms" means the heterocycloalkyl can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)$_2$ can be

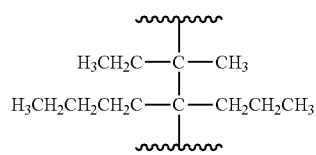

As used herein, the term "$X_a$-$X_b$", shall have the same meaning as the term "$X_{a-b}$" or "(a-bX)", wherein X is any atom and a and b are any integers. For example, "$C_1$-$C_4$" shall have the same meaning as "$C_{1-4}$" or "(1-4C)". Additionally, when referring to a functional group generically, "$A^x$" shall have the same meaning, and be interchangeable with, "AX", wherein "A" is any atom and "x" or "X" are any integer. For example, "$R^1$" shall have the same meaning, and be interchangeable with, "R1".

In the above definitions with multifunctional groups, the attachment point is at the last group. For example, the term $(C_{1-3})$alkoxycarbonyl refers to, e.g.

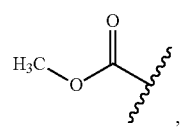

and the term $(C_{1-4})$alkylcarbonyloxy refers to, e.g.

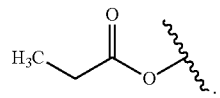

The term "oxo" as used herein, refers to an oxygen atom that is bonded to the compound having Formula I with a double bond.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "substituted", as used herein, means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that a compound may or may not be substituted with the specified groups, radicals or moieties.

A "subject" is a human or non-human mammal. In one embodiment, a subject is a human. In another embodiment, the subject is a chimpanzee.

In the above definitions with multifunctional groups, the attachment point is at the last group, unless otherwise specified on the substituent group by a dash. A dash on the substituent group would then represent the point of attachment.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides Btk inhibitor compounds according to Formula I or pharmaceutically acceptable salts thereof Formula I

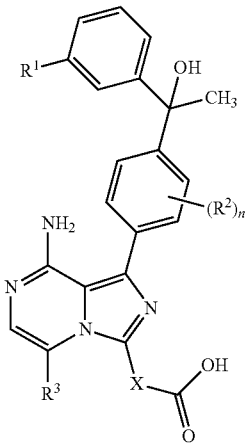

wherein:

n is 0, 1 or 2;

$R^1$ is (1-3C)alkyl, optionally substituted with one, two or three halogen;

$R_2$ is independently selected from the group consisting of methoxy, ethoxy, halogen, and hydroxyl;

$R_3$ is hydrogen, halogen or C(1-3) alkyl;

X is selected from the group consisting of:
  a) cycloalkyl; and
  b) heterocycloalkyl;

each optionally substituted with one to four $R^4$,
  wherein $R^4$ is hydrogen, oxo, fluoro or (1-6C)alkyl.

In another aspect the invention relates to the compound having Formula I, wherein X is selected from the group consisting of:
  a) cyclopropyl;
  b) cyclopentyl;
  c) cyclohexyl;
  d) bicyclo[2.2.2]octanyl;
  e) bicyclo[3.2.1]octanyl;
  f) bicyclo[2.2.1]heptanyl;
  g) bicyclo[3.2.2]nonanyl;
  h) bicyclo[3.1.0]hexanyl;
  i) tricyclo[3.2.2.0$^{2,4}$]nonanyl; and
  j) tetrahydropyranyl.

The present invention also provides Btk inhibitor compounds according to Formula Ia or pharmaceutically acceptable salts thereof Formula Ia

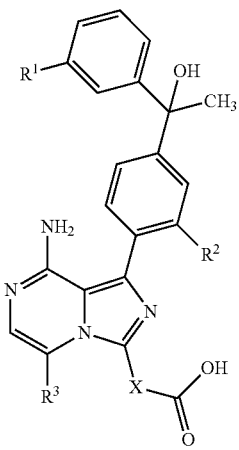

wherein:
R¹ is (1-3C)alkyl, optionally substituted with one, two or three halogen;
R² is hydrogen or (1-3C)alkoxy;
R³ is hydrogen or halogen;
X is selected from the group consisting of:
  a) cycloalkyl; and
  b) heterocycloalkyl;
each optionally substituted with one to four R⁴,
  wherein R⁴ is hydrogen, oxo, fluoro or (1-6C)alkyl.
In one aspect the invention relates to the compound having Formula Ia, wherein
X is selected from the group consisting of:
  a) cyclopropyl;
  b) cyclopentyl;
  c) cyclohexyl;
  d) bicyclo[2.2.2]octanyl;
  e) bicyclo[3.2.1]octanyl;
  f) bicyclo[2.2.1]heptanyl;
  g) bicyclo[3.2.2]nonanyl;
  h) bicyclo[3.1.0]hexanyl;
  i) tricyclo[3.2.2.0$^{2,4}$]nonanyl; and
  j) tetrahydropyranyl.
In another aspect the invention relates to a compound having Formula Ib Formula Ib

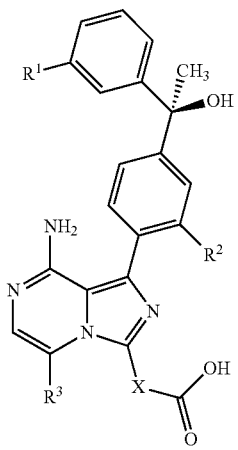

or a pharmaceutically acceptable salt thereof.

In another aspect the invention relates to a compound having Formula Ic

Formula Ic

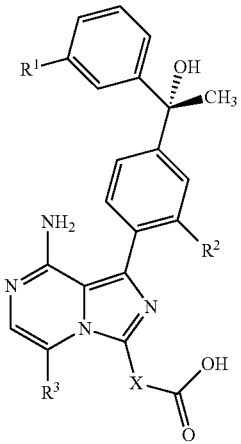

or a pharmaceutically acceptable salt thereof.

In another aspect the invention relates to the compound having Formula I, Ia, Ib and Ic, wherein R¹ is methyl, difluoromethyl or trifluoromethyl.

In yet another aspect the invention relates to the compound having Formula I, Ia, Ib, and Ic, wherein R² is ethoxy.

In a further aspect the invention relates to the compound having Formula I, Ia, Ib, and Ic, wherein R³ is fluoro or chloro.

The invention also relates to those compounds wherein all specific definitions for R¹, R², R³, R⁴ and X, and all substituent groups in the various aspects of the inventions defined hereinabove, occur in any combination within the definition of the Btk inhibitor compounds of Formula I or pharmaceutically acceptable salts thereof.

Non-limiting examples of the compounds of the present invention include:
(R)-4-(8-amino-1-(4-(1-hydroxy-1-(3-(trifluoromethyl)phenyl)ethyl)phenyl)imidazo[1,5-a]pyrazin-3-yl)-1,4-dimethylcyclohexanecarboxylic acid;
4-[8-amino-1-(4-{(1S)-1-hydroxy-1-[3-(trifluoromethyl)phenyl]ethyl}phenyl)imidazo[1,5-a]pyrazin-3-yl]bicyclo[2.2.2]octane-1-carboxylic acid;
4-[8-amino-1-(4-{(1R)-1-hydroxy-1-[3-(trifluoromethyl)phenyl]ethyl}phenyl)imidazo[1,5-a]pyrazin-3-yl]bicyclo[2.2.2]octane-1-carboxylic acid;
(1S,3S)-3-[8-amino-1-(4-{(1S)-1-hydroxy-1-[3 (trifluoromethyl)phenyl]ethyl}phenyl)imidazo[1,5-a]pyrazin-3-yl]-1-(1-methylethyl)cyclopentanecarboxylic acid;
(1S,3S)-3-[8-amino-1-(4-{(1R)-1-hydroxy-1-[3-(trifluoromethyl)phenyl]ethyl}phenyl)imidazo[1,5-a]pyrazin-3-yl]-1-(1-methylethyl)cyclopentanecarboxylic acid;
4-[8-amino-1-(4-{(1R)-1-hydroxy-1-[3-(trifluoromethyl)phenyl]ethyl}phenyl)imidazo[1,5-a]pyrazin-3-yl]-2,5-dioxobicyclo[2.2.2]octane-1-carboxylic acid;
1-[8-amino-1-(4-{(1R)-1-hydroxy-1-[3-(trifluoromethyl)phenyl]ethyl}phenyl)imidazo[1,5-a]pyrazin-3-yl]cyclopropanecarboxylic acid;
4-[8-amino-1-(4-{(1R)-1-hydroxy-1-[3-(trifluoromethyl)phenyl]ethyl}phenyl)imidazo[1,5-a]pyrazin-3-yl]bicyclo[2.2.1]heptane-1-carboxylic acid;
5-[8-amino-1-(4-{(1R)-1-hydroxy-1-[3-(trifluoromethyl)phenyl]ethyl}phenyl)imidazo[1,5-a]pyrazin-3-yl]bicyclo[3.2.2]nonane-1-carboxylic acid;

4-[8-amino-1-(4-{(1R)-1-hydroxy-1-[3-(trifluoromethyl)phenyl]ethyl}phenyl)imidazo[1,5-a]pyrazin-3-yl]tetrahydro-2H-pyran-4-carboxylic acid;

(1S,3R)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;

4-[8-amino-1-(4-{(1R)-1-hydroxy-1-[3-(trifluoromethyl)phenyl]ethyl}phenyl)imidazo[1,5-a]pyrazin-3-yl]-2,2,5,5-tetrafluorobicyclo[2.2.2]octane-1-carboxylic acid;

(1R,3S)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;

(1S,3R)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexanecarboxylic acid;

(1R,3S)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexanecarboxylic acid;

(1S,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;

(1R,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;

(1S,3R)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;

4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid;

4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid;

(1R,2R,5R)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexanecarboxylic acid;

5-[8-amino-1-(4-{(1R)-1-hydroxy-1-[3-(trifluoromethyl)phenyl]ethyl}phenyl)imidazo[1,5-a]pyrazin-3-yl]tricyclo[3.2.2.0~2,4~]nonane-1-carboxylic acid;

(1S,2S,5S)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexanecarboxylic acid;

(1S,3R)-3-[8-amino-5-fluoro-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;

(3-endo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid;

(3-exo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid;

(1S,3R)-3-[8-amino-1-(4-{(1R)-1-[3-(difluoromethyl)phenyl]-1-hydroxyethyl}phenyl)imidazo[1,5-a]pyrazin-3-yl]-1,2,2-trimethylcyclopentanecarboxylic acid;

(1S,3R)-3-[8-amino-1-(2-ethoxy-4-{(1S)-1-hydroxy-1-[3-(trifluoromethyl)phenyl]ethyl}phenyl)imidazo[1,5-a]pyrazin-3-yl]-1,2,2-trimethylcyclopentanecarboxylic acid;

(1S,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;

(1R,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;

(1S,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;

(1R,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;

4-[8-amino-1-(4-{(1R)-1-[3-(difluoromethyl)phenyl]-1-hydroxyethyl}phenyl)imidazo[1,5-a]pyrazin-3-yl]-1,4-dimethylcyclohexanecarboxylic acid;

(1S,3R)-3-[8-amino-1-(4-{(1R)-1-[3-(difluoromethyl)phenyl]-1-hydroxyethyl}phenyl)-5-fluoroimidazo[1,5-a]pyrazin-3-yl]-1,2,2-trimethylcyclopentanecarboxylic acid;

(1R,3R,5S,6S)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid; and (1R,3R,5S,6R)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid.

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The Btk inhibitor compounds of the present invention, which can be in the form of a free base, may be isolated from the reaction mixture in the form of a pharmaceutically acceptable salt.

The compounds of Formula I can form salts which are also within the scope of this invention. Reference to a compound of Formula I herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The Btk inhibitor compounds of the present invention may exist as amorphous forms or crystalline forms.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

Utilities

The compounds having Formula I and pharmaceutical compositions thereof can be used to treat or prevent a variety of conditions, diseases or disorders mediated by Bruton's Tyrosine kinase (Btk). Such Btk-mediated conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; and (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula I and salts thereof for use in therapy, and particularly in the treatment of disorders, diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In one embodiment, the present invention provides for the use of a compound of Formula I, or a pharmaceutically acceptable salt thereof for the manufacture of a medicament for the treatment of a Btk-mediated disorder.

In another embodiment, the present invention provides methods of regulating, modulating, or inhibiting Btk for the prevention and/or treatment of disorders related to unregulated or inappropriate Btk activity.

In a further embodiment, the present invention provides a method for treating a subject suffering from a disorder mediated by Btk, which comprises administering to said subject a compound of Formula I or a pharmaceutically acceptable salt thereof in an amount effective to treat the Btk-mediated disorder.

A further aspect of the invention resides in the use of a compound of Formula I or a pharmaceutically acceptable salt thereof for the manufacture of a medicament to be used for the treatment of chronic B cell disorders in which T cells play a prominent role.

Thus, the compounds according to the invention may be used in therapies to treat or prevent Bruton's Tyrosine Kinase (Btk) mediated diseases, conditions and disorders. Btk mediated diseases, conditions and disorders as used herein, mean any disease, condition or disorder in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplasic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergens, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Combination Therapy

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as etanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

The compound(s) of Formula I and the other pharmaceutically active agent(s) may be administered together or separately and, when administered separately this may occur simultaneously or sequentially in any order. The amounts of the compound(s) of Formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula I or a pharmaceutically acceptable salt thereof together with beta2-adrenoreceptor agonist and an anti-inflammatory corticosteroid. Preferably this combination is for treatment and/or prophylaxis of asthma, COPD or allergic rhinitis. The beta2-adrenoreceptor agonist and/or the anti-inflammatory corticosteroid can be as described above and/or as described in WO 03/030939 A1. Representative examples of such a "triple" combination are a compound of Formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpimase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PC132765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kifl4, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent, carrier or excipient represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Pharmaceutical Compositions

While it is possible that, for use in therapy, a compound of Formula I, as well as salts, solvates and physiological functional derivatives thereof, may be administered as the raw chemical, it is possible to present the active ingredient as a pharmaceutical composition. Accordingly, the invention further provides a pharmaceutical composition which comprises a compound of Formula I and salts, solvates and physiological functional derivatives thereof, and one or more pharmaceutically acceptable carriers, diluents, or excipients. The compounds of the Formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula I, or salts, solvates and physiological functional derivatives thereof, with one or more pharmaceutically acceptable carriers, diluents or excipients.

Routes of Administration

Pharmaceutical compositions of the present invention may be presented in unit dose forms containing a predetermined amount of active ingredient per unit dose. Such a unit may contain, for example, 5 μg to 1 μg, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration.

Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula I is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula I or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula I or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device(GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

Injectable Suspension (I.M.) mg/ml

| Compound of Formula I | 10 |
|---|---|
| Methylcellulose | 5.0 |
| Tween 80 | 0.5 |
| Benzyl alcohol | 9.0 |
| Benzalkonium chloride | 1.0 |
| Water for injection to a total volume of 1 ml | |

Tablet mg/Tablet

| Compound of Formula I | 25 |
|---|---|
| Microcrystalline Cellulose | 415 |
| Providone | 14.0 |
| Pregelatinized Starch | 43.5 |
| Magnesium Stearate | 2.5 |
| | 500 |

Capsule mg/Capsule

| Compound of Formula I | 25 |
|---|---|
| Lactose Powder | 573.5 |
| Magnesium Stearate | 1.5 |
| | 600 |

Aerosol Per Canister

| Compound of Formula I | 24 mg |
|---|---|
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate Btk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

General Synthesis

The compounds of the present invention can be prepared by methods well known in the art of organic chemistry. See, for example, J. March, '*Advanced Organic Chemistry*' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 3$^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

The compounds of Formula I can be prepared by the general synthetic route shown in the scheme below.

Scheme I

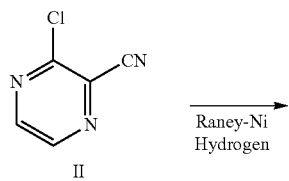

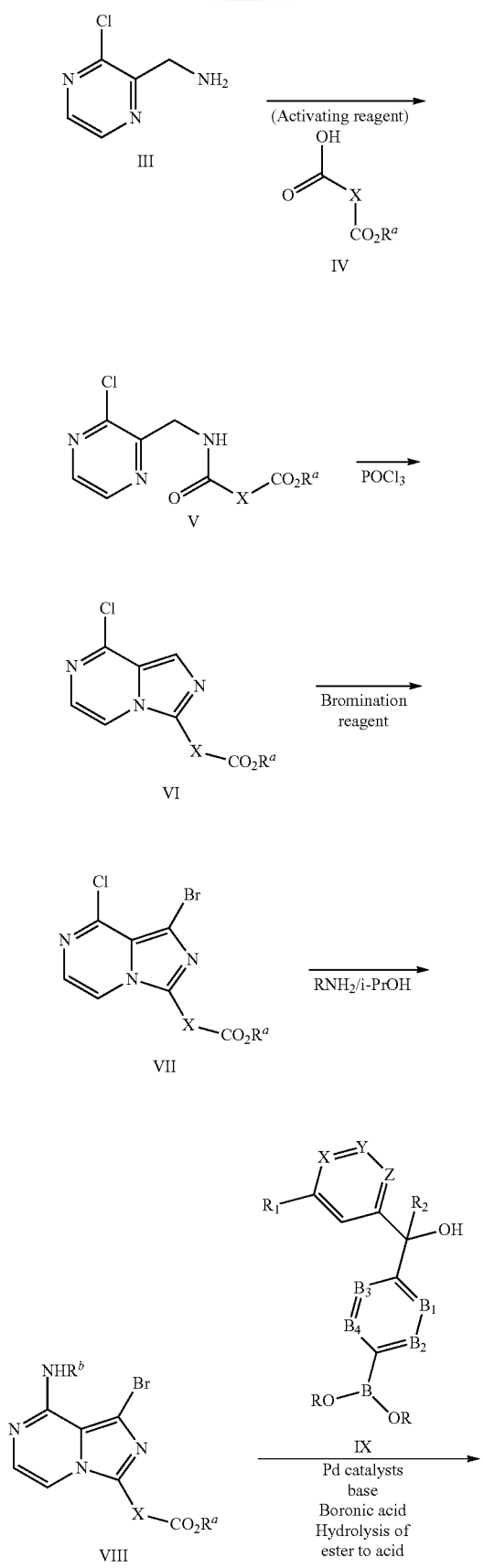

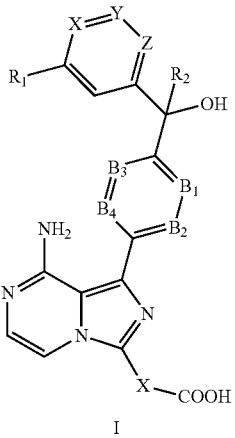

Reduction of 3-chloropyrazine-2-carbonitrile (II) can be accomplished by hydrogenation in the presence of a suitable catalyst system and solvent, for example Raney-Nickel ethanol to provide (3-chloropyrazin-2-yl)methanamine (III). This amine can then be reacted with the diacid monoester (IV). The reaction of IV can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (V). Cyclization chloropyrazine (V) can be performed using condensation reagents like phosphorusoxychloride under heating conditions to provide the 8-chloroimidazo[1,5-a]pyrazine derivatives VI. Subsequent bromination can be accomplished using bromine or N-bromosuccinimide in a suitable solvent like DCM or DMF at appropriate temperature to obtain compounds of formula VII. 8-Aminoimidazo[1,5-a]pyrazine derivatives (VIII) can be prepared from compounds VII using ammonia (gas) in isopropanol at elevated temperature in a pressure vessel (>4 atm) or with primary amine (such as dimethoxybenzylamine) under heating. Compounds of formula I can be prepared from compounds of formula VIII using an appropriate boronic acid or pinacol ester (IX), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water. Palladium catalysts and conditions to form either the pinacol esters or to couple the boronic acids or pinacol esters with the 1-bromoimidazo[1,5-a]pyrazin-8-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002. The ester usually is hydrolyzed during the Suzuki coupling with water as co-solvent, otherwise one additional step for the hydrolysis of ester under conventional basic or acid conditions. The diacid mono esters IV are commercially available or can be readily prepared using methods well known to the skilled organic chemist.

Several routes for the preparation of the biaryl tertiary alcohol boronic ester IX are shown in Scheme II. Route 1 use Weinreb amide X to react with the aromatic metallic reagent XI to provide ketone XII, which then reacts with alkyl lithium or Grinard reagent to provide intermediate XII.

The bromo in XII can be converted to boronic ester using palladium catalized conversion. The difference of Route 2 and Route 1 is that Route 2 utilizes the Weinreb amide XIV and metallic reagent XV for the first step. Route 3 apply the commercially available or readily prepared methal ketone XVIII to react with the aromatic metallic reagent XI to form the tertiary alcohol XV, in which the bromo was later converted to the boronic ester.

Scheme II

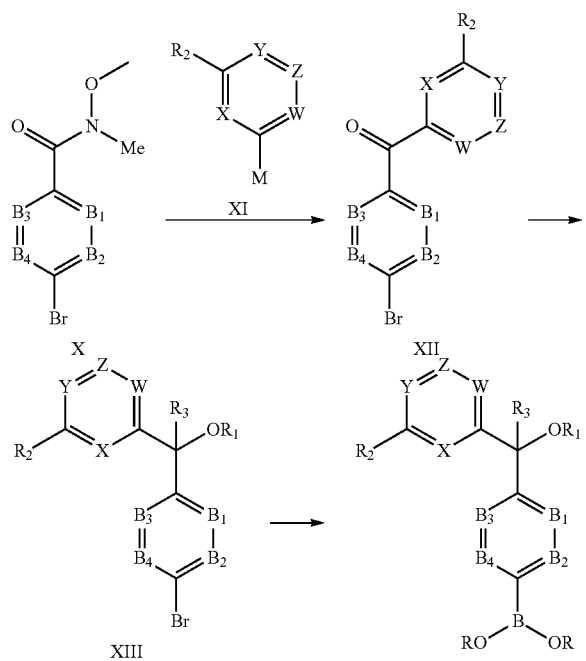

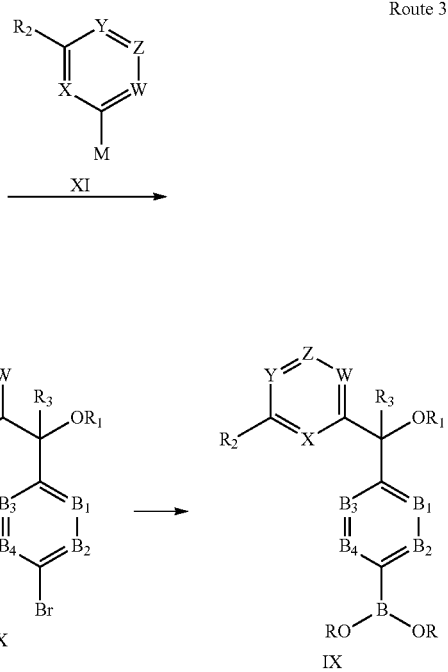

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da. and scanned with a step rate of 0.2 Da. and the capillary voltage was set to 5000 V. $N_2$ gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.

Method A: LC-MS

| Column | Ascentis Express C18, 100 × 3.0 mm, 2.7 μm |
| --- | --- |
| Mobile Phase | A: $H_2O$ (0.1% TFA) |
| | B: MeCN (0.05% TFA) |
| | Stop Time: 5.0 min |

| | Time (min) | B % |
| --- | --- | --- |
| | 0.00 | 10 |
| | 3.50 | 99 |
| | 4.99 | 99 |
| Gradient | 5.00 | 10 |

| Sample injection volume | 2 μl |
| --- | --- |
| Flow Rate | 1.00 ml/min |
| Wavelength | 220 nm |

Method B: LC-MS

| Column | Ascentis Express C18, 50 × 2.1 mm, 5 μm |
|---|---|
| Mobile Phase | A: H$_2$O (0.1% TFA)<br>B: MeCN (0.05% TFA)<br>Stop Time: 2.0 min |

| | Time (min) | B % |
|---|---|---|
| | 0 | 10 |
| | 0.8 | 99 |
| | 1.99 | 99 |
| Gradient | 2.00 | 10 |

| Sample injection volume | 2 μl |
|---|---|
| Flow Rate | 1.25 ml/min |
| Wavelength | 220 nm |
| Oven Temp. | 50° C. |
| MS polarity | ESI POS |

Method C:
Sample Info: Easy-Access Method: '1-Short_TFA_Pos'
Method Info: B222 Column Agilent SBC (3.0×50 mm, 1.8 m); Flow 1.0 mL/min; solvent A: H$_2$O-0.1% TFA; solvent B: MeCN-0.1% TFA;
GRADIENT TABLE: 0 min: 10% B, 0.3 min: 10% B, 1.5 min: 95% B, 2.70 min: 95% B, 2.76 min: 10% B
stop time 3.60 min, PostTime 0.70 min.
Method D:
Sample Info: Easy-Access Method: '1_Fast'
Method Info: A330 Column Agilent Zorbax SB-C18 (2.1×30 mm, 3.5 m); Flow 2.0 mL/min;
solvent A: H$_2$O-0.1% TFA;
solvent B: MeCN-0.1% TFA;
GRADIENT TABLE: 0.01 min: 10% B, 1.01 min: 95% B, 1.37 min: 95% B, 1.38 min: 10% B,
stop time 1.7 min, PostTime=OFF The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl
D Deuterated hydrogen
DMF N,N-Dimethylformamide
DCM Dichloromethane
EA Ethyl acetate
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide hydrochloride
4-DMAP 4-Dimethylaminopyridine
PyBOP O-Benzotriazole-1-yl-oxy-trispyrrolidinophosphoniumhexafluorophosphat
TBTU O-Benzotriazol-1-yl-N,N,N',N'-tetramethyluronium tetrafluoroborate
HBr Hydrogen bromide
HCl Hydrogen chloride
HOAc Acetic acid
POCl$_3$ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
CO$_2$ Carbondioxide
NaHCO$_3$ Sodium bicarbonate
K$_3$PO$_4$ Potassium phosphate
P(Cy)$_3$ Tricyclohexylphosphine
Pd(OAc)$_2$ Palladium(II) acetate
Na$_2$SO$_4$ Sodium sulfate
Na$_2$CO$_3$ Sodium carbonate
DAST Diethylaminosulfur trifluoride
Cs$_2$CO$_3$ Cesium carbonate
Et$_2$O Diethylether
Na$_2$S$_2$O$_3$ Sodium thiosulfate
Na$_2$S$_2$O$_4$ Sodium hydrosulfite
NaCNBH$_3$ Sodium cyanoborohydride
NH$_4$Cl Ammonium chloride
MgSO$_4$ Magnesium sulfate
LiOH Lithium hydroxide
IPA Isopropylamine
TFA Trifluoroacetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethylamine
CDI 1,1'-Carbonyl diimidazole
DMI 1,3-Dimethyl-2-imidazolidinone
NBS N-Bromosuccinimide
i-PrOH 2-Propanol
K$_2$CO$_3$ Potassium carbonate
Pd(dppf)Cl$_2$ 1,1'-Bis(diphenylphosphino)ferrocene palladium (II) chloride, complex with dichloromethane
Et$_3$N Triethylamine
2-BuOH 2-Butanol
LCMS Liquid Chromatography/Mass Spectrometry
MeCN Acetonitrile
NH$_3$ Ammonia
CD$_3$I Trideuteromethyl iodide
CD$_3$OD Tetradeuteromethanol
CH$_3$I Iodomethane
CBr$_4$ Carbon tetrabromide
Tris-HCl Tris(hydroxymethyl)aminomethane hydrochloride
MgCl$_2$ Magnesium chloride
NaN$_3$ Sodium azide
DTT Dithiothreitol
DMSO Dimethyl sulfoxide
IMAP Immobilized Metal Ion Affinity-Based Fluorescence Polarization
ATP Adenosine triphosphate
MnCl$_2$ Manganese(II) chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
Ret. Time Retention Time
RT (rt) Room Temperature
Aq Aqueous
EtOH Ethanol
MPLC Medium Pressure Liquid Chromatography Xantphos 4,5-Bis(diphenylphosphino)-9,9-dimethylxanthene
X-phos 2-Dicyclohexylphosphino-2',4',6'-triisopropylbiphenyl

INTERMEDIATES

Intermediate 1aE1, 1aE2, 1bE1 and 1bE2

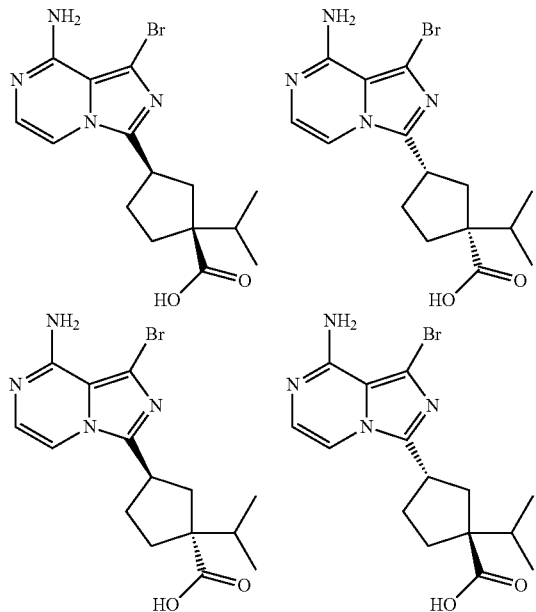

(1S, 3R) 3-(8-amino-1-bromoimidazo[1,5-a]pyrazin-3-yl)-1-isopropylcyclopentanecarboxylic acid (1R, 3S) 3-(8-amino-1-bromoimidazo[1,5-a]pyrazin-3-yl)-1-isopropylcyclopentanecarboxylic acid (1R, 3R) 3-(8-amino-1-bromoimidazo[1,5-a]pyrazin-3-yl)-1-isopropylcyclopentanecarboxylic acid (1S, 3S) 3-(8-amino-1-bromoimidazo[1,5-a]pyrazin-3-yl)-1-isopropylcyclopentanecarboxylic acid Step 1: dimethyl cyclopentane-1,3-dicarboxylate To a solution of 3-(methoxycarbonyl)cyclopentanecarboxylic acid (18 g, 104.6 mmol) in MeOH (200 mL) was added $H_2SO_4$ (30.8 g, 313.9 mmol). The mixture was stirred at 70° C. for 2 h. The solvent was concentrated and the residue was purified by column chromatography on silica gel eluted with PE/EA=4/1 to give dimethyl cyclopentane-1,3-dicarboxylate. $^1$H NMR (CDCl$_3$, 400 MHz) δ 1.85-2.01 (m, 4H), 2.04-2.12 (m, 1H), 2.18-2.26 (m, 1H), 2.69-2.87 (m, 2H), 3.66 (s, 6H) ppm.

Step 2: dimethyl 1-isopropylcyclopentane-1,3-dicarboxylate

To a solution of LDA (14.8 mL, 29.6 mmol) in THF (80 mL) and HMPT (19.2 g, 107.5 mmol) at −65° C. was added dropwise a solution of dimethyl cyclopentane-1,3-dicarboxylate (5 g, 26.9 mmol) in THF (20 mL). The mixture was stirred at −65° C. for 10 min, 2-iodopropane (9.1 g, 53.8 mmol) was then added dropwise and the resulting mixture was stirred at room temperature for 4 h. The reaction mixture was quenched with saturated NH$_4$Cl solution and extracted with EA. The organic layer was dried and concentrated, the residue was purified by column chromatography on silica gel eluted with PE/EA=10/1 to give dimethyl 1-isopropyl-cyclo pentane-1,3-dicarboxylate. $^1$H NMR (CDCl$_3$, 400 MHz) δ 0.78-0.95 (m, 6H), 1.47-1.79 (m, 2H), 1.82-2.00 (m, 3H), 2.11-2.30 (m, 1H), 2.35-2.52 (m, 1H), 2.69-2.85 (m, 1H), 3.59-3.70 (m, 6H) ppm.

Step 3: 3-isopropyl-3-(methoxycarbonyl)cyclopentanecarboxylic acid

To a solution of dimethyl 1-isopropylcyclopentane-1,3-dicarboxylate (5.4 g, 23.7 mmol) in THF/MeOH/H$_2$O (50 mL/50 mL/20 mL) was added LiOH.H$_2$O (3 g, 71.1 mmol). The mixture was stirred at room temperature for 4 h. The reaction mixture was diluted with water, acidified by 1 M HCl, and extracted with EA. The organic layer was dried and concentrated. The residue was used in next step directly.

Step 4: methyl 3-(((3-chloropyrazin-2-yl)methyl)carbamoyl)-1-isopropylcyclopentane carboxylate To a solution of 3-isopropyl-3-(methoxycarbonyl)cyclopentanecarboxylic acid (5.1 g, 23.8 mmol) in THF (130 mL) was added (3-chloropyrazin-2-yl)methanamine (6.4 g, 35.7 mmol), HATU (13.6 g, 35.7 mmol) and TEA (14.4 g, 143 mmol). The mixture was stirred at room temperature overnight. The reaction mixture was treated with EA and water, the organic layer was dried and concentrated. The residue was purified by column chromatography on silica gel eluted with PE/THF=10/1 to give methyl 3-(((3-chloropyrazin-2-yl)methyl)carbamoyl)-1-isopropylcyclopentanecarboxylate. $^1$H NMR (CDCl$_3$, 400 MHz) δ 0.89-0.94 (m, 6H), 1.62-1.82 (m, 2H), 1.91-2.29 (m, 4H), 2.43-2.55 (m, 1H), 2.77-2.93 (m, 1H), 3.70 (d, J=3.52 Hz, 3H), 4.65-4.78 (m, 2H), 8.33-8.39 (m, 1H), 8.45-8.52 (m, 1H) ppm.

Step 5: methyl 3-(8-chloroimidazo[1,5-a]pyrazin-3-yl)-1-isopropylcyclopentanecarboxylate To a solution of methyl 3-(((3-chloropyrazin-2-yl)methyl)carbamoyl)-1-isopropylcyclopentane carboxylate (2 g, 5.9 mmol) in MeCN (100 mL) was added PCl$_5$ (2.45 g, 11.8 mmol). The mixture was stirred at 65° C. for 2 h. The reaction solution was treated with DCM and aq. NaHCO$_3$. The organic layer was dried and concentrated. The residue was purified by column chromatography on silica gel eluted with DCM/THF=50/1 to give methyl 3-(8-chloroimidazo[1,5-a]pyrazin-3-yl)-1-isopropylcyclopentanecarboxylate. MS-ESI (m/z): 322 [M+1]$^+$ Step 6: methyl 3-(1-bromo-8-chloroimidazo[1,5-a]pyrazin-3-yl)-1-isopropylcyclopentane carboxylate To a solution of methyl 3-(8-chloroimidazo[1,5-a]pyrazin-3-yl)-1-isopropylcyclopentanecarboxylate (1.7 g, 5.3 mmol) in DMF (30 mL) was added a solution of NBS (1 g, 5.8 mmol) in DMF (10 mL). The mixture was stirred at room temperature for 1 h. The reaction mixture was treated with EA and water. The organic layer was dried and concentrated. The residue was purified by column chromatography on silica gel eluted with DCM/THF=50/1 to give methyl 3-(1-bromo-8-chloroimidazo[1,5-a]pyrazin-3-yl)-1-isopropylcyclopentanecarboxylate. MS-ESI (m/z): 402 [M+1]+

Step 7: methyl 3-(1-bromo-8-((2,4-dimethoxybenzyl)amino)imidazo[1,5-a]pyrazin-3-yl)-1-isopropyl cyclopentanecarboxylate To a solution of methyl 3-(1-bromo-8-chloroimidazo[1,5-a]pyrazin-3-yl)-1-isopropylcyclo pentanecarboxylate (2 g, 5 mmol) in DMF (40 mL) was added K$_2$CO$_3$ (1.38 g, 10 mmol) and (2,4-dimethoxyphenyl)methanamine (921 mg, 5.5 mmol). The mixture was stirred at 90° C. for 6 h. The reaction mixture was treated with EA and water. The organic layer was dried and concentrated. The residue was purified by column chromatography on silica gel eluted with PE/DCM/EA=1/1/0.2 to give methyl 3-(1-bromo-8-((2,4-dimethoxy benzyl)amino)imidazo[1,5-a]pyrazin-3-yl)-1-isopropylcyclopentanecarboxylate. $^1$H NMR (CDCl$_3$, 400 MHz) δ 0.74-0.93 (m, 6H), 1.10-1.28 (m, 1H), 1.52-1.64 (m, 1H), 1.73-1.83 (m, 1H), 1.97-2.10 (m, 3H), 2.33-2.47 (m, 1H), 3.15-3.28 (m, 1H), 3.55-3.69 (m, 3H), 3.73 (s, 3H), 3.81 (s, 3H), 4.59 (d, J=5.6 Hz, 2H), 6.34-6.47 (m, 2H), 6.59-6.68 (m, 1H), 6.94-7.03 (m, 2H), 7.16-7.23 (m, 1H) ppm.

Step 8: 3-(1-bromo-8-((2,4-dimethoxybenzyl)amino)imidazo[1,5-a]pyrazin-3-yl)-1-isopropyl cyclopentanecarboxylic acid To a solution of methyl 3-(1-bromo-8-((2,4-dimethoxybenzyl)amino)imidazo[1,5-a]pyrazin-3-yl)-1-isopropylcyclopentanecarboxylate (1.2 g, 2.26 mmol) in MeOH (40 mL) was added KOH (1.6 g, 29.4 mmol) and 18-Crown-6 (200 mg). The mixture was stirred at 80° C. overnight. Then the mixture was added THF/H$_2$O (20 mL/10 mL), and stirred at 80° C. for further 3 days. The reaction was neutralized with 2 M HCl and extracted with EA. The organic layer was dried and concentrated. The residue was purified by column chromatography on silica gel eluted with DCM/EA=2/1 to give 3-(1-bromo-8-((2,4-dimethoxybenzyl)amino)imidazo[1,5-a]pyrazin-3-yl)-1-isopropylcyclopentanecarboxylic acid. MS-ESI (m/z): 517 [M+1]+.

Step 9: 3-(8-amino-1-bromoimidazo[1,5-a]pyrazin-3-yl)-1-isopropylcyclopentanecarboxylic acid A solution of 3-(1-bromo-8-((2,4-dimethoxybenzyl)amino)imidazo[1,5-a]pyrazin-3-yl)-1-isopropylcyclopentanecarboxylic acid (1 g, 1.9 mmol) in TFA (6 mL) was heated to reflux for 2 h. The mixture was concentrated and the residue was purified by pre-HPLC to give cis-3-(8-amino-1-bromoimidazo[1,5-a]pyrazin-3-yl)-1-isopropylcyclopentanecarboxylic acid (350 mg), and trans-3-(8-amino-1-bromoimidazo[1,5-a]pyrazin-3-yl)-1-isopropylcyclopentanecarboxylic acid (300 mg), which were separated with SFC to give (1S,3R)-3-(8-amino-1-bromoimidazo[1,5-a]pyrazin-3-yl)-1-isopropylcyclopentanecarboxylic acid (100 mg), (1R,3S)-3-(8-amino-1-bromoimidazo[1,5-a]pyrazin-3-yl)-1-isopropylcyclopentanecarboxylic acid (90 mg), (1R,3R)-3-(8-amino-1-bromoimidazo[1,5-a]pyrazin-3-yl)-1-isopropylcyclopentanecarboxylic acid (90 mg) and (1S,3S)-3-(8-amino-1-bromoimidazo[1,5-a]pyrazin-3-yl)-1-isopropylcyclopentanecarboxylic acid (120 mg). SFC condition: For cis mixture: "Column: Chiralpak AD-H 250× 4.6 mm I.D., 5 um Mobile phase: ethanol (0.05% DEA) in CO$_2$ from 5% to 40% Flow rate: 2.35 mL/min Wavelength: 220 nm".

$^1$H NMR (CD$_3$OD, 400 MHz) δ 0.97 (dd, J=11.17, 6.90 Hz, 6H), 1.69-1.82 (m, 1H), 2.01-2.23 (m, 4H), 2.40-2.59 (m, 2H), 3.48-3.61 (m, 1H), 6.92 (d, J=6.0 Hz, 1H), 7.71 (d, J=6.0 Hz, 1H) ppm.

For trans mixture: "Column: Chiralpak AD-H 250×4.6 mm I.D., 5 um Mobile phase: ethanol (0.05% DEA) in CO$_2$ from 5% to 40% Flow rate: 2.35 mL/min Wavelength: 220 nm".

$^1$H NMR (CD$_3$OD, 400 MHz) δ 0.98 (dd, J=10.92, 6.90 Hz, 6H), 1.88-1.98 (m, 3H), 2.04-2.34 (m, 3H), 2.60-2.69 (m, 1H), 3.52-3.62 (m, 1H), 6.91 (d, J=6.0 Hz, 1H), 7.68 (d, J=6.0 Hz, 1H) ppm.

Intermediate 2

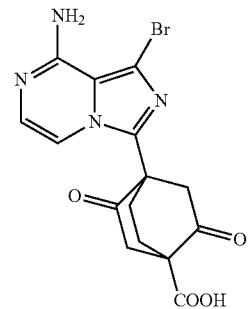 [SMILES: Nc1nccn2c(C34CCC(C(=O)O)(CC3=O)C(=O)C4)nc(Br)c12]

4-(8-Amino-1-bromo-imidazo[1,5-a]pyrazin-3-yl)-2,5-dioxo-bicyclo[2.2.2]octane-1-carboxylic acid Step 1: ethyl 4'-(((3-chloropyrazin-2-yl)methyl)carbamoyl)dispiro[[1,3]dioxolane-2,2'-bicyclo[2.2.2]octane-5',2"-[1,3]dioxolane]-1'-carboxylate A solution of Dispiro [1, 3-dioxolane-2, 2'-bicyclo [2.2.2] octane-5', 2"-[1, 3] dioxolane]-1', 4'-dicarboxylic acid (1 g, 2.92 mmol) in DCM (50 mL) was added (CClO)$_2$ (473 mg, 4.38 mmol) at 0° C., the mixture was stirred at 25° C. for 1 hour. The mixture was concentrated to afford Dispiro [1, 3-dioxolane-2, 2'-bicyclo [2.2.2] octane-5', 2"-[1, 3] dioxolane]-1', 4'-dicarboxylic acyl chloride. To a solution of Dispiro [1, 3-dioxolane-2, 2'-bicyclo [2.2.2] octane-5', 2"-[1, 3]dioxolane]-1', 4'-dicarboxylic acyl chloride in DCM (20 mL) was added (3-chloropyrazin-2-yl) methanamine (419.39 mg, 2.92 mmol) at 0° C., the mixture was stirred at 25° C. for 1 hour. H$_2$O (20 mL) was added to the mixture, the mixture was extracted by EA (50 mL). The organic layer was washed with H$_2$O (30 mL) and brine (30 mL), dried over Na$_2$SO$_4$, concentrated to afford the crude product, which was purified on silica gel chromatography with the eluent of PE:THF (5:1-1:1) to give the title compound as solid.

$^1$H NMR (400 MHz, CDCl$_3$) δ=8.42 (d, J=1.6 Hz, 1H), 8.29 (br. s., 1H), 7.89 (br. s., 1H), 7.24 (s, 1H), 5.27 (s, 1H), 4.77-4.55 (m, 2H), 4.16-3.88 (m, 7H), 3.86-3.67 (m, 3H), 2.47-2.32 (m, 2H), 2.27 (s, 2H), 2.16-2.05 (m, 1H), 2.01-1.79 (m, 3H), 1.75-1.59 (m, 3H), 1.23 (t, J=7.0 Hz, 3H) ppm.

Step 2: ethyl 4'-(8-chloroimidazo[1,5-a]pyrazin-3-yl)dispiro[[1,3]dioxolane-2,2'-bicyclo[2.2.2]octane-5',2"-[1,3]dioxolane]-1'-carboxylate A solution of ethyl 4'-(((3-chloropyrazin-2-yl)methyl)carbamoyl)dispiro[[1,3]dioxolane-2,2'-bicyclo[2.2.2]octane-5',2"-[1,3]dioxolane]-1'-carboxylate (500 mg, 1.07 mmol) in ACN (20 mL) was added PCl$_5$ (1.11 g, 5.34 mmol) at 0° C. under nitrogen, the mixture was stirred at 25° C. for 1 hour. The solution was added to aq NaHCO$_3$ at 0° C., and the mixture was extracted by DCM (20 mL). The organic layer was washed with H$_2$O (30 mL) and brine (30 mL), dried over anhydrous Na$_2$SO$_4$, concentrated to afford the crude product which was purified on silica gel chromatography with the eluent of PE:THF (5:1-1:1) to give the product.
$^1$H NMR (400 MHz, CDCl$_3$) δ=8.32-8.29 (m, 1H), 8.38-8.27 (m, 1H), 7.83-7.69 (m, 1H), 7.23-7.14 (m, 1H), 4.10 (q, J=7.0 Hz, 1H), 4.01-3.88 (m, 3H), 3.81-3.63 (m, 3H), 3.42-3.34 (m, 1H), 2.97-2.88 (m, 1H), 2.78 (d, J=6.3 Hz, 1H), 2.55 (d, J=16.8 Hz, 1H), 2.48-2.39 (m, 1H), 2.19 (d, J=14.1 Hz, 1H), 2.07 (d, J=14.5 Hz, 1H), 1.88-1.76 (m, 2H), 1.57 (br. s., 1H), 1.36 (s, 1H), 1.30-1.17 (m, 3H) ppm.

Step 3: ethyl 1'-(1-bromo-8-chloroimidazo[1,5-a]pyrazin-3-yl)dispiro[[1,3]dioxolane-2,2'-bicyclo[2.2.2]octane-5',2"-[1,3]dioxolane]-4'-carboxylate A solution of ethyl 4'-(8-chloroimidazo[1,5-a]pyrazin-3-yl)dispiro[[1,3]dioxolane-2,2'-bicyclo[2.2.2]octane-5',2"-[1,3]dioxolane]-1'-carboxylate (230 mg, 0.52 mmol) in ACN (5 mL) was added NBS (120 mg, 0.68 mmol) at 20° C. under nitrogen. The mixture was stirred at 25° C. for 1 hour. H$_2$O (10 mL) was added to the mixture, the mixture was extracted by EA (10 mL). The organic layer was washed with H$_2$O (20 mL) and brine (20 mL), dried over anhydrous Na$_2$SO$_4$, concentrated to afford the crude product of the title compound.
$^1$H NMR (400 MHz, CDCl$_3$) δ=8.41 (d, J=5.1 Hz, 1H), 7.18 (d, J=5.1 Hz, 1H), 4.14 (q, J=7.0 Hz, 2H), 4.04-3.93 (m, 4H), 3.89-3.72 (m, 4H), 3.00-2.87 (m, 3H), 2.79-2.70 (m, 4H), 2.61-2.41 (m, 4H), 2.21 (d, J=14.1 Hz, 2H), 2.15-1.99 (m, 2H), 1.90-1.76 (m, 2H), 1.26 (t, J=7.2 Hz, 4H) ppm.

Step 5: ethyl 1'-(8-amino-1-bromoimidazo[1,5-a]pyrazin-3-yl)dispiro[[1,3]dioxolane-2,2'-bicyclo[2.2.2]octane-5',2"-[1,3]dioxolane]-4'-carboxylate A solution of ethyl 1'-(1-bromo-8-chloroimidazo[1,5-a]pyrazin-3-yl)dispiro[[1,3]dioxolane-2,2'-bicyclo[2.2.2]octane-5',2"-[1,3]dioxolane]-4'-carboxylate (280 mg, 0.53 mmol) in i-PrOH (4 mL) was added NH$_3$H$_2$O (4 mL) at 25° C. The mixture was stirred at 100° C. for 16 hours in sealed tube. After the reaction, the mixture was concentrated to afford the crude product which was purified on silica gel chromatography with the eluent of PE:THF (5:1-1:1) to give the title compound.
$^1$H NMR (400 MHz, CDCl$_3$) δ=7.91 (d, J=5.1 Hz, 1H), 6.82 (d, J=5.5 Hz, 1H), 4.09 (q, J=6.8 Hz, 2H), 3.98-3.86 (m, 3H), 3.81-3.63 (m, 5H), 3.47 (d, J=6.3 Hz, 1H), 2.89-2.86 (m, 1H), 2.96-2.80 (m, 2H), 2.76-2.63 (m, 2H), 2.57-2.34 (m, 3H), 2.22-2.00 (m, 3H), 1.24-1.17 (m, 4H) ppm.

Step 6: 4-(8-amino-1-bromoimidazo[1,5-a]pyrazin-3-yl)-2,5-dioxobicyclo[2.2.2]octane-1-carboxylic acid A solution of ethyl 1'-(8-amino-1-bromoimidazo[1,5-a]pyrazin-3-yl)dispiro[[1,3] dioxolane-2,2'-bicyclo[2.2.2]octane-5',2"-[1,3]dioxolane]-4'-carboxylate (140 mg, 0.27 mmol) in HCl (5 mL, 2M) was stirred at 90° C. for 1 hour. After the reaction, the mixture was concentrated to afford the crude the title compound as solid. MS: 393.0 (M+1)

Intermediate 3

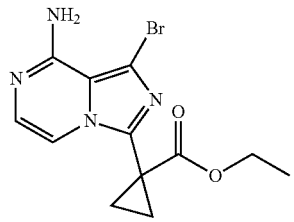 [SMILES: CCOC(=O)C1(c2nc(Br)c3c(N)nccn23)CC1]

ethyl 1-(8-amino-1-bromoimidazo[1,5-a]pyrazin-3-yl)cyclopropanecarboxylate

Step 1: ethyl 1-(((3-chloropyrazin-2-yl)methyl)carbamoyl)cyclopropanecarboxylate To a solution of 1-(ethoxycarbonyl)cyclopropanecarboxylic acid (200 mg, 1.265 mmol), (3-chloropyrazin-2-yl)methanamine (182 mg, 1.265 mmol), 4-methylmorpholine (640 mg, 6.32 mmol) and HOBT (48.4 mg, 0.316 mmol) in MeCN (20 mL) was added EDC (242 mg, 1.265 mmol) and the reaction was stirred at 20° C. for 16 hours. The solution was diluted with EtOAc (30 mL), washed with water (20 mL×3), 1N HCl aqueous (30 mL), and brine (30 mL). The organic layer was dried over Na$_2$SO$_4$, and concentrated in vacuo to give the title compound. $^1$H NMR (400 MHz, CDCl$_3$) δ: 9.78 (br. s., 1H), 8.51 (br. s., 1H), 8.29 (br. s., 1H), 4.76 (d, J=4.3 Hz, 2H), 4.17 (q, J=7.0 Hz, 2H), 1.77-1.65 (m, 2H), 1.58 (d, J=3.9 Hz, 2H), 1.25 (t, J=7.0 Hz, 3H) ppm.

Step 2: ethyl 1-(8-chloroimidazo[1,5-a]pyrazin-3-yl)cyclopropanecarboxylate

A solution of compound ethyl 1-(((3-chloropyrazin-2-yl)methyl)carbamoyl)cyclopropanecarboxylate (65 mg, 0.229 mmol) and PCl$_5$ (143 mg, 0.687 mmol) in MeCN (15 mL) was stirred at 80° C. for 2 hours and poured into 10% NaHCO$_3$ (50 mL). The mixture was extracted with EtOAc (20 mL×3). The combined organic layers were dried over K$_2$CO$_3$ and concentrated in vacuo to give the title compound. MS: 252 (M+1). $^1$H NMR (400 MHz, CDCl$_3$) δ: 7.80 (s, 1H), 7.68 (d, J=5.1 Hz, 1H), 7.40 (d, J=5.1 Hz, 1H), 4.14 (q, J=7.2 Hz, 2H), 1.93-1.82 (m, 2H), 1.61-1.48 (m, 2H), 1.15 (t, J=7.0 Hz, 3H) ppm.

Step 3: ethyl 1-(1-bromo-8-chloroimidazo[1,5-a]pyrazin-3-yl)cyclopropanecarboxylate To a solution of ethyl 1-(8-chloroimidazo[1,5-a]pyrazin-3-yl)cyclopropanecarboxylate (60 mg, 0.226 mmol) in MeCN (8 mL) was added NBS (48.2 mg, 0.271 mmol) and the reaction was stirred at 20° C. for 1 hour. The solution was quenched with Na$_2$SO$_3$ aqueous and the mixture was extracted with EtOAc (20 mL×2). The combined organic layers were washed with water, dried over Na$_2$SO$_4$ and concentrated in vacuo to give the title compound. MS: 332/334 (M+1).

Step 4: ethyl 1-(8-amino-1-bromoimidazo[1,5-a]pyrazin-3-yl)cyclopropanecarboxylate A solution of ethyl 1-(1-bromo-8-chloroimidazo[1,5-a]pyrazin-3-yl)cyclopropanecarboxylate (78 mg, 0.226 mmol) in ammonia/propan-2-ol (15 mL, 60.0 mmol, 4M) was stirred at 100° C. for 16 hours. Then the mixture was concentrated in vacuo. The residue was dissolved in EtOAc (25 mL), washed with water. The combined organic layers were dried over Na$_2$SO$_4$ and concentrated in vacuo to give the title compound. MS: 311/313 (M+1).

Intermediate 4

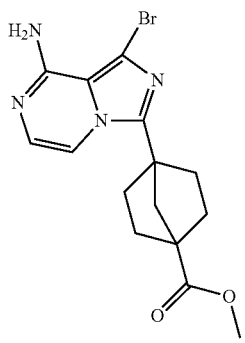 [SMILES: COC(=O)C12CCC(c3nc(Br)c4c(N)nccn34)(CC1)C2]

Methyl 4-(8-amino-1-bromoimidazo[1,5-a]pyrazin-3-yl)bicyclo[2.2.1]heptane-1-carboxylate Step 1: dimethyl bicyclo[2.2.1]heptane-1,4-dicarboxylate To a solution of HMPA (13.08 mL, 75 mmol) and LDA (13.43 mL, 26.9 mmol) in THF (30 mL) was added a solution of dimethyl cyclopentane-1,3-dicarboxylate (2 g, 10.74 mmol) in 10 mL THF dropwise over 30 minutes at −78° C. under N$_2$ protection and stirred at one point for another 30 minutes. The solution was warmed to 0° C. and stirred at one point for 1 hour. The solution was cooled to −78° C. and added a solution of 1-bromo-2-chloroethane (1.848 g, 12.89 mmol) in 10 mL THF dropwise. The solution was stirred at −78° C. for 1 hour and warmed to RT. After stirred for 16 hours, the solution was added 1N HCl and extracted with EtOAc. The combined organic layer was dried over Na$_2$SO$_4$, concentrated in vacuo to give the title compound. $^1$H NMR (CDCl$_3$ 400 MHz): δ 3.67 (s, 6H), 2.01 (d, J=6.7 Hz, 4H), 1.89 (s, 2H), 1.66 (d, J=6.7 Hz, 3H) ppm.

Step 2: bicyclo[2.2.1]heptane-1,4-dicarboxylic acid

A solution of dimethyl bicyclo[2.2.1]heptane-1,4-dicarboxylate (500 mg, 2.356 mmol) and LiOH (169 mg, 7.07 mmol) in water (20 mL) and MeOH (10 mL) was stirred at RT for 48 hours. The solution was poured into 1 N HCl and extracted with EtOAc. The combined organic was dried over Na$_2$SO$_4$ and concentrated in vacuo to give crude title compound.

Step 3: methyl 4-(((3-chloropyrazin-2-yl)methyl)carbamoyl)bicyclo[2.2.1]heptane-1-carboxylate To a solution of DMF (0.1 mL, 1.291 mmol) and bicyclo[2.2.1]heptane-1,4-dicarboxylic acid (450 mg, 2.443 mmol) in DCM (20 mL) was added oxalyl chloride (0.732 mL, 8.36 mmol) dropwise. The mixture was stirred at RT for 16 hours. The solution was concentrated in vacuo and dissolved in MeCN. To the solution was added a solution of (3-chloropyrazin-2-yl)methanamine (200 mg, 1.393 mmol) and TEA (1.942 mL, 13.93 mmol) in MeCN (100 mL) dropwise over 6 hours at 0° C. The solution was stirred at RT for another 1 hour and added MeOH (20.00 mL). The solution was stirred for 16 hours and added (diazomethyl)trimethylsilane (13.93 mL, 13.93 mmol). The solution was stirred for another 4 hours and added 30 mL 1N HCl. The solution was extracted with EtOAc and washed with water, brine, dried over Na$_2$SO$_4$ and purified by chromatography over silica gel to give the title compound. MS: 324/326 (M+1).

Step 4: methyl 4-(8-chloroimidazo[1,5-a]pyrazin-3-yl)bicyclo[2.2.1]heptane-1-carboxylate A solution of methyl 4-(((3-chloropyrazin-2-yl)methyl)carbamoyl)bicyclo[2.2.1] heptane-1-carboxylate (55 mg, 0.170 mmol) and pentachlorophosphorane (70.7 mg, 0.340 mmol) in MeCN (10 mL) was stirred at RT for 3 hours. The mixture was poured into 5% NaHCO$_3$ and extracted with EtOAc. The combined organic was washed with NaHCO$_3$ and water, dried over Na$_2$CO$_3$, concentrated in vacuo to give the title compound.

Step 5: methyl 4-(1-bromo-8-chloroimidazo[1,5-a]pyrazin-3-yl)bicyclo[2.2.1] heptane-1-carboxylate A solution of methyl 4-(8-chloroimidazo[1,5-a]pyrazin-3-yl)bicyclo[2.2.1]heptane-1-carboxylate (48 mg, 0.157 mmol) and NBS (27.9 mg, 0.157 mmol) in MeCN (15 mL) was stirred at RT for 1 hour. The solution was added 20 mL EtOAc and washed with NH$_4$Cl, dried over Na$_2$SO$_4$ and concentrated in vacuo to give the title compound. MS: 384/386 (M+1).

Step 5: methyl 4-(8-amino-1-bromoimidazo[1,5-a]pyrazin-3-yl)bicyclo[2.2.1] heptane-1-carboxylate A solution methyl 4-(1-bromo-8-chloroimidazo[1,5-a]pyrazin-3-yl) bicyclo[2.2.1] heptane-1-carboxylate (60 mg, 0.156 mmol) in ammonia, propan-2-ol (20 mL, 80 mmol) was stirred at 95° C. for 16 hours. The solution was concentrated in vacuo and dissolved in 20 mL EtOAc. The solution was washed with water, dried over Na$_2$SO$_4$ and concentrated in vacuo to give the title compound. MS: 365/367 (M+1).

Intermediate 5

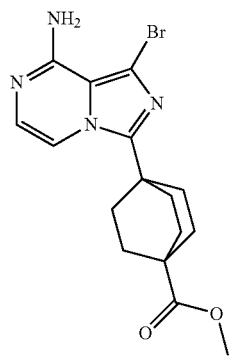 [SMILES: COC(=O)C12CCC(c3nc(Br)c4c(N)nccn34)(CC1)CC2]

methyl 4-(8-amino-1-bromoimidazo[1,5-a]pyrazin-3-yl)bicyclo[2.2.2]octane-1-carboxylate Intermediate 5 was prepared in the same procedure as intermediate 4 using 4-(methoxycarbonyl)bicyclo[2.2.2]octane-1-carboxylic acid as the starting material for step 1 to provide the title product methyl 4-(8-amino-1-bromoimidazo[1,5-a]pyrazin-3-yl)bicyclo[2.2.2]octane-1-carboxylate. LC-MS: (M+1)$^+$ 381.0, Retention time=1.20 min (Method D).

Intermediate 6

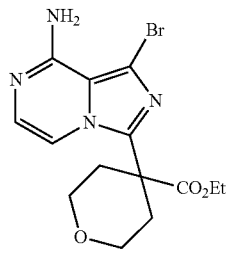 [SMILES: CCOC(=O)C1(c2nc(Br)c3c(N)nccn23)CCOCC1]

ethyl 4-(8-amino-1-bromoimidazo[1,5-a]pyrazin-3-yl)tetrahydro-2H-pyran-4-carboxylate

Step 1: 4-(ethoxycarbonyl)tetrahydro-2H-pyran-4-carboxylic acid

To a solution of diethyl dihydro-2H-pyran-4,4(3H)-dicarboxylate (900 mg, 3.9 mmol) in EtOH (30 mL) was added NaOH aqueous (3.9 mL, 1 mol/L). The reaction was stirred at 20° C. for 18 hours, then it was concentrated in vacuum. The residue was diluted in water and acidified to pH=6. The mixture was extracted with EtOAc (40 mL). The organic layer was washed with brine (20 mL×2), dried over with Na$_2$SO$_4$, concentrated under vacuum to give the title compound, which was used directly for the next step.

Step 2: ethyl 4-(((3-chloropyrazin-2-yl)methyl)carbamoyl)tetrahydro-2H-pyran-4-carboxylate To a solution of 4-(ethoxycarbonyl)tetrahydro-2H-pyran-4-carboxylic acid (600 mg, 2.97 mmol) and DIEA (1.14 mg, 3.9 mmol) in THF (20 mL) was added HATU (1.12 g, 2.97 mmol) at 20° C., then (3-chloropyrazin-2-yl)methanamine (510 mg, 3.56 mmol) was added. The mixture was concentrated under vacuum, and the residue was purified with silica gel column chromatography (20 g, Pet.Ether:EtOAc=70:30) to give the title compound. MS: 328.1 (M+1).

Step 3: ethyl 4-(8-chloroimidazo[1,5-a]pyrazin-3-yl)tetrahydro-2H-pyran-4-carboxylate To a solution of ethyl 4-(((3-chloropyrazin-2-yl)methyl)carbamoyl)tetrahydro-2H-pyran-4-carboxylate (239 mg 0.95 mmol) in ACN (20 mL) was added PCl$_5$ (600 mg 2.88 mmol). The reaction mixture was stirred at 60° C. for 2 hours. The mixture was poured into sat. NaHCO$_3$ aqueous, then it was extracted with EtOAc (30 mL×3), the organic layer was washed with brine (20 mL×2), dried over with Na$_2$SO$_4$, concentrated in vacuum to give the crude title compound. MS: 310.1 (M+1).

Step 4: ethyl 4-(1-bromo-8-chloroimidazo[1,5-a]pyrazin-3-yl)tetrahydro-2H-pyran-4-carboxylate To a solution of ethyl 4-(8-chloroimidazo[1,5-a]pyrazin-3-yl)tetrahydro-2H-pyran-4-carboxylate (336 mg 1.09 mmol) in ACN (20 mL) was added NBS (193 mg, 1.09 mmol). The reaction was stirred at 20° C. for 2 hours. The mixture was poured into sat. Na$_2$SO$_3$ aqueous, then it was extracted with EtOAc (30 mL×2), the organic layer was washed with brine (20 mL×2), dried over with Na$_2$SO$_4$, concentrated in vacuum to give the title compound. MS: 390.0 (M+1).

Step 5: ethyl 4-(8-amino-1-bromoimidazo[1,5-a]pyrazin-3-yl)tetrahydro-2H-pyran-4-carboxylate The compound ethyl 4-(1-bromo-8-chloroimidazo[1,5-a]pyrazin-3-yl)tetrahydro-2H-pyran-4-carboxylate (370 mg, 0.96 mmol) was added in NH$_3$/i-PrOH (20 mL, 4M). The mixture was stirred at 100° C. for 15 hours under sealed tube. Then the reaction was quenched with water (30 mL). The mixture was extracted by EtOAc (30 mL×2), the organic layer was washed with brine (20 mL×2), dried over with Na$_2$SO$_4$, concentrated under vacuum to give the title compound. MS: 369.0/371.0 (M+1).

Intermediate 7

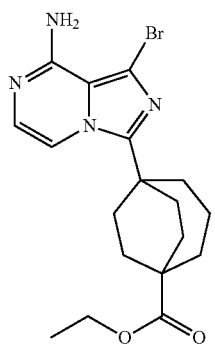 [SMILES: CCOC(=O)C12CCCC(c3nc(Br)c4c(N)nccn34)(CC1)CC2]

ethyl 5-(8-amino-1-bromoimidazo[1,5-a]pyrazin-3-yl)bicyclo[3.2.2]nonane-1-carboxylate Step 1: 5-(((3-chloropyrazin-2-yl)methyl)carbamoyl)bicyclo[3.2.2]nonane-1-carboxylic acid To a mixture of bicyclo[3.2.2]nonane-1,5-dicarboxylic acid (200 mg, 0.942 mmol) and TEA (0.328 ml, 2.356 mmol) in THF (10 ml) was added HATU (340 mg, 0.895 mmol) at 0° C. The mixture was stirred at this temperature for 10 mins and at 25° C. for another 20 mins. (3-chloropyrazin-2-yl)methanamine hydrochloride (170 mg, 0.942 mmol) was added to above solution at 0° C. and the mixture was allowed to warm to room temperature. The mixture was stirred at room temperature for 30 mins. The mixture was treated with water (20 mL) and EA (20 mL). The EA layer was separated and was washed with brine (20 mL), dried over Na$_2$SO$_4$, filtered and concentrated. The residue was used next step without further purification.

Step 2: ethyl 5-(((3-chloropyrazin-2-yl)methyl)carbamoyl)bicyclo[3.2.2]nonane-1-carboxylate To a solution of 5-(((3-chloropyrazin-2-yl)methyl)carbamoyl)bicyclo[3.2.2]nonane-1-carboxylic acid (478 mg, 1.415 mmol) and K$_2$CO$_3$ (489 mg, 3.54 mmol) in DMF (20 ml) was added iodomethane (0.137 ml, 1.698 mmol) at 25° C. The mixture was stirred at this temperature for 2 hours. TLC showed the reaction was completed. The mixture was treated with EA (40 mL) and water 20 (mL). The EA layer was separated and was washed with water three times (3×20 mL), brine (20 mL), dried over Na$_2$SO$_4$. The mixture was filtered and the filtrate was concentrated. The residue was purified by silica gel column chromatography (PE/THF=5/1) to afford the product compound ethyl 5-(((3-chloropyrazin-2-yl)methyl)carbamoyl)bicyclo[3.2.2]nonane-1-carboxylate as solid.

Step 3: ethyl 5-(8-chloroimidazo[1,5-a]pyrazin-3-yl)bicyclo[3.2.2]nonane-1-carboxylate A mixture of ethyl 5-(((3-chloropyrazin-2-yl)methyl)carbamoyl)bicyclo[3.2.2]nonane-1-carboxylate (430 mg, 1.175 mmol) and PCl5 (1224 mg, 5.88 mmol) in MeCN (20 ml) was stirred at 60° C. for 2 hours. The mixture was quenched with saturated NaHCO$_3$ and extracted with EA. The EA layer was washed with brine and dried over anhydrous Na$_2$SO$_4$. The mixture was filtered and the filtrate was concentrated. The residue was purified by silica gel column chromatography (PE/THF=3/1) to afford the product compound ethyl 5-(8-chloroimidazo[1,5-a]pyrazin-3-yl)bicyclo[3.2.2]nonane-1-carboxylate.

Step 4: ethyl 5-(1-bromo-8-chloroimidazo[1,5-a]pyrazin-3-yl) bicyclo[3.2.2]nonane-1-carboxylate A mixture of ethyl 5-(8-chloroimidazo[1,5-a]pyrazin-3-yl)bicyclo[3.2.2]nonane-1-carboxylate (240 mg, 0.690 mmol) and NBS (123 mg, 0.690 mmol) in MeCN (20 mL) was stirred at 25° C. for 30 mins. The mixture was treated with water (20 mL) and EA (20 mL). The EA layer was separated and was washed with water, brine, dried over Na$_2$SO$_4$, filtered and concentrated in vacuo. The residue was purified by silica gel column chromatography (PE/THF=3/1) to afford ethyl 5-(1-bromo-8-chloroimidazo[1,5-a]pyrazin-3-yl)bicyclo[3.2.2]nonane-1-carboxylate.

Step 5: ethyl 5-(8-amino-1-bromoimidazo[1,5-a]pyrazin-3-yl)bicyclo[3.2.2]nonane-1-carboxylate A solution of ethyl 5-(1-bromo-8-chloroimidazo[1,5-a]pyrazin-3-yl)bicyclo[3.2.2]nonane-1-carboxylate (35 mg, 0.082 mmol) in 10 ml 4N NH3/i-PrOH was stirred at 90° C. for 16 hours. The mixture was filtered and the filtrate was concentrated. The residue was purified by silica gel column chromatography (PE/THF1/1) to afford the product compound ethyl 5-(8-amino-1-bromoimidazo[1,5-a]pyrazin-3-yl)bicyclo[3.2.2]nonane-1-carboxylate.

Intermediate 8

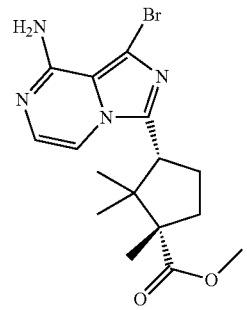 [SMILES: COC(=O)[C@@]1(C)CC[C@@H](c2nc(Br)c3c(N)nccn23)C1(C)C]

(1S,3R)-methyl 3-(8-amino-1-bromoimidazo[1,5-a]pyrazin-3-yl)-1,2,2-trimethylcyclopentanecarboxylate Step 1: (1S,3R)-dimethyl 1,2,2-trimethylcyclopentane-1,3-dicarboxylate To a suspension of (1S,3R)-1,2,2-trimethylcyclopentane-1,3-dicarboxylic acid (4.87 g, 24.32 mmol) and K$_2$CO$_3$ (10.08 g, 73.0 mmol) in DMF (50 mL) was stirred at 13° C. and iodomethane (12.62 g, 89 mmol) was added. Then the mixture was stirred at 13° C. for 3 h. The reaction mixture was added EtOAc (100 mL) and washed with water and brine, dried over Na$_2$SO$_4$ and concentrated to give the title compound. $^1$H NMR (400 MHz, MeOH-d4): δ3.66 (d, J=3.9 Hz, 6H), 2.87 (t, J=9.4 Hz, 1H), 2.54 (dt, J=7.6, 12.6 Hz, 1H), 2.21-2.08 (m, 1H), 1.90-1.76 (m, 1H), 1.50 (ddd, J=3.9, 9.6, 13.5 Hz, 1H), 1.22 (d, J=12.5 Hz, 6H), 0.73 (s, 3H) ppm.

Step 2: (1S,3R)-3-(methoxycarbonyl)-2,2,3-trimethylcyclopentanecarboxylic acid

To a solution of (1S,3R)-dimethyl 1,2,2-trimethylcyclopentane-1,3-dicarboxylate (5.37 g, 23.52 mmol) and lithium hydroxide hydrate (0.987 g, 23.52 mmol) in MeOH (60 mL) was stirred at 10° C. for 40 h. It was no reaction detected by TLC. The mixture was concentrated to remove MeOH (20 mL), and then 5 mL of water was added and stirred at 30° C. for overnight. The reaction was incomplete detected by TLC. The mixture was heated to 50° C. for overnight. The reaction was complete detected by TLC. The mixture was concentrated to remove solvent, and then added water (100 mL), washed with EtOAc. The water layer was added HCl to adjust to pH=3, and then the mixture was extracted with EtOAc (3×30 mL), the organic layer was dried over Na$_2$SO$_4$ and concentrated to give the title compound. $^1$H NMR (400 MHz, CDCl$_3$): δ 3.69 (s, 3H), 2.84 (t, J=9.4 Hz, 1H), 2.59

(dt, J=7.6, 12.6 Hz, 1H), 2.22-2.12 (m, 1H), 1.90-1.78 (m, 1H), 1.53 (ddd, J=3.9, 9.6, 13.5 Hz, 1H), 1.33-1.26 (m, 3H), 1.22 (s, 3H), 0.85 (s, 3H) ppm.

Step 2: (1S,3R)-methyl 3-(((3-chloropyrazin-2-yl)methyl)carbamoyl)-1,2,2-trimethyl cyclopentanecarboxylate To a mixture of (1S,3R)-3-(methoxycarbonyl)-2,2,3-trimethylcyclopentanecarboxylic acid (4.93 g, 23.01 mmol) and TEA (9.62 mL, 69.0 mmol) and HATU (13.12 g, 34.5 mmol) in DCM (100 mL) was stirred at 12° C. for 30 min. (3-chloropyrazin-2-yl) methanamine hydrochloride (4.97 g, 27.6 mmol) was added and the mixture was stirred at 12° C. for overnight. The mixture was added DCM (100 mL) and washed and brine. The organic layer was dried over Na$_2$SO$_4$, purified with silica gel to give the title compound. $^1$H NMR (400 MHz, CDCl$_3$): δ 8.46 (d, J=2.3 Hz, 1H), 8.34 (s, 1H), 6.70 (br. s., 1H), 4.81-4.66 (m, 2H), 3.69 (s, 3H), 2.74 (t, J=9.2 Hz, 1H), 2.65 (dt, J=6.8, 12.6 Hz, 1H), 2.34-2.22 (m, 1H), 1.91-1.80 (m, 1H), 1.54 (ddd, J=4.1, 9.6, 13.7 Hz, 1H), 1.32 (s, 3H), 1.25 (s, 3H), 0.81 (s, 3H) ppm.

Step 3: (1S,3R)-methyl 3-(8-chloroimidazo[1,5-a]pyrazin-3-yl)-1,2,2-trimethylcyclopentanecarboxylate (1S,3R)-methyl 3-(((3-chloropyrazin-2-yl)methyl)carbamoyl)-1,2,2-trimethylcyclopentanecarboxylate (7.76 g, 22.84 mmol) was dissolved in acetonitrile (100 mL) and cooled to 0° C., PCl$_5$ (14.27 g, 68.5 mmol) was added slowly. The mixture was stirred at room temperature for 30 min. The reaction was poured into saturated sodium bicarbonate at 0° C. Then the mixture was extracted with EtOAc, dried over anhydrous sodium sulfate and sodium carbonate, filtered and concentrated to give crude title compound.

Step 4: (1S,3R)-methyl 3-(1-bromo-8-chloroimidazo[1,5-a]pyrazin-3-yl)-1,2,2-trimethyl cyclopentanecarboxylate NBS (4.28 g, 24.03 mmol) was added in portions to a stirred solution of (1S,3R)-methyl 3-(8-chloroimidazo[1,5-a]pyrazin-3-yl)-1,2,2-trimethylcyclopentane carboxylate (7.03 g, 21.85 mmol) in acetonitrile (80 mL). The mixture was stirred at 12° C. for 1 h. The reaction was added saturated sodium sulfite and extracted with EtOAc, the organic layer was dried over anhydrous sodium sulfate, purified with silica gel to give the title compound. $^1$H NMR (400 MHz, CDCl$_3$): δ7.69 (d, J=4.7 Hz, 1H), 7.29 (d, J=5.1 Hz, 1H), 3.70 (s, 3H), 3.53 (t, J=9.4 Hz, 1H), 2.82 (dt, J=6.3, 12.9 Hz, 1H), 2.70-2.59 (m, 1H), 2.15-2.06 (m, 1H), 1.67 (ddd, J=4.3, 9.5, 13.6 Hz, 1H), 1.38 (s, 2H), 1.13 (s, 2H), 0.75 (s, 2H) ppm.

Step 5: (1S,3R)-methyl 3-(8-amino-1-bromoimidazo[1,5-a]pyrazin-3-yl)-1,2,2-trimethyl cyclopentanecarboxylate To a mixture of (1S, 3R)-methyl 3-(1-bromo-8-chloroimidazo[1,5-a]pyrazin-3-yl)-1,2,2-trimethylcyclopentanecarboxylate (4 g, 9.98 mmol) and NH$_3$.H$_2$O (20 mL) in 2-propanol (20 mL) was stirred at 110° C. for overnight on a sealed tube. The reaction mixture was concentrated to remove solvent. And then the mixture was added water (50 mL), extracted with EtOAc, The organic layer was purified with silica gel to give the title compound. $^1$H NMR (400 MHz, CDCl$_3$): δ 7.27-7.26 (d, J=4 Hz, 1H), 7.01-7.00 (m, 1H), 5.73 (br. s., 2H), 3.69 (s, 3H), 3.49 (t, J=9.8 Hz, 1H), 2.80 (dt, J=6.3, 12.7 Hz, 1H), 2.65-2.54 (m, 1H), 2.11-1.99 (m, 1H), 1.64 (ddd, J=4.3, 9.7, 13.8 Hz, 1H), 1.36 (s, 3H), 1.12 (s, 3H), 0.75 (s, 3H) ppm.

Intermediate 9

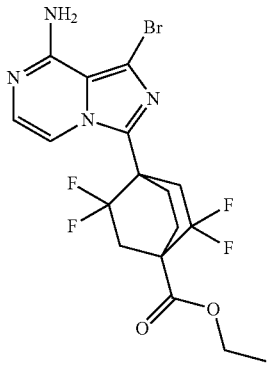 [SMILES: CCOC(=O)C12CCC(c3nc(Br)c4c(N)nccn34)(CC1(F)F)C(F)(F)C2]

ethyl 4-(8-amino-1-bromoimidazo[1,5-a]pyrazin-3-yl)-2,2,5,5-tetrafluorobicyclo[2.2.2]octane-1-carboxylate Step 1: diethyl 2,2,5,5-tetrafluorobicyclo[2.2.2]octane-1,4-dicarboxylate A solution of diethyl bicyclo[2.2.2]octane-1,4-dicarboxylate (500 mg, 1.75 mmol) in DCM (5 mL) was added DAST (704 mg, 4.37 mmol) at 0° C. The mixture was stirred at 0° C. for 1 hour. After the reaction, aq NaHCO$_3$ was added to the mixture. The mixture was extracted by EA (10 mL). The organic layer was washed with H$_2$O (20 mL) and brine (20 mL), dried over Na$_2$SO$_4$, concentrated to afford the crude product, which was purified on silica gel chromatography with the eluent of PE:THF (10:1-5:1) to give the title compound.
$^1$H NMR (400 MHz, CDCl$_3$) δ=5.10-4.88 (m, 1H), 4.28-4.06 (m, 4H), 2.72-2.58 (m, 1H), 2.40-2.22 (m, 2H), 2.18 (s, 2H), 2.16-2.09 (m, 1H), 2.09-1.80 (m, 3H), 1.78-1.63 (m, 1H), 1.35-1.19 (m, 6H) ppm.

Step 2: 2,2,5,5-tetrafluoro-4-(methoxycarbonyl)bicyclo[2.2.2]octane-1-carboxylic acid A solution of diethyl 2,2,5,5-tetrafluorobicyclo[2.2.2]octane-1,4-dicarboxylate (100 mg, 0.31 mmol) in THF (2 mL) was added a solution of NaOH (12 mg, 0.3 mmol) in EtOH (2 mL) at 25° C. The mixture was stirred at 25° C. for 16 hours. After the reaction, HCl (0.5 mL, 2M) was added to the mixture. The mixture was extracted by EA (10 mL). The organic layer was washed with H$_2$O (20 mL) and brine (20 mL), dried over anhydrous Na$_2$SO$_4$, concentrated to afford the crude product of title compound as solid.

Step 3: methyl 4-(((3-chloropyrazin-2-yl)methyl)carbamoyl)-2,2,5,5-tetrafluorobicyclo [2.2.2]octane-1-carboxylate A solution of 2,2,5,5-tetrafluoro-4-(methoxycarbonyl)bicyclo[2.2.2]octane-1-carboxylic acid (70 mg, 0.23 mmol) in DCM (2 mL) was added (CClO)₂ (42 mg, 0.33 mmol) at 0° C., the mixture was stirred at 25° C. for 1 hour. The mixture was concentrated in vacuo. The residue was dissolved in DCM (2 mL). The solution was added into a solution of (3-chloropyrazin-2-yl) methanamine (27 mg, 0.18 mmol) and Et₃N (0.075 mL, 0.54 mmol) in 1 mL of DCM at 0° C. And the mixture was stirred at 25° C. for 1 hour. H₂O (20 mL) was added to the mixture, the mixture was extracted by EA (10 mL). The organic layer was washed with H₂O (10 mL) and brine (10 mL), dried over Na₂SO₄, concentrated to afford the crude product, which was purified on silica gel chromatography with the eluent of PE:THF (5:1-1:1) to give the title compound as a solid. ¹H NMR (400 MHz, CDCl₃) δ=8.45 (br. s., 1H), 8.37-8.27 (m, 1H), 7.49 (br. s., 1H), 7.34-7.26 (m, 1H), 4.81-4.62 (m, 2H), 3.87-3.73 (m, 3H), 2.79-2.59 (m, 2H), 2.54-2.31 (m, 3H), 2.21-1.93 (m, 2H), 1.88-1.72 (m, 1H) ppm.

Step 4: methyl 4-(8-chloroimidazo[1,5-a]pyrazin-3-yl)-2,2,5,5-tetrafluorobicyclo [2.2.2]octane-1-carboxylate A solution of methyl 4-(((3-chloropyrazin-2-yl)methyl) carbamoyl)-2,2,5,5-tetrafluorobicyclo[2.2.2]octane-1-carboxylate (200 mg, 0.48 mmol) in MeCN (3 mL) was added PCl₅ (500 mg, 2.44 mmol) at 0° C. under nitrogen, the mixture was stirred at 80° C. for 16 hours. The solution was added to aq NaHCO₃ at 0° C., and the mixture was extracted by DCM (20 mL). The organic layer was washed with H₂O (30 mL) and brine (30 mL), dried over Na₂SO₄, concentrated to afford the crude product which was purified on silica gel chromatography with the eluent of PE:THF (5:1-1:1) to give methyl 4-(8-chloroimidazo[1,5-a]pyrazin-3-yl)-2,2,5,5-tetrafluorobicyclo[2.2.2]octane-1-carboxylate. ¹H NMR (400 MHz, CDCl₃) δ=8.45 (d, J=2.0 Hz, 1H), 8.31 (br. s., 1H), 7.98 (d, J=4.7 Hz, 1H), 7.31 (d, J=5.1 Hz, 1H), 3.86 (s, 2H), 3.83-3.76 (m, 3H), 3.19-3.03 (m, 1H), 2.83-2.69 (m, 4H), 2.64-2.43 (m, 4H), 2.02-1.88 (m, 2H) ppm.

Step 5: ethyl 4-(1-bromo-8-chloroimidazo[1,5-a]pyrazin-3-yl)-2,2,5,5-tetrafluorobicyclo [2.2.2]octane-1-carboxylate A solution of methyl 4-(8-chloroimidazo[1,5-a]pyrazin-3-yl)-2,2,5,5-tetrafluorobicyclo[2.2.2]octane-1-carboxylate (80 mg, 0.2 mmol) in MeCN (5 mL) was added NBS (47 mg, 2.36 mmol) at 20° C. under nitrogen. The mixture was stirred at 25° C. for 1 hour. H₂O (10 mL) was added to the mixture, the mixture was extracted by EA (10 mL). The organic layer was washed with H₂O (20 mL) and brine (20 mL), dried over Na₂SO₄, concentrated to afford the crude product of ethyl 4-(1-bromo-8-chloroimidazo[1,5-a]pyrazin-3-yl)-2,2,5,5-tetrafluorobicyclo[2.2.2]octane-1-carboxylate. MS: 472.0 (M+1)

Step 6: ethyl 4-(8-amino-1-bromoimidazo[1,5-a]pyrazin-3-yl)-2,2,5,5-tetrafluorobicyclo [2.2.2]octane-1-carboxylate A solution of ethyl 4-(1-bromo-8-chloroimidazo[1,5-a]pyrazin-3-yl)-2,2,5,5-tetrafluorobicyclo[2.2.2]octane-1-carboxylate (120 mg, 0.25 mmol) in i-PrOH (4 mL) was added NH₃H₂O (4 mL) at 25° C. in sealed tube. The mixture was stirred at 100° C. for 16 hours. After the reaction mixture cooled, the mixture was concentrated to afford the crude product of title compound as solid. MS: 464.0 (M+1).

Intermediate 10

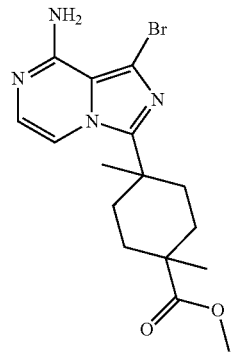 [SMILES: COC(=O)C1(C)CCC(C)(c2nc(Br)c3c(N)nccn23)CC1]

7-(8-Amino-1-bromo-imidazo[1,5-a]pyrazin-3-yl)-3-methyl-hexahydro-pyrido[2,1-c][1,4]oxazin-4-one Step 1: dimethyl 1,4-dimethylcyclohexane-1,4-dicarboxylate To a solution of LDA (125 mL, 250 mmol) and HMPA (139 mL, 799 mmol) in THF (250 mL) was added a solution of dimethyl cyclohexane-1,4-dicarboxylate (20 g, 100 mmol) in 20 mL THF dropwise at −78° C. under N₂ and stirred at −78° C. for 1 hour. The solution stirred at 0° C. for 1 hour. To the solution was added MeI (77.49 g, 546 mmol) at −78° C. and stirred at RT for 1 hour. The solution was added 1N HCl (30 mL) and extracted with EtOAc. The combined organic layers were dried over Na₂SO₄ and purified by chromatography on silica gel to give the title compound. ¹H NMR (400 MHz, CDCl₃) δ=3.69 (s, 6H), 2.13-2.02 (m, 4H), 1.26-1.19 (m, 4H), 1.13 (s, 6H) ppm.

Step 2: 4-(methoxycarbonyl)-1,4-dimethylcyclohexanecarboxylic acid

A solution of dimethyl 1,4-dimethylcyclohexane-1,4-dicarboxylate (900 mg, 3.94 mmol) and KOH (265 mg, 4.73 mmol) in MeOH (15 mL) and water (15 mL) was stirred at 80° C. for 16 hours. The solution was concentrated in vacuo and added 1N HCl and extracted with EtOAc. The combined organic layers were dried over Na₂SO₄ and concentrated in vacuo to give the crude title compound.

Step 3: (3R,6S)-methyl 1-((R)-2-chloropropanoyl)-6-(hydroxymethyl)piperidine-3-carboxylate To a solution of DMF (0.1 mL, 1.291 mmol) and 4-(methoxycarbonyl)-1,4-dimethyl cyclohexanecarboxylic acid (845 mg, 3.94 mmol) in DCM (30 mL) was added (COCl)₂ (0.690 mL, 7.89 mmol) dropwise and stirred at room temperature for 16 hours. The solution was concentrated in vacuo and dissolved in MeCN (15 mL). To the solution was added a solution of methyl 4-(8-amino-1-bromoimidazo[1,5-a]pyrazin-3-yl)-1,4-dimethyl cyclohexanecarboxylate (852 mg, 4.73 mmol) and TEA (5.50 mL, 39.4 mmol) in 50 mL MeCN dropwise over 6 hours at 0° C. The solution was stirred at room temperature for another 1 hour and added MeOH (15 mL). The solution was stirred for 16 hours and added 30 mL 1N HCl. The solution was extracted with EtOAc and washed with water, brine, dried over Na₂SO₄ and purified by chromatography over silica gel (12 g) to give the title compound. ¹H NMR (CDCl₃ 400 MHz) δ 8.46 (d, J=2.5 Hz, 1H), 8.33 (s, 1H), 7.01 (br. s., 1H), 4.71 (d, J=4.5 Hz, 2H), 3.70 (s, 3H), 2.13-2.05 (m, 4H), 1.43-1.31 (m, 4H), 1.18 (s, 3H), 1.14 (s, 3H) ppm.

Step 4: methyl 4-(8-chloroimidazo[1,5-a]pyrazin-3-yl)-1,4-dimethylcyclohexanecarboxylate A solution of methyl 4-(((3-chloropyrazin-2-yl)methyl)carbamoyl)-1,4-dimethyl cyclohexanecarboxylate (1 g, 2.94 mmol) and PCl₅ (0.919 g, 4.41 mmol) in MeCN (20 mL) was stirred at RT for 2 hours. The solution was poured into 5% NaHCO₃ and extracted with EtOAc. The combined organic was dried over K₂CO₃ and concentrated in vacuo to give the crude title compound.

Step 5: methyl 4-(1-bromo-8-chloroimidazo[1,5-a]pyrazin-3-yl)-1,4-dimethylcyclohexanecarboxylate A mixture of methyl 4-(8-chloroimidazo[1,5-a]pyrazin-3-yl)-1,4-dimethylcyclohexane carboxylate (0.95 g, 2.95 mmol) in MeCN (30 mL) was added NBS (0.788 g, 4.43 mmol) and stirred at room temperature for 2 hours. The mixture was added 30 mL EtOAc, washed with Na₂SO₃, dried over Na₂SO₄, concentrated in vacuo and purified by chromatography over silica gel (20 g) to give the title compound. MS: 402 (M+1).

Step 6: methyl 4-(8-amino-1-bromoimidazo[1,5-a]pyrazin-3-yl)-1,4-dimethyl cyclohexanecarboxylate A solution of methyl 4-(1-bromo-8-chloroimidazo[1,5-a]pyrazin-3-yl)-1,4-dimethyl cyclohexanecarboxylate (650 mg, 1.622 mmol) in ammonia, propan-2-ol (25 mL, 100 mmol) was stirred at 100° C. for 16 hours. The solution was concentrated in vacuo to give the title compound. MS: 381/383 (M+1).

Intermediate 11

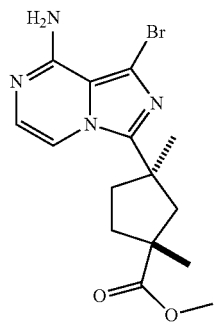 [SMILES: COC(=O)[C@]1(C)CC[C@@](C)(c2nc(Br)c3c(N)nccn23)C1]

trans-methyl 3-(8-amino-1-bromoimidazo[1,5-a]pyrazin-3-yl)-1,3-dimethylcyclopentanecarboxylate Step 1: trans-dimethyl 1,3-dimethylcyclopentane-1,3-dicarboxylate To a solution of dimethyl cyclopentane-1,3-dicarboxylate (10 g, 53.7 mmol) in THF (20 mL) was added a solution of MeI (41.0 mL, 655 mmol) in 10 mL toluene under N₂ protection dropwise at −78° C. and stirred at −78° C. for 25 minutes. To the solution was added a solution of LDA (161 mL, 322 mmol) in 10 mL toluene dropwise and stirred at room temperature for another 16 hours. The solution was poured into water and extracted with EtOAc. The combined organic layers were washed with water and brine, dried over Na₂SO₄, concentrated in vacuo and purified by chromatography over silica gel (120 g) to give the title compound. ¹H NMR (trans) (400 MHz, CDCl₃): δ3.69 (s, 6H), 2.29-2.20 (m, 2H), 2.15 (s, 2H), 1.65-1.57 (m, 2H), 1.34-1.21 (m, 6H) ppm. ¹H NMR (cis) (400 MHz, CDCl₃): δ3.70-3.60 (m, 6H), 2.85 (d, J=14.1 Hz, 1H), 2.32-2.20 (m, 2H), 1.61-1.52 (m, 2H), 1.32-1.24 (m, 6H) ppm.

Step 2: trans-1,3-dimethylcyclopentane-1,3-dicarboxylic acid

A solution of compound trans-dimethyl 1,3-dimethylcyclopentane-1,3-dicarboxylate (950 mg, 4.43 mmol) and LiOH (319 mg, 13.30 mmol) in water (10 mL) and MeOH (10 mL) was stirred at r.t. for 48 hours. The solution was poured into 1 N HCl and extracted with EtOAc. The combined organic layers were dried over Na₂SO₄ and concentrated in vacuo to give the crude title compound. ¹H NMR (DMSO-d6 400 MHz): δ 12.14 (br. s., 4H), 2.17-2.05 (m, 2H), 1.98 (s, 2H), 1.55-1.39 (m, 2H), 1.23-1.11 (m, 6H) ppm.

Step 3: trans-methyl 3-(((3-chloropyrazin-2-yl)methyl)carbamoyl)-1,3-dimethylcyclopentanecarboxylate To a solution of DMF (0.1 mL, 1.291 mmol) and trans-1,3-dimethylcyclopentane-1,3-dicarboxylic acid (500 mg, 2.69 mmol) in DCM (20 mL) was added oxalyl dichloride (796 mg, 6.27 mmol) dropwise and stirred at room temperature for 16 hours. The solution was concentrated in vacuo and dissolved in DCM (20 mL). To the solution was added a solution of TEA (1.4 mL, 10.03 mmol) and (3-chloropyrazin-2-yl)methanamine (180 mg, 1.254 mmol) in 100 mL MeCN dropwise over 6 hours at 0° C. The solution was stirred at ROOM TEMPERATURE for another 1 hour and added MeOH (20 mL). The solution was stirred for 16 hours and added (diazomethyl)trimethylsilane (7.52 mL, 7.52 mmol). The solution was stirred for another 4 hours and added 30 mL 1N HCl. The solution was extracted with EtOAc and washed with water, brine, dried over Na₂SO₄ and purified by chromatography over silica gel (12 g) to give the title compound.

Step 4: trans-ethyl 3-(8-chloroimidazo[1,5-a]pyrazin-3-yl)-1,3-dimethylcyclopentane carboxylate A solution of pentachlorophosphorane (479 mg, 2.302 mmol) and compound trans-methyl 3-(((3-chloropyrazin-2-yl)methyl)carbamoyl)-1,3-dimethylcyclopentane carboxylate (250 mg, 0.767 mmol) in MeCN (30 mL) was stirred at 80° C. for 2 hours. The mixture was poured into 10% NaHCO₃ and extracted with EtOAc. The combined organic layer was washed with NaHCO₃ and water, dried over Na₂SO₄ and concentrated in vacuo to give the crude title compound.

Step 5: trans-ethyl-3-(1-bromo-8-chloroimidazo[1,5-a]pyrazin-3-yl)-3-dimethyl cyclo pentanecarboxylate To a solution of methyl 3-(8-chloroimidazo[1,5-a]pyrazin-3-yl)-1,3-dimethylcyclopentanecarboxylate (240 mg, 0.780 mmol) in MeCN (20 mL) was added NBS (139 mg, 0.780 mmol) and stirred for 1 hour. The solution was added 30% $NH_4Cl$ and extracted with EtOAc. The combined organic was washed with water, dried over $Na_2SO_4$ and concentrated in vacuo to give the crude title compound. MS: 388 (M+1).

Step 6: trans-methyl 3-(8-amino-1-bromoimidazo[1,5-a]pyrazin-3-yl)-1,3-dimethyl cyclo pentanecarboxylate A solution of compound trans-methyl 3-(1-bromo-8-chloroimidazo[1,5-a]pyrazin-3-yl)-1,3-dimethylcyclopentanecarboxylate (302 mg, 0.781 mmol) in AMMONIA (30 mL, 388 mmol) and i-PrOH (5 mL, 64.9 mmol) was stirred at 100° C. for 16 hours. The solution was extracted with EtOAc. The combined organic was washed with water, dried over $Na_2SO_4$ and concentrated in vacuo to give the title compound. MS: 367/369 (M+1).

Intermediate 12

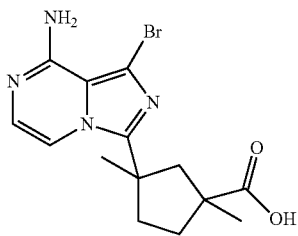 [SMILES: CC1(C(=O)O)CCC(C)(c2nc(Br)c3c(N)nccn23)C1]

3-(8-amino-1-bromoimidazo[1,5-a]pyrazin-3-yl)-1,3-dimethylcyclopentanecarboxylic acid Step 1: dimethyl cyclopentane-1,3-dicarboxylate Oxalyl dichloride (10.03 g, 79 mmol) was added to a solution of cyclopentane-1,3-dicarboxylic acid (5 g, 31.6 mmol) in dry MeOH (50 mL) under argon in an ice-water bath. The solution was allowed to warm to room temperature and stirred overnight. Volatiles were then removed under vacuum. The residue was taken up in EtOAc (2×50 mL) and the solution was washed with $NaHCO_3$ (2×50 mL) and brine (50 mL), dried over $MgSO_4$, filtered, and concentrated to give the title compound. $^1H$ NMR (400 MHz, $CDCl_3$): δ3.70 (s, 6H), 2.75-2.90 (m, 2H), 2.20-2.30 (m, 1H), 2.10-2.20 (m, 1H), 1.90-2.20 (m, 4H).

Step 2: dimethyl 1,3-dimethylcyclopentane-1,3-dicarboxylate

To a solution a solution of LDA (33.6 mL, 67.1 mmol) in 10 mL THF was added a solution of dimethyl cyclopentane-1,3-dicarboxylate (5 g, 26.9 mmol) in 10 mL THF under $N_2$ protection dropwise at −78° C. and stirred at −78° C. for 25 minutes. To the solution was added iodomethane (9.53 g, 67.1 mmol) dropwise and stirred at ROOM TEMPERATURE for another 16 hours. The solution was poured into water and extracted with EtOAc. The combined organic layers were washed with water and brine, dried over $Na_2SO_4$, concentrated in vacuo to give the title compound. $^1H$ NMR (400 MHz, $CDCl_3$): δ3.66 (major), 3.63 (minor) (s, 6H), 2.29-2.20 (m, 2H), 2.12 (s, 2H), 1.65-1.55 (m, 2H), 1.30-1.20 (m, 6H) ppm.

Step 3: 3-(methoxycarbonyl)-1,3-dimethylcyclopentanecarboxylic acid

A solution of KOH (1.309 g, 23.34 mmol) in methanol (20.0 mL) was added slowly over a period of 1.5 h to a refluxing solution of dimethyl 1,3-dimethylcyclopentane-1,3-dicarboxylate (5 g, 23.34 mmol) in methanol (30 mL). The mixture was kept refluxing for 1 h. The solvent was removed in vacuo, and the remaining oil was dissolved in water (40 mL). The solution was acidified with dilute HCl to pH 1. The mixture was extracted with dichloromethane (3×50 mL). The combined organic layers were concentrated to give the crude title compound. $^1H$ NMR (400 MHz, $CDCl_3$): δ 3.66 (major), 3.63 (minor) (s, 6H), 2.18-2.30 (m, 2H), 2.14 (major), 2.11 (minor) (s, 2H), 1.50-1.70 (m, 2H), 1.24-1.28 (m, 6H) ppm.

Step 4: methyl 3-(((3-chloropyrazin-2-yl)methyl)carbamoyl)-1,3-dimethylcyclopentanecarboxylate To a stirred solution of 3-(methoxycarbonyl)-1,3-dimethylcyclopentanecarboxylic acid (4 g, 19.98 mmol) in DMF (30 mL) was added HATU (11.39 g, 30.0 mmol) and N-ethyl-N-methylethanamine (3.48 g, 40.0 mmol). The solution was stirred at room temperature for 30 minutes. Then to this solution was added (3-chloropyrazin-2-yl)methanamine (3.44 g, 23.97 mmol). The mixture was stirred at room temperature overnight. The reaction mixture was purified by chromatography (petroleum ether: ethyl acetate=1:1) to give the title compound. MS: 326 (M+1).

Step 5: methyl 3-(8-chloroimidazo[1,5-a]pyrazin-3-yl)-1,3-dimethylcyclopentane carboxylate A solution of methyl 3-(((3-chloropyrazin-2-yl)methyl)carbamoyl)-1,3-dimethylcyclopentanecarboxylate (3 g, 9.21 mmol) and $PCl_5$ (5.75 g, 27.6 mmol) in acetonitrile (10 mL) was stirred at 80° C. for 2 hours and poured into 10% $NaHCO_3$. The mixture was washed with EtOAc. The combined organic was dried over $K_2CO_3$ and concentrated in vacuo. The residue was purified by column chromatography (petroleum ether: ethyl acetate=1:1) to give the crude title compound.

Step 6: methyl 3-(1-bromo-8-chloroimidazo[1,5-a]pyrazin-3-yl)-1,3-dimethylcyclopentanecarboxylate To a solution of methyl 3-(8-chloroimidazo[1,5-a]pyrazin-3-yl)-1,3-dimethylcyclopentanecarboxylate (200 mg, 0.650 mmol) in MeCN (10 mL) was added 1-bromopyrrolidine-2,5-dione (116 mg, 0.650 mmol) and stirred for 1 hour. The solution was added 30% $NH_4Cl$ and extracted with EtOAc. The combined organic layers were washed with water, dried over $Na_2SO_4$ and concentrated in vacuo to give crude title compound. MS: 387.9 (M+1).

Step 7: methyl 3-(8-amino-1-bromoimidazo[1,5-a]pyrazin-3-yl)-1,3-dimethylcyclopentanecarboxylate A solution of methyl 3-(1-bromo-8-chloroimidazo[1,5-a]pyrazin-3-yl)-1,3-dimethyl cyclopentanecarboxylate (100 mg, 0.259 mmol), ammonia hydrate (1.5 mL, 0.259 mmol) was added i-PrOH (1 mL). The reaction was stirred at 100°

C. for 16 hours. The reaction mixture was concentrated in vacuo, dissolved in EtOAc, washed with water. The combined organic layers were dried over Na$_2$SO$_4$ and concentrated in vacuo to give the title compound.

Step 8: 3-(8-amino-1-bromoimidazo[1,5-a]pyrazin-3-yl)-1,3-dimethylcyclopentane carboxylic acid To a solution methyl 3-(8-amino-1-bromoimidazo[1,5-a]pyrazin-3-yl)-1,3-dimethyl cyclopentanecarboxylate (200 mg, 0.545 mmol) in MeOH (10 mL) and water (5 mL) was added KOH (92 mg, 1.634 mmol). Then the reaction mixture was stirred at 80° C. for 16 h. The resulting aqueous solution was washed with EtOAc (50.0 mL), and then adjusted to pH=3.0 with HCl aqueous. The combined organic layers were dried over anhydrous Na$_2$SO$_4$, and concentrated in vacuum to give the title compound. MS: 387.9 (M+1).

Intermediate 13A & 13B

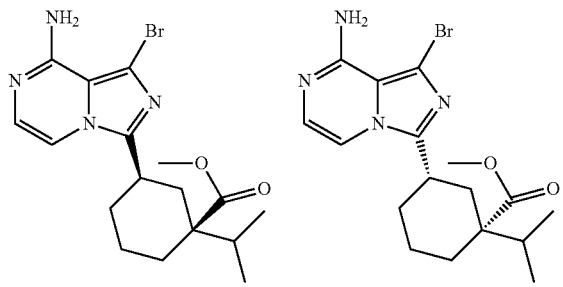 [SMILES: COC(=O)[C@@]1(C(C)C)CCC[C@@H](c2nc(Br)c3c(N)nccn23)C1 ; COC(=O)[C@]1(C(C)C)CCC[C@H](c2nc(Br)c3c(N)nccn23)C1]

(1S,3R)-methyl 3-(8-amino-1-bromoimidazo[1,5-a]pyrazin-3-yl)-1-isopropylcyclohexanecarboxylate and (1R,3S)-methyl 3-(8-amino-1-bromoimidazo[1,5-a]pyrazin-3-yl)-1-isopropylcyclohexanecarboxylate Step 1: dimethyl 1-isopropylcyclohexane-1,3-dicarboxylate To a solution of dimethyl cyclohexane-1,3-dicarboxylate (5.2 g, 26 mmol) in THF (60 mL) was added HMPT (18.6 g, 104 mmol) followed by LDA (14.3 mL, 28.6 mmol) at −70° C. The resulting mixture was stirred at −70° C. for 1 h. 2-iodopropane (8.8 g, 52 mmol) was then added dropwise, and the mixture was allowed to warm to room temperature and stirred for further 4 hrs. The mixture was quenched with saturated NH$_4$Cl solution and extracted with EA. The organic layer was dried and concentrated, the residue was purified by column chromatography on silica gel eluted with PE/EA=10/1 to give dimethyl 1-isopropylcyclohexane-1,3-dicarboxylate as solid.
$^1$H NMR (400 MHz, CDCl$_3$) δ ppm: 0.88 (dd, J=6.65, 3.13 Hz, 6H), 1.10-1.33 (m, 4H), 1.70-1.79 (m, 2H), 1.87-1.96 (m, 1H), 2.06-2.18 (m, 1H), 2.29-2.49 (m, 2H), 3.68 (d, J=7.83 Hz, 6H).

Step 2: 3-isopropyl-3-(methoxycarbonyl)cyclohexanecarboxylic acid

To a solution of dimethyl 1-isopropylcyclohexane-1,3-dicarboxylate (4.5 g, 18.6 mmol) in THF/MeOH/H$_2$O (30 mL/30 mL/10 mL) was added LiOH.H$_2$O (2.3 g, 55.8 mmol). The mixture was stirred at room temperature for 4 hrs. The reaction mixture was acidified by 1 M HCl, and extracted with EA. The organic layer was dried and concentrated, and the residue was used in next step directly.

Step 3: methyl 3-(((3-chloropyrazin-2-yl)methyl)carbamoyl)-1-isopropylcyclohexanecarboxylate To a solution of 3-isopropyl-3-(methoxycarbonyl)cyclohexanecarboxylic acid (4.4 g, 19.3 mmol) in THF (100 mL) was added (3-chloropyrazin-2-yl)methanamine hydrochloride (5.2 g, 28.9 mmol), HATU (11 g, 28.9 mmol) and TEA (11.7 g, 115.8 mmol). The mixture was stirred at room temperature overnight. The reaction mixture was diluted with EA and water, the organic layer was dried and concentrated. The residue was purified by column chromatography on silica gel eluted with PE/THF=5/1 to give methyl 3-(((3-chloropyrazin-2-yl)methyl)carbamoyl)-1-isopropylcyclohexanecarboxylate.
$^1$H NMR (400 MHz, CDCl$_3$) δ ppm: 0.86 (t, J=6.65 Hz, 6H), 1.16-1.32 (m, 2H), 1.36-1.47 (m, 2H), 1.69-1.87 (m, 3H), 2.07-2.16 (m, 1H), 2.22-2.42 (m, 2H), 3.69 (s, 3H), 4.56-4.76 (m, 2H), 6.79 (s, 1H), 8.31 (d, J=2.74 Hz, 1H), 8.45 (d, J=2.74 Hz, 1H).

Step 4: methyl 3-(8-chloroimidazo[1,5-a]pyrazin-3-yl)-1-isopropylcyclohexanecarboxylate To a solution of methyl 3-(((3-chloropyrazin-2-yl)methyl)carbamoyl)-1-isopropylcyclohexanecarboxylate (3 g, 8.5 mmol) in MeCN (80 mL) was added PCl$_5$ (3.5 g, 17 mmol). The mixture was stirred at 70° C. for 3 hrs. The reaction solution was diluted with DCM and aqueous NaHCO$_3$. The organic layer was dried and concentrated. The residue was purified by column chromatography on silica gel eluted with PE/THF=20/1 to methyl 3-(8-chloroimidazo[1,5-a]pyrazin-3-yl)-1-isopropylcyclohexanecarboxylate. MS=336 (M+1)$^+$ Step 5: methyl 3-(1-bromo-8-chloroimidazo[1,5-a]pyrazin-3-yl)-1-isopropylcyclo hexanecarboxylate To a solution of methyl 3-(8-chloroimidazo[1,5-a]pyrazin-3-yl)-1-isopropylcyclohexanecarboxylate (2.6 g, 7.8 mmol) in MeCN (30 ml) was added a solution of NBS (1.5 g, 8.5 mmol) in MeCN (10 ml). The mixture was stirred at room temperature for 1 hr.
The reaction mixture was treated with EA and water, the organic layer was dried and concentrated. The residue was purified by column chromatography on silica gel eluted with PE/THF=20/1 to give methyl 3-(1-bromo-8-chloroimidazo[1,5-a]pyrazin-3-yl)-1-isopropylcyclohexanecarboxylate. MS: 416 (M+1).

Step 6: (1S,3R)-methyl 3-(8-amino-1-bromoimidazo[1,5-a]pyrazin-3-yl)-1-isopropylcyclohexanecarboxylate and (1R,3S)-methyl 3-(8-amino-1-bromoimidazo[1,5-a]pyrazin-3-yl)-1-isopropylcyclohexanecarboxylate In 100 mL seal tube, a solution of methyl 3-(1-bromo-8-chloroimidazo[1,5-a]pyrazin-3-yl)-1-isopropylcyclohexanecarboxylate (2 g, 4.8 mmol) in NH$_3$/i-PrOH (20 mL) was added, and the mixture was stirred at 100° C. overnight. The reaction mixture was concentrated and the residue was purified by column chromatography on silica gel eluted with DCM/THF=20/1 to give methyl 3-(8-amino-1-bromoimidazo[1,5-a]pyrazin-3-yl)-1-isopropylcyclohexanecarboxylate. The product was separated by SFC to give (1S,3R)-methyl 3-(8-amino-1-bromoimidazo[1,5-a]pyrazin-3-yl)-1-isopropylcyclohexanecarboxylate and (1R,3S)-methyl 3-(8-amino-1-bromoimidazo[1,5-a]pyrazin-3-yl)-1-isopropylcyclohexanecarboxylate.

¹H NMR (400 MHz, CD₃OD) δ ppm 0.88 (dd, J=6.85, 2.54 Hz, 6H), 1.31-1.46 (m, 3H), 1.61-1.96 (m, 4H), 2.16-2.36 (m, 2H), 3.05-3.17 (m, 1H), 3.77 (s, 3H), 6.97 (d, J=8.0 Hz, 1H), 7.47 (d, J=8.0 Hz, 1H) ppm.

Intermediate 14

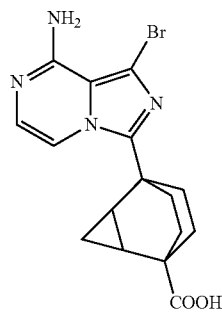 [SMILES: Nc1nccn2c(C34CCC(C(=O)O)(CC3)C3CC34)nc(Br)c12]

5-(8-amino-1-(2-ethoxy-4-((4-(trifluoromethyl)pyridin-2-yl)carbamoyl)phenyl)imidazo[1,5-a]pyrazin-3-yl)tricyclo[3.2.2.0²,⁴]nonane-1-carboxylic acid Step 1: dimethyl bicyclo[2.2.2]oct-2-ene-1,4-dicarboxylate To a solution of bicyclo[2.2.2]oct-2-ene-1,4-dicarboxylic acid (2 g, 10.19 mmol) in MeOH (20 ml) was added SOCl₂ (2.98 ml, 40.8 mmol), then the mixture was stirred at 70° C. for 2 h. The mixture was cooled to room temperature, adjusted to basic with aq. NaHCO₃ (ph=8) and extracted with ethyl acetate (100 mL×3). The combined organic layers were washed with brine (100 mL), dried over anhydrous sodium sulfate, concentrated to afford crude product which was purified on silica gel column chromatograph (PE: EA=100%~70%) to give title compound.

¹H NMR (400 MHz, CDCl₃) δ=6.51 (s, 2H), 3.76 (s, 6H), 1.93 (d, J=7.0 Hz, 4H), 1.50 (d, J=7.0 Hz, 4H) ppm.

Step 2: dimethyl tricyclo[3.2.2.0²,⁴]nonane-1,5-dicarboxylate

To a solution of dimethyl bicyclo[2.2.2]oct-2-ene-1,4-dicarboxylate (1 g, 4.46 mmol) in CH₂Cl₂ (2 ml) added diethylzinc (22.30 ml, 22.30 mmol) at 0° C. under nitrogen protection. The mixture was stirred at 0° C. for 15 mins, and a solution of diiodomethane (3.60 ml, 44.6 mmol) was added. The reaction mixture was stirred at 20° C. for 12 hours. The mixture was diluted with DCM (5 mL) and 1N HCl (10 mL), extracted with DCM (10 mL×3). The combined organic layers were washed with brine (10 mL) dried over anhydrous sodium sulfate and evaporated to give title compound. ¹H NMR (400 MHz, CDCl₃) δ=3.70 (s, 5H), 1.95 (d, J=6.7 Hz, 2H), 1.82 (d, J=7.4 Hz, 2H), 1.58 (d, J=5.9 Hz, 4H), 1.33 (dd, J=3.5, 7.4 Hz, 2H), 0.73-0.67 (m, 1H), 0.50 (q, J=7.4 Hz, 1H) ppm.

Step 3: 5-(methoxycarbonyl)tricyclo[3.2.2.0²,⁴]nonane-1-carboxylic acid

To a solution of dimethyl tricyclo[3.2.2.0²,⁴]nonane-1,5-dicarboxylate (800 mg, 3.36 mmol) in anhydrous THF (1 ml) was added a solution of NaOH (132 mg, 3.29 mmol) in MeOH (2 ml). The mixture was stirred at 15° C. for 12 hours. The mixture was adjusted acid to pH=2 with 2M HCl and the mixture was extracted with EA (10 mL×3), the combined organic layers were washed with brine (10 mL), dried over sodium sulfate, filtered and concentrated to give 5-(methoxycarbonyl)tricyclo[3.2.2.0²,⁴]nonane-1-carboxylic acid. ¹H NMR (400 MHz, CDCl₃) δ=3.73-3.63 (m, 3H), 2.01-1.89 (m, 3H), 1.88-1.76 (m, 2H), 1.67-1.48 (m, 4H), 1.41-1.27 (m, 2H), 0.74-0.64 (m, 1H), 0.56-0.44 (m, 1H) ppm.

Step 4: methyl 5-(((3-chloropyrazin-2-yl)methyl)carbamoyl)tricyclo[3.2.2.0²,⁴]nonane-1-carboxylate To a solution of 5-(methoxycarbonyl)tricyclo[3.2.2.0²,⁴]nonane-1-carboxylic acid (440 mg, 1.962 mmol) in anhydrous CH₂Cl₂ (8 ml) was added Et₃N (0.820 ml, 5.89 mmol), (3-chloropyrazin-2-yl)methanamine, HCl (424 mg, 2.354 mmol) and HATU (895 mg, 2.354 mmol). The reaction mixture was stirred at 15° C. for 12 hours. The reaction was quenched by the addition of water (10 mL), then it was extracted with DCM (20 mL×3), the combined organic layers were washed with brine (20 mL), dried over sodium sulfate, filtered and concentrated to afford the crude product, which was purified on silica gel column chromatograph (PE/EA=100%~50%) to give methyl 5-(((3-chloropyrazin-2-yl)methyl)carbamoyl)tricyclo[3.2.2.0²,⁴]nonane-1-carboxylate. ¹H NMR (400 MHz, CDCl₃) δ=8.47 (d, J=2.5 Hz, 1H), 8.33 (s, 1H), 4.70 (d, J=4.8 Hz, 2H), 3.72 (s, 3H), 2.08-1.83 (m, 4H), 1.68-1.59 (m, 4H), 1.42 (br. s., 1H), 1.25 (d, J=7.3 Hz, 1H), 0.84-0.78 (m, 1H), 0.68-0.61 (m, 1H) ppm.

Step 5: methyl 5-(8-chloroimidazo[1,5-a]pyrazin-3-yl)tricyclo[3.2.2.0²,⁴]nonane-1-carboxylate To a solution of methyl 5-(((3-chloropyrazin-2-yl)methyl)carbamoyl)tricyclo[3.2.2.0²,⁴]nonane-1-carboxylate (550 mg, 1.572 mmol) in MeCN (5 ml) was added pentachlorophosphorane (655 mg, 3.14 mmol) at 0° C. The mixture was allowed to warm to 10° C. and for 4 hours. The mixture was added to Sat. NH₄Cl (20 mL) dropwise at 0° C. and extracted with ethyl acetate (20 mL×3). The combined organic layers were washed with brine (20 mL) dried over anhydrous sodium sulfate and evaporated to give crude product which was purified on silica gel column chromatograph (PE/EA=100%~60%) to give methyl 5-(8-chloroimidazo[1,5-a]pyrazin-3-yl)tricyclo[3.2.2.0²,⁴]nonane-1-carboxylate. ¹H NMR (400 MHz, CDCl₃) δ=8.30 (d, J=4.7 Hz, 1H), 7.76 (s, 1H), 7.28 (d, J=5.1 Hz, 1H), 3.72 (s, 3H), 2.63-2.53 (m, 1H), 2.28-2.18 (m, 1H), 2.15-1.96 (m, 3H), 1.84-1.61 (m, 4H), 1.51-1.39 (m, 1H), 1.18 (br. s., 1H), 1.05-0.98 (m, 1H), 0.88-0.79 (m, 1H) ppm.

Step 6: methyl 5-(1-bromo-8-chloroimidazo[1,5-a]pyrazin-3-yl)tricyclo[3.2.2.0²,⁴]nonane-1-carboxylate A mixture of methyl 5-(8-chloroimidazo[1,5-a]pyrazin-3-yl)tricyclo[3.2.2.0²,⁴]nonane-1-carboxylate (120 mg, 0.362 mmol) in DMF (2 ml) was added NBS (77 mg, 0.434 mmol).

The mixture was stirred at 15° C. for 1 hour. The reaction mixture was poured into water, filtered and the cake was washed by water 3 times. The cake was dissolved in ethyl acetate (10 mL), dried over anhydrous sodium sulfate and evaporated to give methyl 5-(1-bromo-8-chloroimidazo[1,5-a]pyrazin-3-yl)tricyclo[3.2.2.02,4]nonane-1-carboxylate. MS: 412 (M+1).

Step 7: 5-(8-amino-1-bromoimidazo[1,5-a]pyrazin-3-yl)tricyclo[3.2.2.02,4]nonane-1-carboxylic acid A mixture of methyl 5-(1-bromo-8-chloroimidazo[1,5-a]pyrazin-3-yl)tricyclo[3.2.2.02,4]nonane-1-carboxylate (130 mg, 0.317 mmol) in ammonia, H$_2$O (2 ml, 13.47 mmol) and 2-Propanol (2 ml) in a sealed tube. The mixture was stirred at 100° C. for 12 hours. The reaction mixture was cooled to 15° C. and concentrated to afford 5-(8-amino-1-bromoimidazo[1,5-a]pyrazin-3-yl)tricyclo[3.2.2.02,4]nonane-1-carboxylic acid. MS: 377 (M+1).

Intermediate 15E1 & 15E2

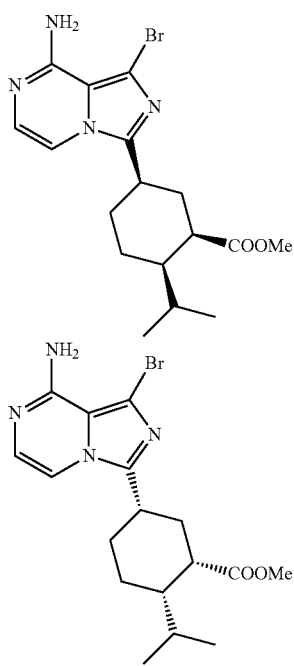

(1R,2R,5R)-methyl 5-(8-amino-1-bromoimidazo[1,5-a]pyrazin-3-yl)-2-isopropylcyclohexanecarboxylate and (1S,2S,5S)-methyl 5-(8-amino-1-bromoimidazo[1,5-a]pyrazin-3-yl)-2-isopropylcyclohexanecarboxylate Step 1: dimethyl 4-bromoisophthalate A mixture of 4-bromoisophthalic acid (20 g, 82 mmol) in 4 N HCl/MeOH (300 mL) was stirred at 60° C. for 3 hours. The mixture was concentrated and the residue was purified by column chromatography on silica gel (PE/EA=10/1) to afford dimethyl 4-bromoisophthalate.

$^1$H NMR (400 MHz, DMSO-d$_6$) δ ppm 8.30 (d, J=1.96 Hz, 1H), 8.00 (dd, J=8.22, 1.96 Hz, 1H), 7.94 (d, J=8.22 Hz, 1H), 3.93 (d, J=5.87 Hz, 6H).

Step 2: dimethyl 4-(prop-1-en-2-yl)isophthalate

A mixture of dimethyl 4-bromoisophthalate (15 g, 54.9 mmol), potassium trifluoro(prop-1-en-2-yl)borate (9.75 g, 65.9 mmol), PdCl$_2$(dppf)-DCM (4.49 g, 5.49 mmol) and Na$_2$CO$_3$ (14.55 g, 137 mmol) in dioxane (100 ml) and water (10.00 ml) was stirred under N$_2$ protected at 90° C. for 2 hours. The mixture was filtered and filtrate was concentrated. The residue was purified by column chromatography on silica gel (PE/EA=10/1) to afford dimethyl 4-(prop-1-en-2-yl)isophthalate.

$^1$H NMR (400 MHz, CD$_3$OD) δ ppm 8.36 (d, J=2.01 Hz, 1H), 8.11 (dd, J=8.03, 1.00 Hz, 1H), 7.41 (d, J=8.03 Hz, 1H), 5.16 (t, J=1.51 Hz, 1H), 4.85 (s, 1H), 3.94 (s, 3H), 3.88 (s, 3H), 2.10 (s, 3H).

Step 3: 3-(methoxycarbonyl)-4-(prop-1-en-2-yl)benzoic acid

To a solution of dimethyl 4-(prop-1-en-2-yl)isophthalate (12 g, 51.2 mmol) in THF (100 ml) and MeOH (100 ml) was added KOH (2.87 g, 51.2 mmol) at 0° C. The mixture was stirred at 25° C. for 16 hours. The mixture was adjusted to pH=6 with 1 N HCl aqueous. The mixture was extracted with EA (200 mL×3). The EA layer was washed with NaHCO$_3$ saturated solution. The aqueous solution was adjusted to pH=6 with 1 N HCl aqueous, and the resulting solution was extracted with EA (200 mL×3). Organic layer was washed with brine and dried over anhydrous Na$_2$SO$_4$. The mixture was filtered and concentrated to afford 3-(methoxycarbonyl)-4-(prop-1-en-2-yl)benzoic acid.

$^1$H NMR (400 MHz, DMSO-d$_6$) δ ppm 8.20 (d, J=1.56 Hz, 1H), 8.03 (dd, J=8.02, 1.76 Hz, 1H), 7.41 (d, J=7.83 Hz, 1H), 5.12 (s, 1H), 4.80 (s, 1H), 3.78 (s, 3H), 2.00 (s, 3H).

Step 4: 4-isopropyl-3-(methoxycarbonyl)cyclohexanecarboxylic acid

A mixture of 3-(methoxycarbonyl)-4-(prop-1-en-2-yl)benzoic acid (11 g, 49.9 mmol) and PtO$_2$ (4.54 g, 19.98 mmol) in AcOH (500 ml) was hydrogenated under 35 atm at 80° C. for 40 hours. The mixture was filtered and the filtrate was concentrated to afford 4-isopropyl-3-(methoxycarbonyl)cyclohexanecarboxylic acid as crude product, which was used in the next step directly.

Step 5: methyl 5-(((3-chloropyrazin-2-yl)methyl)carbamoyl)-2-isopropylcyclohexanecarboxylate To a solution of 4-isopropyl-3-(methoxycarbonyl)cyclohexanecarboxylic acid (11 g, 48.2 mmol) and TEA (12.19 g, 120 mmol) in THF (200 ml) was added isopropyl carbonochloridate (7.09 g, 57.8 mmol) at 0° C. The mixture was stirred at 20° C. for 1 hour. (3-chloropyrazin-2-yl)methanamine hydrochloride (10.41 g, 57.8 mmol) was added to above solution. The mixture was stirred at 20° C. for another 2 hours. The mixture was treated with water (200 mL) and EA (200 mL). The organic layer was washed with brine, dried, filtered and concentrated. The residue was purified by silica gel column chromatography (PE/THF=3/1) to afford methyl 5-(((3-chloropyrazin-2-yl)methyl)carbamoyl)-2-isopropylcyclohexanecarboxylate as solid. MS=354.0 (M+1)

Step 6: methyl 5-(8-chloroimidazo[1,5-a]pyrazin-3-yl)-2-isopropylcyclohexanecarboxylate A solution of methyl 5-(((3-chloropyrazin-2-yl)methyl)carbamoyl)-2-isopropylcyclohexanecarboxylate (4.3 g, 12.15 mmol) and $PCl_5$ (12.65 g, 60.8 mmol) in MeCN (100 ml) was stirred at 60° C. for 2 hours. The mixture was poured into saturated $NaHCO_3$ solution (250 mL), and the resulting mixture was extracted with EA (250 mL). The EA layer was separated, washed with water, brine and dried over $Na_2SO_4$, filtered and the solvent was evaporated under reduced pressure. The residue was purified by column chromatography on silica gel eluting with PE/THF=5/1 to give methyl 5-(8-chloroimidazo[1,5-a]pyrazin-3-yl)-2-isopropylcyclohexanecarboxylate.
MS=336.1 (M+1)

Step 7: methyl 5-(1-bromo-8-chloroimidazo[1,5-a]pyrazin-3-yl)-2-isopropylcyclohexane carboxylate A solution of methyl 5-(8-chloroimidazo[1,5-a]pyrazin-3-yl)-2-isopropylcyclohexanecarboxylate (3.3 g, 9.83 mmol) and NBS (1.749 g, 9.83 mmol) in MeCN (200 ml) was stirred at 20° C. for 30 min. The mixture was treated with EA (200 mL) and water (200 mL). The organic layer was separated, washed with water, brine and dried over $Na_2SO_4$, filtered and the solvent was evaporated under reduced pressure. The residue was purified by column chromatography on silica gel eluting with PE/THF=3/1 to give methyl 5-(1-bromo-8-chloroimidazo[1,5-a]pyrazin-3-yl)-2-isopropylcyclohexanecarboxylate as solid. MS=416.1 (M+1).

Step 8: methyl 5-(8-amino-1-bromoimidazo[1,5-a]pyrazin-3-yl)-2-isopropylcyclohexane carboxylate A solution of methyl 5-(1-bromo-8-chloroimidazo[1,5-a]pyrazin-3-yl)-2-isopropylcyclohexanecarboxylate (3.6 g, 8.68 mmol) in ammonia/i-PrOH (60 ml, 240 mmol) was stirred at 90° C. for 16 hours in a 100 mL of sealed tube. The mixture was filtered and concentrated. The residue was purified by column chromatography on silica gel eluting with PE/THF=3/1 to give methyl 5-(8-amino-1-bromoimidazo[1,5-a]pyrazin-3-yl)-2-isopropylcyclohexanecarboxylate.

Step: 9: (1R,2R,5R)-methyl 5-(8-amino-1-bromoimidazo[1,5-a]pyrazin-3-yl)-2-isopropylcyclohexanecarboxylate and (1S,2S,5S)-methyl 5-(8-amino-1-bromoimidazo[1,5-a]pyrazin-3-yl)-2-isopropylcyclohexanecarboxylate Methyl 5-(8-amino-1-bromoimidazo[1,5-a]pyrazin-3-yl)-2-isopropylcyclohexanecarboxylate was separated by SFC to give (1R,2R,5R)-methyl 5-(8-amino-1-bromoimidazo[1,5-a]pyrazin-3-yl)-2-isopropylcyclohexanecarboxylate $^1$H NMR (400 MHz, $CD_3OD$) δ ppm 7.50 (d, J=5.09 Hz, 1H), 6.92 (d, J=5.09 Hz, 1H), 3.60 (s, 3H), 3.09-3.22 (m, 1H), 2.69-2.80 (m, 1H), 2.07-2.16 (m, 1H), 1.91-2.06 (m, 5H), 1.76-1.89 (m, 4H), 1.57-1.74 (m, 2H), 0.96 (d, J=6.65 Hz, 3H), 0.81 (d, J=6.26 Hz, 3H).

(1S,2S,5S)-methyl 5-(8-amino-1-bromoimidazo[1,5-a]pyrazin-3-yl)-2-isopropylcyclohexanecarboxylate $^1$H NMR (400 MHz, $CD_3OD$) δ ppm 7.50 (d, J=5.09 Hz, 1H), 6.91 (d, J=5.09 Hz, 1H), 3.60 (s, 3H), 3.05-3.22 (m, 1H), 2.68-2.82 (m, 1H), 2.11 (dd, J=13.69, 3.52 Hz, 1H), 1.91-2.06 (m, 4H), 1.76-1.89 (m, 3H), 1.56-1.74 (m, 2H), 0.95 (d, J=6.26 Hz, 3H), 0.80 (d, J=0.26 Hz, 3H).

Intermediate 16

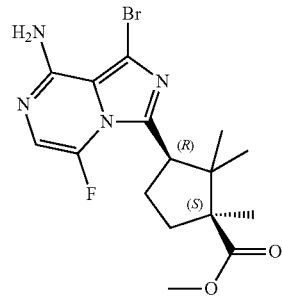

(1S,3R)-methyl 3-(8-amino-1-bromo-5-fluoroimidazo[1,5-a]pyrazin-3-yl)-1,2,2-tri methylcyclopentanecarboxylate

Step 1: (1S,3R)-methyl 3-(8-amino-1-bromo-5-fluoro-6-methoxy-5,6-dihydroimidazo[1,5-a]pyrazin-3-yl)-1,2,2-trimethylcyclopentanecarboxylate Selectfluor (718 mg, 2.026 mmol) was added slowly to a stirred solution of (1S, 3R)-methyl 3-(8-amino-1-bromoimidazo[1,5-a]pyrazin-3-yl)-1,2,2-trimethylcyclopentanecarboxylate (515 mg, 1.351 mmol) in MeOH (10 mL) and acetonitrile (10 mL). The mixture was stirred at 12° C. for 3 h. The reaction mixture was concentrated to remove solvent, then added water. The mixture was washed with 2-methoxy-2-methylpropane, the water layer was added $NaHCO_3$ to adjust to pH=7, and then extracted with DCM. The organic layer was dried over $Na_2SO_4$, concentrated to give the title compound. $^1$H NMR (400 MHz, $CDCl_3$): δ6.23-5.90 (m, 1H), 5.11-5.02 (m, 1H), 3.70 (s, 3H), 3.50-3.42 (m, 3H), 3.34-3.15 (m, 1H), 2.83-2.72 (m, 1H), 2.58-2.42 (m, 1H), 2.12-2.00 (m, 1H), 1.67-1.55 (m, 1H), 1.37-1.28 (m, 3H), 1.13 (s, 3H), 0.83-0.78 (m, 3H) ppm.

Step 2: (1S,3R)-methyl 3-(8-amino-1-bromo-5-fluoroimidazo[1,5-a]pyrazin-3-yl)-1,2,2-trimethylcyclopentanecarboxylate To a suspension of (1S, 3R)-methyl 3-(8-amino-1-bromo-5-fluoro-6-methoxy-5,6-dihydroimidazo[1,5-a]pyrazin-3-yl)-1,2,2-trimethylcyclopentanecarboxylate (700 mg, 1.623 mmol) and $Cs_2CO_3$ (5.29 g, 16.23 mmol) in acetonitrile (6 mL) was stirred at 90° C. for 30 min in a microwave reactor. The mixture was filtered and added water, extracted with EtOAc. The organic layer was dried over anhydrous sodium sulfate, purified with silica gel (12 g, DCM/MeOH 10:1) to give the title compound. MS: 401.0 (M+1).

Intermediate 17

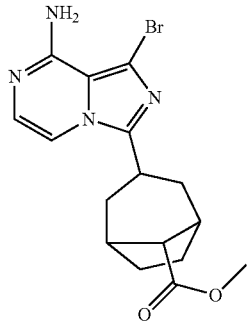 [SMILES: COC(=O)C1C2CCC1CC(c1nc(Br)c3c(N)nccn13)C2]

methyl 3-(8-amino-1-bromoimidazo[1,5-a]pyrazin-3-yl)bicyclo[3.2.1]octane-8-carboxylate Step 1: ethyl 8-oxobicyclo[3.2.1]octane-3-carboxylate To a solution of 1-(cyclopent-1-en-1-yl)pyrrolidine (68 g, 496 mmol) and triethylamine (150 g, 1489 mmol) in acetonitrile (1.09 L, dried over calcium hydride) was added a solution of ethyl 2-(bromomethyl)acrylate (96 g, 496 mmol) in dry acetonitrile (1.04 L) dropwise. Heat was generated upon addition and the solution turned reddish brown, a solid was precipitated. The reaction mixture was heated at 90° C. for 3.5 hours. Hydrolysis of the iminiumion was accomplished by the addition of 150 ml of 5% aqueous acetic acid followed by a 0.5 hour refluxing period. The reaction mixture was cooled and an equal volume of water was added. The aqueous mixture was then extracted several times with ether and the combined organic layers were washed with 5% aqueous hydrochloric acid, saturated aqueous sodium bicarbonate, and saturated aqueous sodium chloride. The resulting ethereal solution was dried over anhydrous magnesium sulfate. Filtration and evaporation of the ether gave the crude which was purified by column chromatography on silica gel petroleum ether/EtOAc from 15/1 to 9/1 to get the title product. $^1$HNMR (400 MHz, CD$_3$OD): δ 8.13-8.09 (m, 1H), 7.32-7.31 (m, 1H), 3.67 (s, 3H), 2.50-2.46 (m, 1H), 2.18-2.13 (m, 2H), 1.95-1.91 (m, 2H), 1.86-1.81 (m, 1H), 1.76-1.68 (m, 1H), 1.56-1.54 (m, 1H), 1.21 (s, 3H) ppm.

Step 2: 8-oxobicyclo[3.2.1]octane-3-carboxylic acid

To a solution of ethyl 8-oxobicyclo[3.2.1]octane-3-carboxylate (30.5 g, 156 mmol) in MeOH/H$_2$O (3:1, 200 mL) was added LiOH (29.9 g, 1245 mmol). The reaction mixture was stirred at 12° C. for 2 hours. Volatiles were removed under vacuum, then the mixture was adjusted to pH=3.0 with a solution of 1N HCl, extracted with ethyl acetate and concentrated to give the crude title compound.

Step 3: benzyl 8-oxobicyclo[3.2.1]octane-3-carboxylate

To a solution of 8-oxobicyclo[3.2.1]octane-3-carboxylic acid (21.3 g, 126 mmol) in DMF (265 mL) was added K$_2$CO$_3$ (17.5 g, 126 mmol) at 0° C. and stirred at the same temperature for 20 minutes, then (bromomethyl)benzene (23.8 g, 139 mmol) was added dropwise. The reaction mixture was allowed to warm to 12° C. and stirred for 16 hours. The reaction mixture was added water and extracted with ethyl acetate. The extracts were washed with brine, dried over Na$_2$SO$_4$ and concentrated to give the crude product. The crude product was purified by column chromatography on silica gel petroleum ether/EtOAc from 15/1 to 9/1 to give the title compound. $^1$H NMR (400 MHz, CDCl$_3$): δ 7.39-7.32 (m, 5H), 5.11 (s, 1H), 3.09-3.00 (m, 1H), 2.29-2.28 (m, 2H), 2.21-2.18 (m, 4H), 2.01-2.00 (m, 2H), 1.80-1.78 (m, 2H) ppm.

Step 4: benzyl 8-(methoxymethylene)bicyclo[3.2.1]octane-3-carboxylate

To a solution of (methoxymethyl)triphenylphosphonium chloride (9.98 g, 29.1 mmol) in THF (100 mL) was added LiHMDS (60.1 mL, 60.1 mmol) at −78° C. Then the reaction mixture was allowed to warm to 15° C. and stirred for 1 hour. Then the reaction was cooled to −78° C. and benzyl 8-oxobicyclo[3.2.1]octane-3-carboxylate (4 g, 15.49 mmol) was added. The mixture was stirred at −78° C. for another 2 hours, then warmed to room temperature and quenched by NH$_4$Cl solution. Then the mixture was extracted with ethyl acetate and washed with brine. The organic layer was dried over Na$_2$SO$_4$ and concentrated under reduced pressure to afford the crude product, which was purified by combi-flash (petroleum ether in EtOAc from 0% to 5%, R$_f$=0.68) to get the title product. $^1$H NMR (400 MHz, CD$_3$OD): δ 7.42-7.23 (m, 5H), 5.83 (s, 1H), 5.07 (s, 2H), 3.51 (s, 3H), 2.99 (brs, 1H), 2.83 (tt, J=5.8, 12.0 Hz, 1H), 2.48 (brs, 1H), 1.93-1.85 (m, 1H), 1.84-1.78 (m, 1H), 1.75-1.61 (m, 4H), 1.61-1.54 (m, 3H) ppm.

Step 5: 3-benzyl 8-methyl icycle[3.2.1]octane-3,8-dicarboxylate

To a solution of benzyl 8-(methoxymethylene)icycle [3.2.1]octane-3-carboxylate (14.6 g, 51.04 mmol) in CH$_2$Cl$_2$ (160 mL) was added PCC (32.9 g, 153.1 mmol). Then the reaction was stirred at 16° C. for 2 h. PCC (11 g, 51 mmol) was added. The reaction was stirred at 16° C. for 1 h. The mixture was filtered. The filtrate was washed with water and the solid was washed with ethyl acetate. The organic layer was dried over Na$_2$SO$_4$ and concentrated to give the crude product, which was purified by column chromatography on silica gel (petroleum ether/EtOAc from 15/1 to 9/1) to give the title compound. $^1$H NMR (400 MHz, CDCl$_3$): δ 7.35-7.33 (m, 5H), 5.08 (s, 2H), 3.71 (s, 3H), 2.69 (s, 1H), 2.58 (s, 2H), 2.67-2.64 (m, 1H), 2.53-2.52 (m, 2H), 1.95-1.88 (m, 2H), 1.80-1.78 (m, 2H), 1.71-1.67 (m, 2H), 1.56-1.54 (m, 2H) ppm.

Step 6: 8-(methoxycarbonyl) icycle[3.2.1]octane-3-carboxylic acid

To a solution of 3-benzyl 8-methyl icycle[3.2.1]octane-3,8-dicarboxylate (1300 mg, 4.30 mmol) in MeOH (20 mL) was added Pd/C (80 mg, 0.676 mmol). Then the reaction mixture was purged with hydrogen for three times and stirred at 25° C. for 4 hours under 40 psi of H$_2$. The reaction mixture was filtered and concentrated under reduced pressure to give the title compound.

$^1$HNMR (400 MHz, CDCl$_3$): δ 3.65 (s, 3H), 2.66-2.52 (m, 1H), 2.47 (d, J=4.7 Hz, 2H), 1.89-1.79 (m, 2H), 1.77-1.68 (m, 2H), 1.66-1.55 (m, 2H), 1.50 (d, J=8.2 Hz, 2H) ppm.

Step 7: methyl 3-(((3-chloropyrazin-2-yl)methyl) carbamoyl)bicyclo[3.2.1]octane-8-carboxylate A 30 vial was charged with 8-(methoxycarbonyl)bicyclo [3.2.1]octane-3-carboxylic acid (830 mg, 3.91 mmol), HATU (1784 mg, 4.69 mmol), TEA (1.635 mL, 11.73 mmol) and DCM (20 mL). The mixture was stirred at 30° C. for 30 minutes. Then (3-chloropyrazin-2-yl)methanamine hydrochloride (845 mg, 4.69 mmol) was added, the resulting mixture was stirred at 30° C. for 16 hours. The reaction mixture was diluted with EtOAc (50 mL) and washed with brine (50 mL×3). The organic layer was evaporated to dryness and the residue was purified via combi flash (EtOAc in petroleum from 0% to 50%) to give the title compound. $^1$H NMR (400 MHz, CDCl$_3$): δ 8.46 (d, J=2.0 Hz, 1H), 8.32 (brs, 1H), 6.85 (brs, 1H), 4.69-4.59 (m, 2H), 3.72 (s, 3H), 2.70-2.50 (m, 4H), 2.05-1.93 (m, 2H), 1.89-1.77 (m, 2H), 1.70 (m, 2H), 1.65-1.56 (m, 2H) ppm.

Step 8: methyl 3-(8-chloroimidazo[1,5-a]pyrazin-3-yl)bicyclo[3.2.1]octane-8-carboxylate To a solution of methyl 3-(((3-chloropyrazin-2-yl)methyl) carbamoyl)bicyclo[3.2.1]octane-8-carboxylate (1 g, 2.96 mmol) in dry MeCN (10 mL) was added PCl$_5$ (1.85 g, 8.88 mmol). The reaction mixture was stirred at 85° C. for 1.5 hours. TLC (petroleum ether:EtOAc=1:1, R$_f$=0.62) showed the reaction was completed. Then the reaction mixture was poured into cold and saturated solution of NaHCO$_3$ (30 mL) and stirred for 5 minutes. The resulting mixture was extracted with EtOAc (30 mL×3), the combined organic layers were dried over Na$_2$SO$_4$, filtered and evaporated to dryness to afford the crude title product, which was used in the next step directly. $^1$H NMR (400 MHz, CDCl$_3$): δ 7.88 (d, J=4.7 Hz, 1H), 7.76 (s, 1H), 7.32 (d, J=5.1 Hz, 1H), 3.77 (s, 3H), 3.62-3.43 (m, 1H), 2.64 (d, J=9.4 Hz, 3H), 2.34 (t, J=12.9 Hz, 2H), 1.96-1.88 (m, 2H), 1.83-1.64 (m, 4H) ppm.

Step 9: methyl 3-(1-bromo-8-chloroimidazo[1,5-a] pyrazin-3-yl)bicyclo[3.2.1]octane-8-carboxylate To a solution of methyl 3-(8-chloroimidazo[1,5-a] pyrazin-3-yl)bicyclo[3.2.1]octane-8-carboxylate (935 mg, 2.92 mmol) in MeCN (15 mL) was added NBS (572 mg, 3.22 mmol). The reaction mixture was stirred at 15° C. for 1 hour. The reaction mixture was poured into saturated aqueous solution of NaHCO$_3$ and extracted with EtOAc, the organic layer was dried over Na$_2$SO$_4$, filtered and concentrated to dryness to afford the crude title product, which was used in the next step directly. $^1$H NMR (400 MHz, CDCl$_3$): δ 7.94 (d, J=5.1 Hz, 1H), 7.29 (d, J=5.1 Hz, 1H), 3.77 (s, 3H), 2.62 (d, J=11.0 Hz, 2H), 2.32 (t, J=12.9 Hz, 2H), 2.07-1.83 (m, 4H), 1.71 (d, J=8.2 Hz, 2H), 1.67-1.54 (m, 2H) ppm.

Step 10: methyl 3-(8-amino-1-bromoimidazo[1,5-a] pyrazin-3-yl)bicyclo[3.2.1] octane-8-carboxylate To a solution of methyl 3-(1-bromo-8-chloroimidazo[1, 5-a]pyrazin-3-yl)bicyclo[3.2.1] octane-8-carboxylate (500 mg, 1.254 mmol) in 2-propanol (8 mL) was added ammonium hydroxide (8 mL, 57.5 mmol). The reaction mixture was sealed and stirred at 110° C. (the oil bath temperature) for 16 hours The reaction mixture was concentrated under reduced pressure to afford the crude title product, which was used in the next step directly. $^1$H NMR (400 MHz, DMSO-d6): δ 7.63 (d, J=4.7 Hz, 1H), 6.95 (d, J=4.7 Hz, 1H), 6.60 (brs, 2H), 3.65 (s, 3H), 2.63 (brs, 1H), 2.57-2.50 (m, 2H), 2.46-2.44 (m, 1H), 1.98-1.86 (m, 2H), 1.80-1.71 (m, 4H), 1.57 (m, 2H) ppm.

Intermediate 18E1 & 18E2

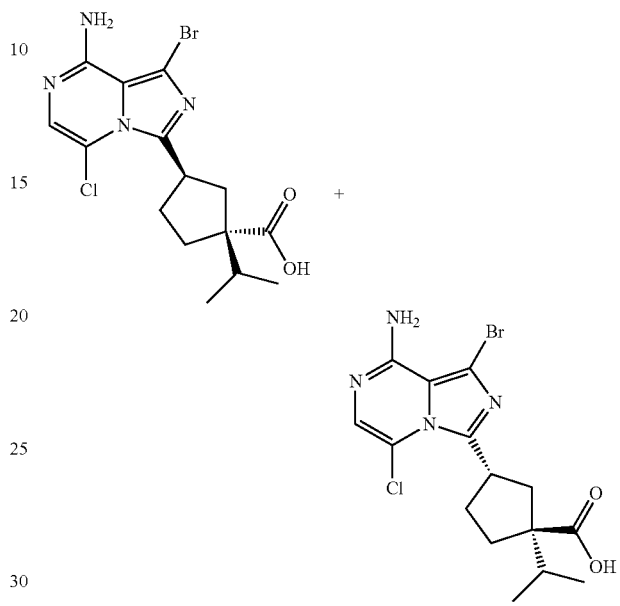

(1R,3R)-3-(8-amino-1-bromo-5-chloroimidazo[1,5-a]pyrazin-3-yl)-1-isopropylcyclopentanecarboxylic acid and (1S,3S)-3-(8-amino-1-bromo-5-chloroimidazo[1,5-a]pyrazin-3-yl)-1-isopropylcyclopentanecarboxylic acid

Step 1: (trans)-methyl 3-(8-amino-1-bromo-5-chloroimidazo[1,5-a]pyrazin-3-yl)-1-isopropylcyclopentanecarboxylate To a solution of trans-methyl 3-(8-amino-1-bromoimidazo[1,5-a]pyrazin-3-yl)-1-isopropylcyclopentanecarboxylate (1.20 g, 3.15 mmol) in AcOH (11 ml) was added NCS (462 mg, 3.46 mmol) in one portion. After the addition was completed, the mixture was stirred at 80° C. under the protection of N$_2$ for 3 h. The reaction was cooled to room temperature and concentrated in vacuum to remove the solvent. The mixture was extracted with ethyl acetate (15 mL×3). The combined organics was dried over anhydrous Na$_2$SO$_4$, filtered and concentrated in vacuum to remove the solvent. The residue was purified by column chromatography on gel silica (PE/THF=3:1) to afford trans-methyl 3-(8-amino-1-bromo-5-chloroimidazo[1,5-a]pyrazin-3-yl)-1-isopropylcyclopentanecarboxylate as solid. MS: 415.1 (M+1)

Step 2: (trans)-3-(8-amino-1-bromo-5-chloroimidazo[1,5-a]pyrazin-3-yl)-1-isopropylcyclo pentanecarboxylic acid To a solution of trans-3-(8-amino-1-bromo-5-chloroimidazo[1,5-a]pyrazin-3-yl)-1-isopropylcyclopentanecarboxylic acid (1.0 g, 2.41 mmol) in DCM (50 ml) was added tribromoborane (6.82 ml, 72.2 mmol) dropwise at −78° C.

The mixture was stirred at 15 degree for 40 hours. The mixture was quenched by the addition of water (20 mL) at −40° C. slowly. The resulting mixture was adjust PH=6 with Sat. NaHCO$_3$, the solid was collected via filtration and was dried to give trans-3-(8-amino-1-bromo-5-chloroimidazo[1,5-a]pyrazin-3-yl)-1-isopropylcyclopentanecarboxylic acid. $^1$H NMR (400 MHz, DMSO-d$_6$) δ=8.15 (br. s., 2H), 7.19 (s, 1H), 4.02 (dd, J=8.2, 16.4 Hz, 1H), 2.34 (d, J=6.7 Hz, 1H), 2.23 (d, J=12.1 Hz, 1H), 2.15-1.91 (m, 4H), 1.66-1.55 (m, 1H), 0.87 (dd, J=6.5, 15.1 Hz, 6H) ppm.

Step 3: (1R,3R)-3-(8-amino-1-bromo-5-chloroimidazo[1,5-a]pyrazin-3-yl)-1-isopropylcyclopentanecarboxylic acid and (1S,3S)-3-(8-amino-1-bromo-5-chloroimidazo[1,5-a]pyrazin-3-yl)-1-isopropylcyclopentanecarboxylic acid The trans-3-(8-amino-1-bromo-5-chloroimidazo[1,5-a]pyrazin-3-yl)-1-isopropylcyclopentane carboxylic acid was resolved by preparative SFC to give the (1R,3R)-3-(8-amino-1-bromo-5-chloroimidazo[1,5-a]pyrazin-3-yl)-1-isopropylcyclopentanecarboxylic acid and (1S,3S)-3-(8-amino-1-bromo-5-chloroimidazo[1,5-a]pyrazin-3-yl)-1-isopropylcyclopentanecarboxylic acid Intermediate 19_A

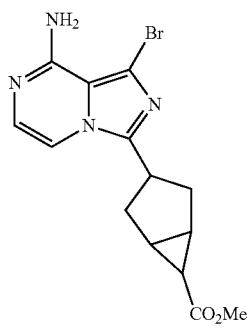

Isomer A

Ethyl 3-(8-amino-1-bromoimidazo[1,5-a]pyrazin-3-yl)bicyclo[3.1.0]hexane-6-carboxylate Step 1: cyclopent-3-en-1-ylmethanol To a suspension of LiAlH$_4$ (6.77 g, 178 mmol) in dry THF (100 mL), was added cyclopent-3-enecarboxylic acid (5.0 g, 44.6 mmol) dropwise at 0° C. After that, the temperature of the mixture was warmed to room temperature and stirred for 3 hours. A solution NaOH (10 mL) in 10 mL of H$_2$O was then added slowly and the mixture was stirred for 1 hour. After filtration, the filtrate was concentrated under vacuum to give cyclopent-3-en-1-ylmethanol which was used in next step without further purification. $^1$H NMR (400 MHz, DMSO-d$_6$) δ=5.64 (s, 2H), 4.54 (t, J=5.3 Hz, 1H), 3.26 (t, J=5.5 Hz, 2H), 2.38-2.27 (m, 3H), 2.09-1.98 (m, 2H) ppm.

Step 2: tert-butyl(cyclopent-3-en-1-yl)methoxy)dimethylsilane

To a mixture of cyclopent-3-en-1-ylmethanol (3.72 g, 37.9 mmol) and 1H-imidazole (5.68 g, 83 mmol) in DMF (100 mL) at 0° C. was added tert-butylchlorodimethylsilane (6.86 g, 45.5 mmol). The resulting mixture was stirred at room temperature for 18 h. The mixture was diluted with H$_2$O (200 mL), extracted with EtOAc (35 mL×2). The combined organic layers were dried over Na$_2$SO$_4$, concentrated and purified by combi flash (0-5% THF/Petroleum ether) to give tert-butyl(cyclopent-3-en-1-ylmethoxy)dimethylsilane. $^1$H NMR (400 MHz, CDCl$_3$) δ=5.60 (s, 2H), 3.44 (d, J=7.0 Hz, 2H), 2.56-2.28 (m, 3H), 2.10-1.92 (m, 2H), 0.85 (s, 9H), 0.00 (s, 6H) ppm.

Step 3: ethyl 3-(((tert-butyldimethylsilyl)oxy)methyl)bicyclo[3.1.0]hexane-6-carboxylate To the solution of tert-butyl(cyclopent-3-en-1-ylmethoxy)dimethylsilane (5.45 g, 25.7 mmol) and Rh$_2$(OAc)$_4$ (0.567 g, 1.283 mmol) at 35° C. was added ethyl 2-diazoacetate (7.32 g, 64.1 mmol) dropwise over 5 hours. The mixture was stirred at 35° C. for 18 h. The reaction solution was filtered and the filtrate was concentrated in vacuo. The resulting residue was purified with combi flash (0-5% THF/Petroleum ether) to give ethyl 3-(((tert-butyldimethylsilyl)oxy)methyl)bicyclo[3.1.0]hexane-6-carboxylate. $^1$H NMR (400 MHz, CDCl$_3$) δ=4.19-4.00 (m, 2H), 3.52-3.29 (m, 2H), 1.99 (d, J=7.8 Hz, 1H), 1.93-1.79 (m, 2H), 1.76-1.63 (m, 2H), 1.61-1.49 (m, 2H), 1.46-1.35 (m, 1H), 1.24 (td, J=7.1, 10.1 Hz, 3H), 0.93-0.82 (m, 9H), 0.06-0.06 (m, 6H) ppm.

Step 4: ethyl 3-(hydroxymethyl)bicyclo[3.1.0]hexane-6-carboxylate

To a solution of ethyl 3-(((tert-butyldimethylsilyl)oxy)methyl)bicyclo[3.1.0]hexane-6-carboxylate (4.67 g, 15.65 mmol) in THF (80 mL) was added TBAF (39.1 ml, 39.1 mmol, 1.0M in THF). The reaction was heated at 50° C. for 5 hours. The mixture was diluted with H$_2$O (200 mL), extracted with ethyl acetate (40 mL×3). The combined organic layers were dried over anhydrous sodium sulfate, filtered and concentrated under vacuum to give crude product which was purified by combi flash (0-20% THF/Petroleum ether) to give ethyl 3-(hydroxymethyl)bicyclo[3.1.0]hexane-6-carboxylate. $^1$H NMR (400 MHz, CDCl$_3$) δ=4.18-4.03 (m, 2H), 3.68-3.35 (m, 2H), 2.27-2.15 (m, 1H), 2.12-2.04 (m, 1H), 1.97 (dd, J=7.4, 12.5 Hz, 1H), 1.88 (br. s., 1H), 1.83-1.73 (m, 1H), 1.68 (d, J=5.1 Hz, 1H), 1.63-1.51 (m, 2H), 1.25 (td, J=7.2, 11.1 Hz, 3H) ppm.

Step 5: 6-(ethoxycarbonyl)bicyclo[3.1.0]hexane-3-carboxylic acid

RuCl$_3$ (0.109 g, 0.524 mmol) was added to a mixture of ethyl 3-(hydroxymethyl)bicyclo[3.1.0]hexane-6-carboxylate (1.93 g, 10.48 mmol) and NaIO$_4$ (8.96 g, 41.9 mmol) in H$_2$O (30 mL), MeCN (20 mL) and EtOAc (20 mL). The reaction mixture was stirred at 30° C. for about 16 hours. The reaction mixture was filtered, and the filtrate was concentrated in vacuo. The residue was purified by combi flash (0-100% THF/Petroleum ether) to give 6-(ethoxycarbonyl)bicyclo[3.1.0]hexane-3-carboxylic acid. $^1$H NMR (400 MHz, DMSO-d$_6$) δ=12.13 (br. s., 1H), 4.10-3.93 (m, 2H), 2.89 (m, 1H), 2.17-1.97 (m, 3H), 1.93-1.83 (m, 1H), 1.80-1.72 (m, 2H), 1.68-1.53 (m, 1H), 1.24-1.10 (m, 3H) ppm.

Step 6: ethyl 3-(((3-chloropyrazin-2-yl)methyl)carbamoyl)bicyclo[3.1.0]hexane-6-carboxylate To a solution of 6-(ethoxycarbonyl)bicyclo[3.1.0]hexane-3-carboxylic acid (2.09 g, 10.54 mmol) in CH$_2$Cl$_2$ (60 mL)

was added HATU (6.01 g, 15.82 mmol) under N₂. Then (3-chloropyrazin-2-yl)methanamine hydrochloride (2.278 g, 12.65 mmol) and Et₃N (2.94 mL, 21.09 mmol) was added. The resulting mixture was stirred at 30° C. for 18 hours. The mixture was diluted with H₂O (100 mL), extracted with CH₂Cl₂ (30 mL×3). The combined organic layers were dried over anhydrous sodium sulfate, filtered and concentrated under vacuum to give crude product, which was purified by combi flash (0-50% THF/Petroleum ether) to give ethyl 3-(((3-chloropyrazin-2-yl)methyl)carbamoyl)bicyclo[3.1.0] hexane-6-carboxylate. ¹H NMR (400 MHz, CDCl₃δ=8.45 (br. s., 1H), 8.32 (br. s., 1H), 6.95-6.65 (m, 1H), 4.67 (br. s., 2H), 4.20-4.02 (m, 2H), 3.01 (d, J=7.0 Hz, 1H), 2.41-2.30 (m, 1H), 2.29-2.22 (m, 1H), 2.21-2.13 (m, 2H), 1.96 (br. s., 1H), 1.90 (br. s., 1H), 1.60-1.43 (m, 1H), 1.33-1.19 (m, 3H) ppm.

Step 7: ethyl 3-(((3-chloropyrazin-2-yl)methyl)carbamoyl)bicyclo[3.1.0]hexane-6-carboxylate The product ethyl 3-(((3-chloropyrazin-2-yl)methyl)carbamoyl)bicyclo[3.1.0]hexane-6-carboxylate was resolved by SFC (The chiral HPLC condition was [Instrument: Thar 80; Column: Chiralpak AD-3 150×4.6 mm I.D; Mobile phase: methanol (0.05% DEA) in CO₂ from 5% to 40%, Flow rate: 2.5 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm]) to give ethyl 3-(((3-chloropyrazin-2-yl)methyl)carbamoyl)bicyclo[3.1.0]hexane-6-carboxylate (isomer 1)(Rt=3.83 min, 100% Area). ¹H NMR (400 MHz, CDCl₃) δ: 8.42 (d, J=2.0 Hz, 1H), 8.26 (s, 1H), 7.94 (br. s., 1H), 4.69 (d, J=5.1 Hz, 2H), 4.11 (q, J=7.3 Hz, 2H), 3.36 (quin, J=10.3 Hz, 1H), 2.39-2.26 (m, 2H), 2.21-2.11 (m, 2H), 2.07-1.98 (m, 2H), 1.84-1.73 (m, 1H), 1.25 (t, J=7.0 Hz, 3H) ppm.

Step 8: ethyl 3-(8-chloroimidazo[1,5-a]pyrazin-3-yl)bicyclo[3.1.0]hexane-6-carboxylate To a solution of ethyl 3-(((3-chloropyrazin-2-yl)methyl)carbamoyl)bicyclo[3.1.0]hexane-6-carboxylate (isomer 1) (0.18 g, 0.556 mmol) in MeCN (10 mL) was added PCl₅ (0.347 g, 1.668 mmol) at 0° C. The residue was stirred at 11° C. for 1 h. The reaction solution was poured into ice cooled sat. NaHCO₃ (aq.) (20 mL), diluted with H₂O (30 mL), extracted with EtOAc (15 mL×2). The combined organic layers were dried over anhydrous sodium sulfate, filtered and concentrated under vacuum to give crude product. The crude one was purified by combi flash (0-50% THF/Petroleum ether) to give (ethyl 3-(8-chloroimidazo[1,5-a]pyrazin-3-yl)bicyclo[3.1.0]hexane-6-carboxylate (isomer 1). ¹H NMR (400 MHz, CDCl₃) δ=7.85 (d, J=4.7 Hz, 1H), 7.79 (s, 1H), 7.29 (d, J=5.1 Hz, 1H), 4.18-3.99 (m, 3H), 2.62-2.51 (m, 2H), 2.48-2.36 (m, 2H), 2.11 (br. s., 2H), 1.90-1.81 (m, 1H), 1.28-1.20 (m, 3H) ppm.

Step 9: ethyl 3-(1-bromo-8-chloroimidazo[1,5-a]pyrazin-3-yl)bicyclo[3.1.0]hexane-6-carboxylate To a solution of ethyl 3-(8-chloroimidazo[1,5-a]pyrazin-3-yl)bicyclo[3.1.0]hexane-6-carboxylate (isomer 1) (70 mg, 0.229 mmol) in MeCN (6 mL) was added NBS (48.9 mg, 0.275 mmol). The residue was stirred at 15° C. for 1.5 h. The mixture was diluted with H₂O (50 mL), extracted with EtOAc (15 mL×2). The combined organic layers were dried over anhydrous sodium sulfate, filtered and concentrated under vacuum to give crude product ethyl 3-(1-bromo-8-chloroimidazo[1,5-a]pyrazin-3-yl)bicyclo[3.1.0]hexane-6-carboxylate (isomer 1), which was used in next step without further purification. MS 386.0 (M+1).

Step 10: ethyl 3-(8-amino-1-bromoimidazo[1,5-a]pyrazin-3-yl)bicyclo[3.1.0]hexane-6-carboxylate To a solution of ethyl 3-(1-bromo-8-chloroimidazo[1,5-a]pyrazin-3-yl)bicyclo[3.1.0]hexane-6-carboxylate (85 mg, 0.221 mmol) (isomer 1) in 2-propanol (4 mL) and ammoniumhydroxude (8 ml, 57.5 mmol) was sealed in a tube and stirred at 100° C. for 18 h. LCMS showed the starting material was consumed completely. The reaction solution was concentrated in vacuo to give the title compound, which was used in next step without further purification. MS: 367.0 (M+1).

Intermediate 19_B

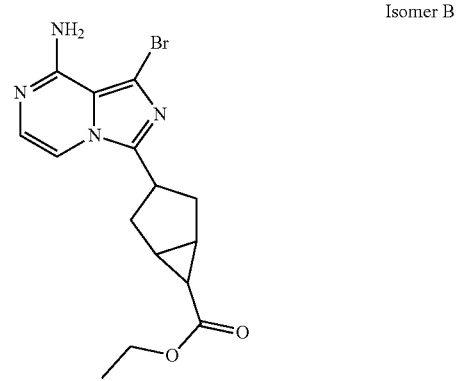 [SMILES: CCOC(=O)C1C2CC(c3nc(Br)c4c(N)nccn34)CC21]

Isomer B ethyl 3-(8-amino-1-bromoimidazo[1,5-a]pyrazin-3-yl)bicyclo[3.1.0]hexane-6-carboxylate The title compound was obtained in an analogues manner as described for intermediate 19_A from ethyl-3-(((3-chloropyrazin-2-yl)methyl)carbamoyl)bicyclo[3.1.0]hexane-6-carboxylate (isomer 2) (Rt=4.569 min, 93.79% Area) (obtained with chiral HPLC as the same condition at step 7 of intermediate 19_A). MS: 367.0 (M+1).

Intermediate 19_C

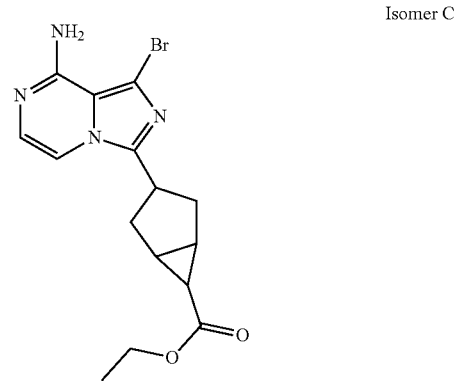 [SMILES: CCOC(=O)C1C2CC(c3nc(Br)c4c(N)nccn34)CC21]

Isomer C ethyl 3-(8-amino-1-bromoimidazo[1,5-a]pyrazin-3-yl)bicyclo[3.1.0]hexane-6-carboxylate The title compound was obtained in an analogues manner as described for intermediate 19_A from ethyl-3-(((3-chloropyrazin-2-yl)methyl)carbamoyl)bicyclo[3.1.0]hexane-6-carboxylate (isomer 3) (Rt=5.026 min, 93.79% Area) (obtained with chiral HPLC as the same condition at step 7 of intermediate 19_A). MS: 367.0 (M+1).

Intermediate 19_D

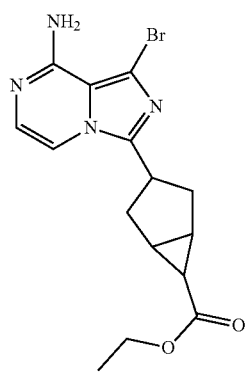

Isomer D ethyl 3-(8-amino-1-bromoimidazo[1,5-a]pyrazin-3-yl)bicyclo[3.1.0]hexane-6-carboxylate The title compound was obtained in an analogues manner as described for intermediate 19_A from ethyl-3-(((3-chloropyrazin-2-yl)methyl)carbamoyl)bicyclo[3.1.0]hexane-6-carboxylate (isomer 4) (Rt=5.334 min, 93.79% Area) (obtained with chiral HPLC as the same condition at step 7 of intermediate 19_A). MS: 367.0 (M+1).

Intermediate 20E1

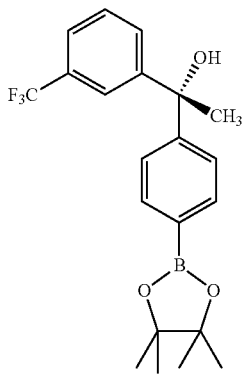 [SMILES: CC1(C)OB(c2ccc([C@@](C)(O)c3cccc(C(F)(F)F)c3)cc2)OC1(C)C]

(R)-1-(4-(4,4,5,5-tetramethyl-1,3,2-dioxaborolan-2-yl)phenyl)-1-(3-(trifluoromethyl)phenyl) ethanol Step 1: 1-(4-chlorophenyl)-1-(3-(trifluoromethyl)phenyl)ethanol To a solution of 1-(3-(trifluoromethyl)phenyl)ethanone (188 mg, 0.999 mmol) in Toluene (10 ml) was added (4-chlorophenyl)magnesium bromide (1.199 ml, 1.199 mmol) under $N_2$ protection and stirred for 10 minutes. The mixture was poured into water (5 mL) and filtered. The filtrate was extracted with EtOAc (10 mL). The organic layer was washed with brine, dried over $Na_2SO_4$ and concentrated in vacuo to give crude product, which was purified by chromatography over silica gel (4 g) (Per. Ether:THF=20:1) to give 1-(4-chlorophenyl)-1-(3-(trifluoromethyl)phenyl)ethanol. $^1$H NMR (400 MHz, CDCl$_3$) δ 7.74 (s, 1H), 7.52 (d, J=7.43 Hz, 2H), 7.39-7.46 (m, 1H), 7.27-7.37 (m, 4H), 2.30 (s, 1H), 1.95 (s, 3H) ppm.

Step 2: (R)-1-(4-chlorophenyl)-1-(3-(trifluoromethyl)phenyl)ethanol

The compound (R)-1-(4-chlorophenyl)-1-(3-(trifluoromethyl)phenyl)ethanol and (S)-1-(4-chlorophenyl)-1-(3-(trifluoromethyl)phenyl)ethanol was obtained after resolved by SFC. SFC method: AD (250×30, 10 mm). MeOH: $CO_2$=15:85, 0.1% NH3.

Step 3: (R)-1-(4-(4,455-tetramethyl-1,3,2-dioxaborolan-2-yl)phenyl)-1-(3-(trifluoromethyl)phenyl) ethanol A solution of (BPin)2 (209 mg, 0.823 mmol), (R)-1-(4-chlorophenyl)-1-(3-(trifluoromethyl)phenyl)ethanol (165 mg, 0.549 mmol), KOAc (162 mg, 1.646 mmol), X-Phos (26.2 mg, 0.055 mmol) and Pd2(dba)3 (25.1 mg, 0.027 mmol) in 1,4-Dioxane (5 ml) was stirred at 120° C. for 1 hour heated by microwave. The solution was concentrated in vacuo and purified by chromatography over silica gel (4 g) (THF: pet. Ether=10:90) to give (R)-1-(4-(4,4,5,5-tetramethyl-1,3,2-dioxaborolan-2-yl)phenyl)-1-(3-(trifluoromethyl)phenyl)ethanol. $^1$H NMR (400 MHz, CDCl$_3$) δ ppm 1.34 (s, 12H), 1.97 (s, 3H), 7.39-7.44 (m, 3H), 7.52 (d, J=7.78 Hz, 1H), 7.49 (d, J=7.53 Hz, 1H), 7.72-7.83 (m, 3H).

Intermediate 20 E2

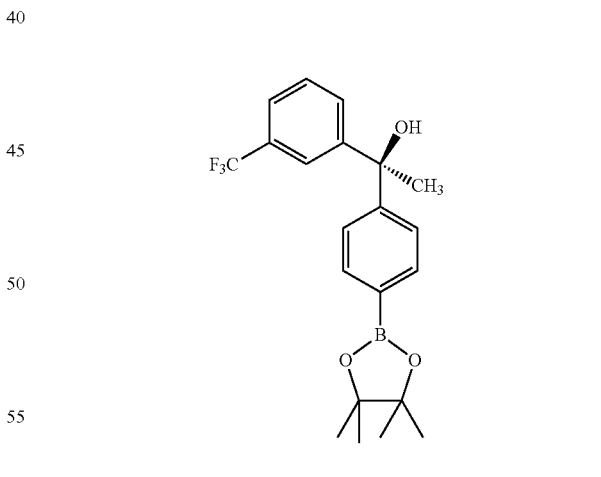

(S)-1-(4-(4,4,5,5-tetramethyl-1,3,2-dioxaborolan-2-yl)phenyl)-1-(3-(trifluoromethyl)phenyl) ethanol The title compound was obtained in the same procedure as the other enantiomer intermediate 20E1, using the second enantiomer in step 2 for boronic ester formation in step 3. $^1$H NMR (400 MHz, CDCl$_3$) δ ppm 1.34 (s, 12H), 1.97 (s, 3H), 7.39-7.44 (m, 3H), 7.52 (d, J=7.78 Hz, 1H), 7.49 (d, J=7.53 Hz, 1H), 7.72-7.83 (m, 3H).

Intermediate 21 E1 and 21 E2

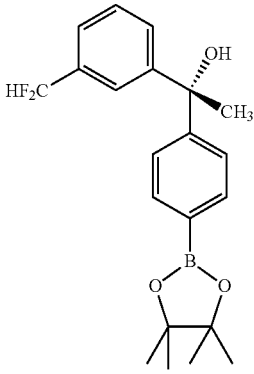

E1

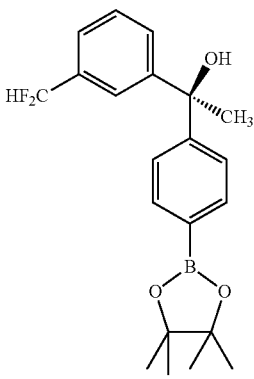

E2

(R)-1-(3-(difluoromethyl)phenyl)-1-(4-(4,4,5,5-tetramethyl-1,3,2-dioxaborolan-2-yl)phenyl)ethanol (S)-1-(3-(difluoromethyl)phenyl)-1-(4-(4,4,5,5-tetramethyl-1,3,2-dioxaborolan-2-yl)phenyl)ethanol In the same procedure as intermediate 20E1 and 20E2, starting from 1-(3 (difluoromethyl)phenyl) ethanone in step 1, the two title compounds (R)-1-(3-(difluoromethyl)phenyl)-1-(4-(4,4,5,5-tetramethyl-1,3,2-dioxaborolan-2-yl)phenyl)ethanol and (S)-1-(3-(difluoromethyl)phenyl)-1-(4-(4,4,5,5-tetramethyl-1,3,2-dioxaborolan-2-yl)phenyl)ethanol were prepared. LC-MS: (M+H)$^+$357.2, retention time=1.24 min (D).

Intermediate 22

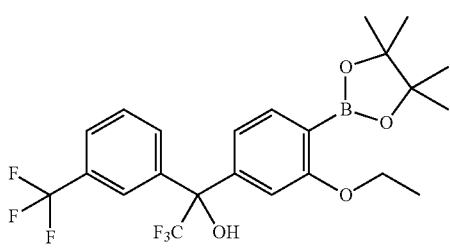 [SMILES: CCOc1cc(C(O)(c2cccc(C(F)(F)F)c2)C(F)(F)F)ccc1B1OC(C)(C)C(C)(C)O1]

1-(3-ethoxy-4-(4,4,5,5-tetramethyl-1,32-dioxaborolan-2-yl)phenyl)-2,2,2-trifluoro-1-(3-(trifluoromethyl)phenyl)ethanol Step 1: methyl 4-bromo-3-ethoxybenzoate To a mixture of methyl 4-bromo-3-hydroxybenzoate (4 g, 17.31 mmol) and K$_2$CO$_3$ (5.98 g, 43.3 mmol) in DMF (30 mL) was added iodoethane (6.75 g, 43.3 mmol) dropwise. The reaction mixture was stirred at 10° C. for 8 h. The reaction was quenched with 1N HCl (100 mL), and extracted with ethyl acetate (100 mL×2). The organic layers were washed with brine, dried over anhydrous sodium sulfate, concentrated to afford methyl 4-bromo-3-ethoxybenzoate.

Step 2: 4-bromo-3-ethoxybenzoic acid

To a solution of methyl 4-bromo-3-ethoxybenzoate (4.1 g, 15.82 mmol) in THF (20 mL) and MeOH (20.00 mL) was added LiOH (1.137 g, 47.5 mmol) and water (20 mL). The mixture was stirred at 12° C. for 3 h. The reaction was quenched with 1N HCl to pH=2 and extracted with EtOAc (100 mL×2). The combined organic layers were dried over anhydrous sodium sulfate, concentrated in vacuum to give 4-bromo-3-ethoxybenzoic acid.

Step 3: 4-bromo-3-ethoxy-N-methoxy-N-methylbenzamide

A mixture of 4-bromo-3-ethoxybenzoic acid (3.9 g, 15.91 mmol), N,O-dimethylhydroxylamine-HCl (1.863 g, 19.10 mmol), HATU (6.05 g, 15.91 mmol) and DIEA (8.34 mL, 47.7 mmol) in THF (30 mL) was stirred at 10° C. for 2 h. TLC detected the reaction was complete. The reaction mixture was quenched with sat. NH$_4$Cl aqueous (100 mL), extracted with EtOAc (80 mL×2). The organic layer was dried over sodium sulfate, concentrated to give the crude product, which was purified by column chromatography on silica gel (Pet. ether/EtOAc=3:1) to give 4-bromo-3-ethoxy-N-methoxy-N-methylbenzamide. $^1$H NMR (400 MHz, CDCl$_3$) δ: 7.55 (d, J=8.2 Hz, 1H), 7.22 (s, 1H), 7.18-7.13 (m, 1H), 4.13 (q, J=6.9 Hz, 2H), 3.54 (s, 3H), 3.35 (s, 3H), 1.47 (t, J=7.0 Hz, 3H) ppm.

Step 4: (4-bromo-3-ethoxyphenyl)(3-(trifluoromethyl)phenyl)methanone

To a mixture of magnesium (0.127 g, 5.21 mmol) and isopropylmagnesium chloride (0.347 mL, 0.694 mmol) in THF (2 mL) was added a solution of 1-bromo-3-(trifluoromethyl)benzene (0.937 g, 4.16 mmol) in THF (5 mL) dropwise at 80° C. under N$_2$. The solution was added to a solution of 4-bromo-3-ethoxy-N-methoxy-N-methylbenzamide (1 g, 3.47 mmol) in THF (10 mL) and the reaction was stirred at 15° C. for 2 h. The reaction mixture was quenched with sat. NH$_4$Cl aqueous (50 mL), extracted with EtOAc (50 mL×2). The combined organic phases were dried over Na$_2$SO$_4$, and concentrated to give (4-bromo-3-ethoxyphenyl)(3-(trifluoromethyl)phenyl)methanone.

Step 5: 1-(4-bromo-3-ethoxyphenyl)-2,2,2-trifluoro-1-(3-(trifluoromethyl)phenyl)ethanol To a solution of (4-bromo-3-ethoxyphenyl)(3-(trifluoromethyl)phenyl)methanone (1.3 g, 3.48 mmol) in THF (25 mL) were added trimethyl(trifluoromethyl)silane (0.743 g, 5.23 mmol) and tetrabutylammonium difluorotriphenylsilicate (0.940 g, 1.742 mmol) at 0° C. The reaction was stirred for 12 h at 14° C. under N₂. The reaction was quenched with 1M HCl (20 mL). 30 min later, the mixture was basified with aq. NaHCO₃ (30 mL), extracted with EtOAc (20 mL×3). The organic layer was washed with brine (30 mL), dried over Na₂SO₄, evaporated to give the crude product, which was purified by flash chromatography (Pet. ether/EtOAc=10:1) to give 1-(4-bromo-3-ethoxyphenyl)-2,2,2-trifluoro-1-(3-(trifluoromethyl)phenyl)ethanol. ¹H NMR (400 MHz, CDCl₃) δ: 7.82 (br. s., 1H), 7.62 (t, J=7.2 Hz, 2H), 7.57-7.46 (m, 2H), 7.03 (s, 1H), 6.89 (d, J=8.2 Hz, 1H), 4.09-3.99 (m, 2H), 3.08 (s, 1H), 1.44 (t, J=7.0 Hz, 3H) ppm.

Step 6: 1-(3-ethoxy-4-(4,4,5,5-tetramethyl-1,3,2-dioxaborolan-2-yl)phenyl)-2,2,2-trifluoro-1-(3-(trifluoromethyl)phenyl)ethanol The solution of 1-(4-bromo-3-ethoxyphenyl)-2,2,2-trifluoro-1-(3-(trifluoromethyl)phenyl)ethanol (800 mg, 1.805 mmol), 4,4,4',4',5,5,5',5'-octamethyl-2,2'-bi(1,3,2-dioxaborolane) (550 mg, 2.166 mmol), potassium acetate (531 mg, 5.42 mmol) and PdCl₂(dppf) (66.0 mg, 0.090 mmol) in 1,4-dioxane (15 mL) was stirred at 110° C. for 4 h under N₂. Then it was cooled and concentrated in vacuo. The residue was purified by chromatography on silica gel (Pet.ether: EtOAc=10:1) to give 1-(3-ethoxy-4-(4,4,5,5-tetramethyl-1,3,2-dioxaborolan-2-yl)phenyl)-2,2,2-trifluoro-1-(3-(trifluoromethyl)phenyl)ethanol. ¹H NMR (400 MHz, CDCl₃) δ: 7.80 (s, 1H), 7.61-7.55 (m, 2H), 7.46-7.40 (m, 2H), 7.03 (d, J=7.8 Hz, 1H), 6.94 (s, 1H), 3.96 (td, J=6.6, 12.7 Hz, 2H), 3.02 (s, 1H), 1.40-1.33 (m, 15H) ppm.

Intermediate 22

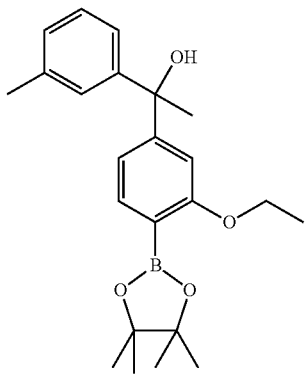 [SMILES: CCOc1cc(C(C)(O)c2cccc(C)c2)ccc1B1OC(C)(C)C(C)(C)O1]

1-(3-ethoxy-4-(4,4,5,5-tetramethyl-1,3,2-dioxaborolan-2-yl)phenyl)-1-(m-tolyl)ethanol The intermediate 22 was prepared in the same procedure as intermediate 21, using 1-bromo-3-methylbenzene as the starting material in step 4 to provide the title compound 1-(3-ethoxy-4-(4,4,5,5-tetramethyl-1,3,2-dioxaborolan-2-yl)phenyl)-1-(m-tolyl)ethanol. LC-MS: (M+H)⁺ 365.1.

Example 1

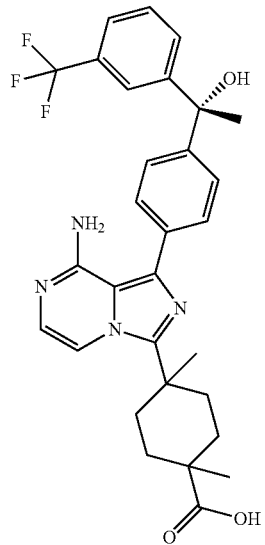 [SMILES: CC1(C(=O)O)CCC(C)(c2nc(-c3ccc([C@@](C)(O)c4cccc(C(F)(F)F)c4)cc3)c3c(N)nccn23)CC1]

(R)-4-(8-amino-1-(4-(1-hydroxy-1-(3-(trifluoromethyl)phenyl)ethyl)phenyl)imidazo[1,5-a]pyrazin-3-yl)-1,4-dimethylcyclohexanecarboxylic acid Step 1: 4-(8-amino-1-bromoimidazo[1,5-a]pyrazin-3-yl)-1-methylcyclohexanecarboxylic acid A solution of LiOH (201 mg, 8.37 mmol) and methyl 4-(8-amino-1-bromoimidazo[1,5-a]pyrazin-3-yl)-1-methylcyclohexanecarboxylate (615 mg, 1.675 mmol) in Water (15 ml) and MeOH (15 ml) was stirred at 60° C. for 8 hours. The solution was concentrated in vacuo and added 1N HCl to pH=2. The mixture was extracted with DCM/i-PrOH=3:1 (10 times). The combined organic was dried over Na₂SO₄ and concentrated in vacuo to give the compound 4-(8-amino-1-bromoimidazo[1,5-a]pyrazin-3-yl)-1-methylcyclohexanecarboxylic acid. LC-MS: (M+H)⁺ 367.1. Retention time=0.42 min (Method D).

Step 2: (R)-4-(8-amino-1-(4-(1-hydroxy-1-(3-(trifluoromethyl)phenyl)ethyl)phenyl) imidazo[1,5a]pyrazin-3-yl)-1,4-dimethylcyclohexanecarboxylic acid A solution of 4-(8-amino-1-bromoimidazo[1,5-a]pyrazin-3-yl)-1,4-dimethylcyclohexanecarboxylic acid (50 mg, 0.136 mmol), (R)-1-(4-(4,4,5,5-tetramethyl-1,3,2-dioxaborolan-2-yl)phenyl)-1-(3-(trifluoromethyl)phenyl)ethanol (50 mg, 0.127 mmol), K₂CO₃ (56.5 mg, 0.408 mmol) and PdCl2(dppf) (19.92 mg, 0.027 mmol) in 1,4-Dioxane (20 ml) and Water (5 ml) was stirred at 75° C. for 2 hours under N₂ protection. The mixture was concentrated in vacuo and added TFA to pH=3. The mixture was dissolved in MeCN, added 2 ml TMT and filtrated. The filtrate was purified by Pre-HPLC to give the compound (R)-4-(8-amino-1-(4-(1-hydroxy-1-(3-(trifluoromethyl)phenyl)ethyl)phenyl)imidazo[1,5-a]pyrazin-3-yl)-1,4-dimethylcyclohexanecarboxylic acid. LC-MS: (M+H)+553.2. ¹HNMR (CD₃OD, 400 MHz): d=7.93 (1H, d, J=5.6 Hz), 7.85 (1H, s), 7.74 (1H, d, J=6.8 Hz), 7.50 (4H, m), 6.91 (1H, d, J=5.2 Hz), 2.55 (2H, d, J=14.0 Hz), 2.09 (2H, d, J=14.0 Hz), 2.01 (3H, s), 1.68 (2H, t, J=12.8 Hz), 1.40 (3H, s), 1.37 (2H, d, J=15.6 Hz), 1.08 (3H, s) ppm.

The following Examples in Table 1 were prepared in the similar way as Example 1 following the hydrolysis of the ester and Suzuki coupling.

TABLE 1

| Example Number | Structure | IUPAC Name | Exact Mass [M + H]+ | Retention time (min, method) |
|---|---|---|---|---|
| 2 | 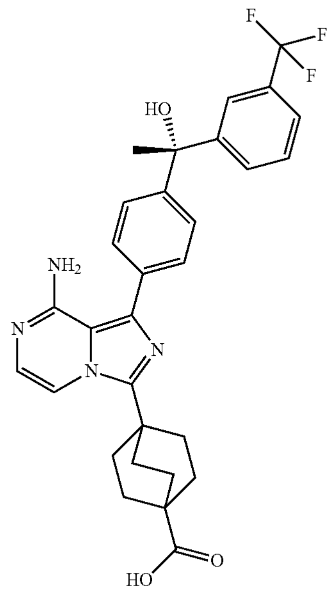 [SMILES: C[C@](O)(c1ccc(-c2nc(C34CCC(C(=O)O)(CC3)CC4)n3ccnc(N)c23)cc1)c1cccc(C(F)(F)F)c1] | 4-[8-amino-1-(4-{(1S)-1-hydroxy-1-[3-(trifluoromethyl)phenyl]ethyl}phenyl)imidazo[1,5-a]pyrazin-3-yl]bicyclo[2.2.2]octane-1-carboxylic acid | Calc'd 551.2, found 551.1 | 2.311 (C) |
| 3 | 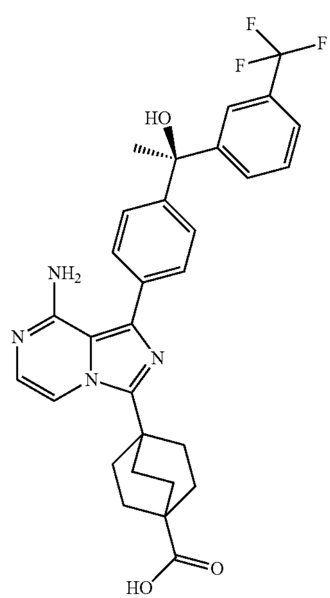 [SMILES: C[C@@](O)(c1ccc(-c2nc(C34CCC(C(=O)O)(CC3)CC4)n3ccnc(N)c23)cc1)c1cccc(C(F)(F)F)c1] | 4-[8-amino-1-(4-{(1R)-1-hydroxy-1-[3-(trifluoromethyl)phenyl]ethyl}phenyl)imidazo[1,5-a]pyrazin-3-yl]bicyclo[2.2.2]octane-1-carboxylic acid | Calc'd 551.2, found 551.1 | 2.317(C) |

TABLE 1-continued

| Example Number | Structure | IUPAC Name | Exact Mass [M + H]+ | Retention time (min, method) |
|---|---|---|---|---|
| 4 | 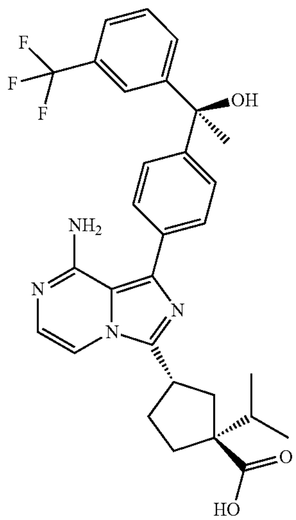 [SMILES: CC(C)[C@]1(C(=O)O)CC[C@H](c2nc(-c3ccc([C@](C)(O)c4cccc(C(F)(F)F)c4)cc3)c3c(N)nccn23)C1] | (1S,3S)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclopentane-carboxylic acid | Calc'd 553.2, found 553.2 | 2.639(C) |
| 5 | 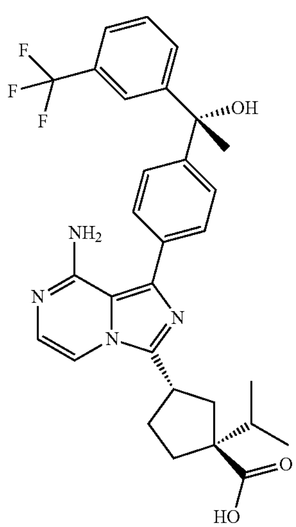 [SMILES: CC(C)[C@]1(C(=O)O)CC[C@H](c2nc(-c3ccc([C@@](C)(O)c4cccc(C(F)(F)F)c4)cc3)c3c(N)nccn23)C1] | (1S,3S)-3-[8-amino-1-(4-{(1R)-1-hydroxy-1-[3-(trifluoromethyl)phenyl]ethyl}phenyl)imidazo[1,5-a]pyrazin-3-yl]-1-(1-methylethyl)cyclopentane-carboxylic acid | Calc'd 553.2, found 553.2 | 2.637(C) |

TABLE 1-continued

| Example Number | Structure | IUPAC Name | Exact Mass [M + H]+ | Retention time (min, method) |
|---|---|---|---|---|
| 6 | 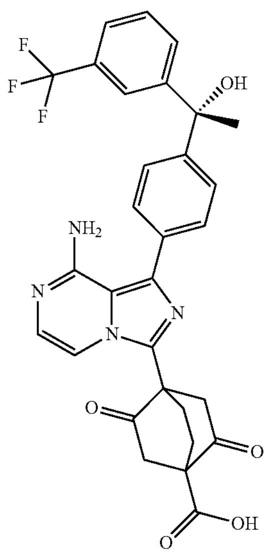 [SMILES: C[C@@](O)(c1ccc(-c2nc(C34CCC(C(=O)O)(CC3=O)C(=O)C4)n3ccnc(N)c23)cc1)c1cccc(C(F)(F)F)c1] | 4-[8-amino-1-(4-{(1R)-1-hydroxy-1-[3-(trifluoromethyl)phenyl]ethyl}phenyl)imidazo[1,5-a]pyrazin-3-yl]-2,5-dioxobicyclo[2.2.2]octane-1-carboxylic acid | Calc'd 579.2, found 579.2 | 2.489(C) |
| 7 | 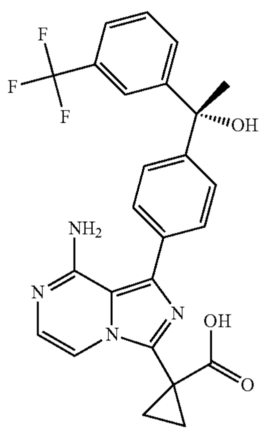 [SMILES: C[C@@](O)(c1ccc(-c2nc(C3(C(=O)O)CC3)n3ccnc(N)c23)cc1)c1cccc(C(F)(F)F)c1] | 1-[8-amino-1-(4-{(1R)-1-hydroxy-1-[3-(trifluoromethyl)phenyl]ethyl}phenyl)imidazo[1,5-a]pyrazin-3-yl]cyclopropanecarboxylic acid | Calc'd 483.2, found 483.1 | 2.430(C) |
| 8 | 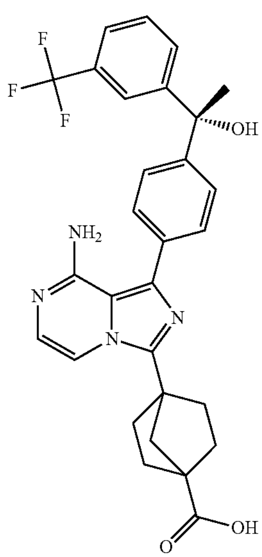 [SMILES: C[C@@](O)(c1ccc(-c2nc(C34CCC(C(=O)O)(CC3)C4)n3ccnc(N)c23)cc1)c1cccc(C(F)(F)F)c1] | 4-[8-amino-1-(4-{(1R)-1-hydroxy-1-[3-(trifluoromethyl)phenyl]ethyl}phenyl)imidazo[1,5-a]pyrazin-3-yl]bicyclo[2.2.1]heptane-1-carboxylic acid | Calc'd 537.2, found 537.2 | 2.193(C) |

TABLE 1-continued

| Example Number | Structure | IUPAC Name | Exact Mass [M + H]+ | Retention time (min, method) |
|---|---|---|---|---|
| 9 | 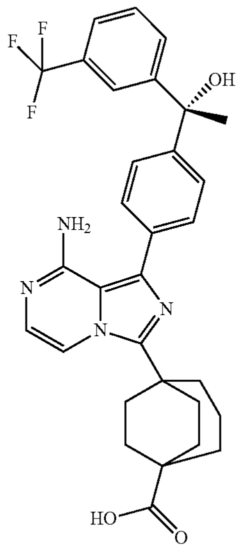 [SMILES: C[C@@](O)(c1ccc(-c2nc(C34CCCC(C(=O)O)(CC3)CC4)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]bicyclo[3.2.2]nonane-1-carboxylic acid | Calc'd 565.2, found 565.2 | 2.433(C) |
| 10 | 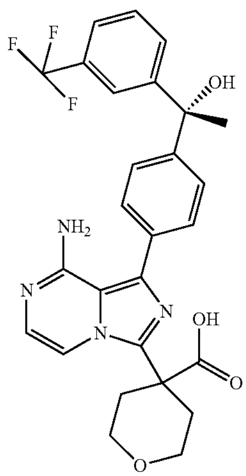 [SMILES: C[C@@](O)(c1ccc(-c2nc(C3(C(=O)O)CCOCC3)n3ccnc(N)c23)cc1)c1cccc(C(F)(F)F)c1] | 4-[8-amino-1-(4-{(1R)-1-hydroxy-1-[3-(trifluoromethyl)phenyl]ethyl}phenyl)imidazo[1,5-a]pyrazin-3-yl]tetrahydro-2H-pyran-4-carboxylic acid | Calc'd 527.2, found 527.1 | 2.499(C) |
| 11 | 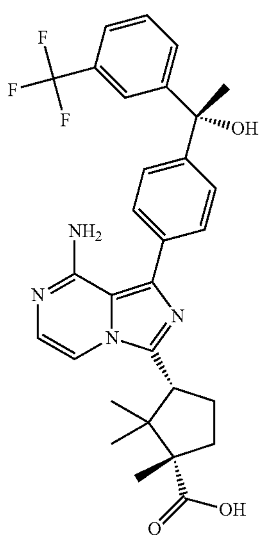 [SMILES: CC1(C)[C@H](c2nc(-c3ccc([C@@](C)(O)c4cccc(C(F)(F)F)c4)cc3)c3c(N)nccn23)CC[C@]1(C)C(=O)O] | (1S,3R)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentane-carboxylic acid | Calc'd 553.2, found 553.2 | 1.930(C) |

TABLE 1-continued

| Example Number | Structure | IUPAC Name | Exact Mass [M + H]+ | Retention time (min, method) |
|---|---|---|---|---|
| 12 | 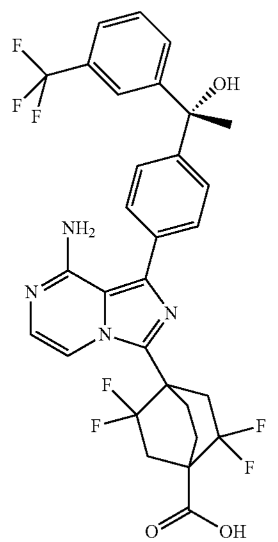 [SMILES: C[C@@](O)(c1ccc(-c2nc(C34CCC(C(=O)O)(CC3(F)F)C(F)(F)C4)n3ccnc(N)c23)cc1)c1cccc(C(F)(F)F)c1] | 4-[8-amino-1-(4-{(1R)-1-hydroxy-1-[3-(trifluoromethyl)phenyl]ethyl}phenyl)imidazo[1,5-a]pyrazin-3-yl]-2,2,5,5-tetrafluorobicyclo[2.2.2]octane-1-carboxylic acid | Calc'd 623.2, found 623.1 | 2.386(C) |
| 13 | 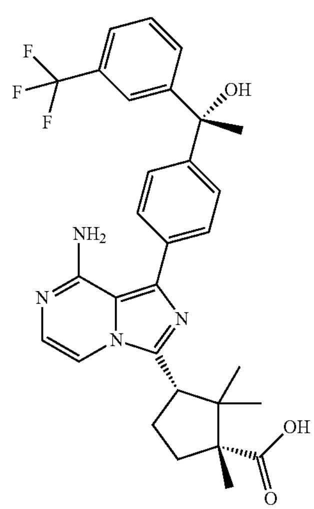 [SMILES: CC1(C)[C@@H](c2nc(-c3ccc([C@@](C)(O)c4cccc(C(F)(F)F)c4)cc3)c3c(N)nccn23)CC[C@@]1(C)C(=O)O] | (1R,3S)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentane-carboxylic acid | Calc'd 553.2, found 553.2 | 2.263(C) |

TABLE 1-continued

| Example Number | Structure | IUPAC Name | Exact Mass [M + H]+ | Retention time (min, method) |
|---|---|---|---|---|
| 14 | 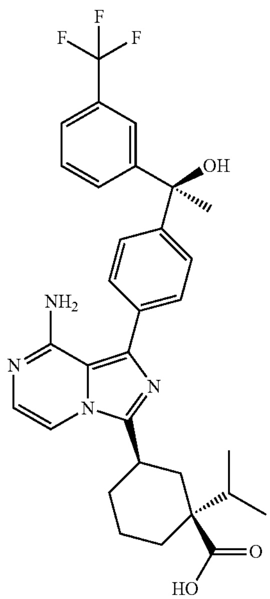 [SMILES: CC(C)[C@]1(C(=O)O)CCC[C@@H](c2nc(-c3ccc([C@](C)(O)c4cccc(C(F)(F)F)c4)cc3)c3c(N)nccn23)C1] | (1S,3R)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexane-carboxylic acid | Calc'd 567.3, found 567.2 | 1.956(C) |
| 15 | 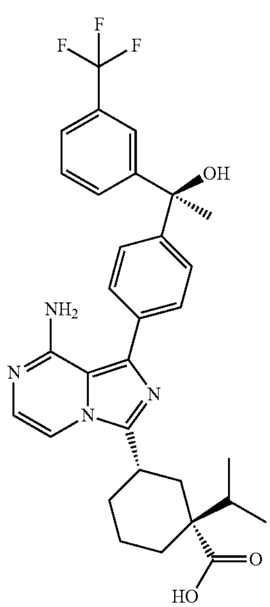 [SMILES: CC(C)[C@@]1(C(=O)O)CCC[C@H](c2nc(-c3ccc([C@](C)(O)c4cccc(C(F)(F)F)c4)cc3)c3c(N)nccn23)C1] | (1R,3S)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexane-carboxylic acid | Calc'd 567.3, found 567.2 | 2.017(C) |

TABLE 1-continued

| Example Number | Structure | IUPAC Name | Exact Mass [M + H]+ | Retention time (min, method) |
|---|---|---|---|---|
| 16 | 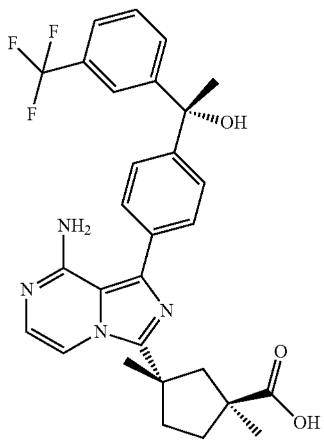 [SMILES: C[C@]1(C(=O)O)CC[C@](C)(c2nc(-c3ccc([C@@](C)(O)c4cccc(C(F)(F)F)c4)cc3)c3c(N)nccn23)C1] | (1S,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentane-carboxylic acid | Calc'd 539.2, found 539.1 | 2.356(C) |
| 17 | 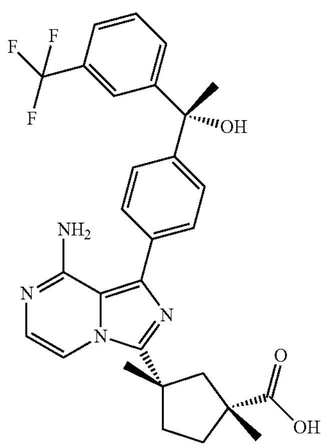 [SMILES: C[C@@]1(C(=O)O)CC[C@](C)(c2nc(-c3ccc([C@@](C)(O)c4cccc(C(F)(F)F)c4)cc3)c3c(N)nccn23)C1] | (1R,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentane-carboxylic acid | Calc'd 539.2, found 539.2 | 2.426(C) |
| 18 | 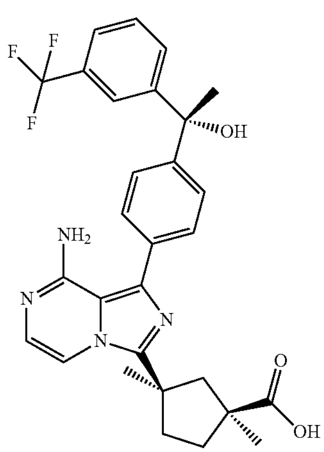 [SMILES: C[C@]1(C(=O)O)CC[C@@](C)(c2nc(-c3ccc([C@@](C)(O)c4cccc(C(F)(F)F)c4)cc3)c3c(N)nccn23)C1] | (1S,3R)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentane-carboxylic acid | Calc'd 539.2, found 539.1 | 2.428(C) |

TABLE 1-continued

| Example Number | Structure | IUPAC Name | Exact Mass [M + H]+ | Retention time (min, method) |
|---|---|---|---|---|
| 19 | 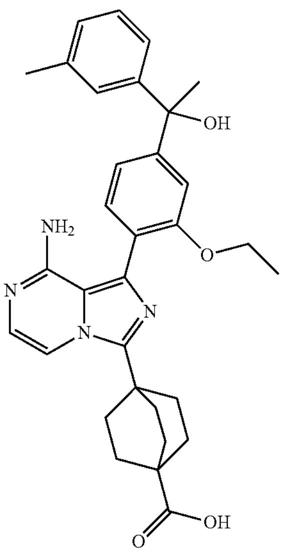 [SMILES: CCOc1cc(C(C)(O)c2cccc(C)c2)ccc1-c1nc(C23CCC(C(=O)O)(CC2)CC3)n2ccnc(N)c12] | 4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid | Calc'd 541.3, found 541.2 | 2.629(C) |
| 20 | 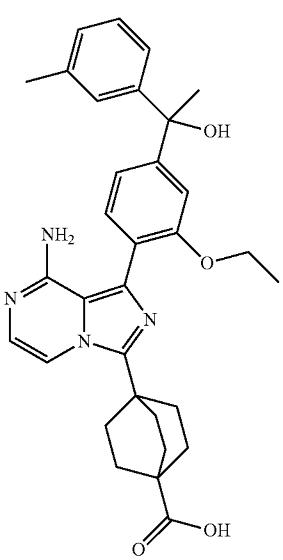 [SMILES: CCOc1cc(C(C)(O)c2cccc(C)c2)ccc1-c1nc(C23CCC(C(=O)O)(CC2)CC3)n2ccnc(N)c12] | 4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid | Calc'd 541.3, found 541.2 | 2.632(C) |

TABLE 1-continued

| Example Number | Structure | IUPAC Name | Exact Mass [M + H]+ | Retention time (min, method) |
|---|---|---|---|---|
| 21 | 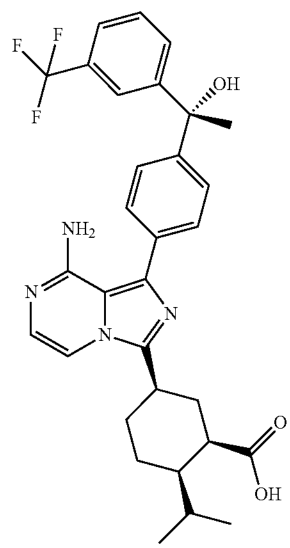 [SMILES: CC(C)[C@H]1CC[C@@H](c2nc(-c3ccc([C@@](C)(O)c4cccc(C(F)(F)F)c4)cc3)c3c(N)nccn23)C[C@H]1C(=O)O] | (1R,2R,5R)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexanecarboxylic acid | Calc'd 567.3, found 567.2 | 2.006(C) |
| 22 | 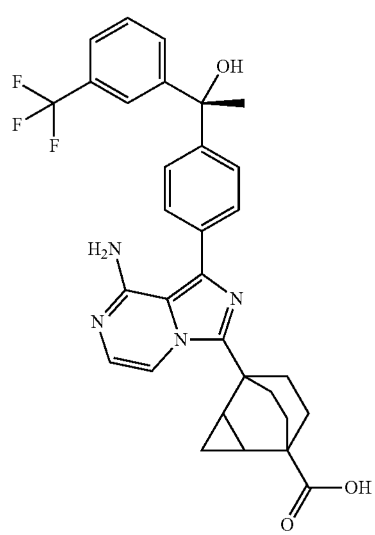 [SMILES: C[C@@](O)(c1ccc(-c2nc(C34CCC(C(=O)O)(CC3)C3CC34)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]tricyclo[3.2.2.0~2,4~]nonane-1-carboxylic acid | Calc'd 563.2, found 563.2 | 2.241(C) |

TABLE 1-continued

| Example Number | Structure | IUPAC Name | Exact Mass [M + H]+ | Retention time (min, method) |
|---|---|---|---|---|
| 23 | 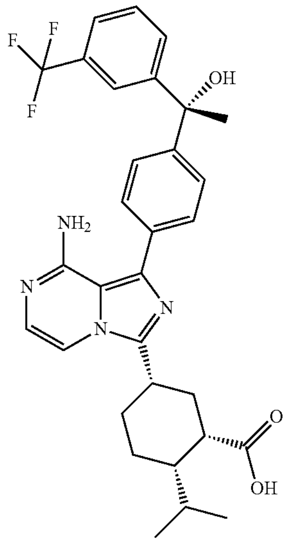 [SMILES: CC(C)[C@@H]1CC[C@H](c2nc(-c3ccc([C@@](C)(O)c4cccc(C(F)(F)F)c4)cc3)c3c(N)nccn23)C[C@@H]1C(=O)O] | (1S,2S,5S)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexane-carboxylic acid | Calc'd 567.3, found 567.2 | 2.163(C) |
| 24 | 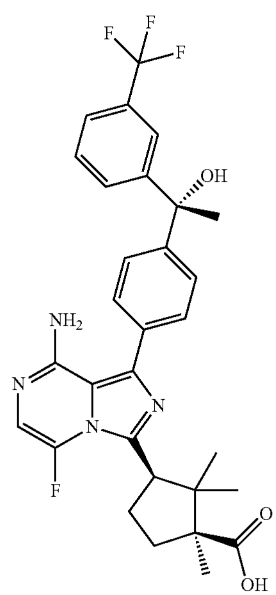 [SMILES: CC1(C)[C@H](c2nc(-c3ccc([C@@](C)(O)c4cccc(C(F)(F)F)c4)cc3)c3c(N)ncc(F)n23)CC[C@]1(C)C(=O)O] | (1S,3R)-3-[8-amino-5-fluoro-1-(4-{(1R)-1-hydroxy-1-[3-(trifluoromethyl)phenyl]ethyl}phenyl)imidazo[1,5-a]pyrazin-3-yl]-1,2,2-trimethylcyclopentane-carboxylic acid | Calc'd 571.2, found 571.1 | 1.957(C) |

TABLE 1-continued

| Example Number | Structure | IUPAC Name | Exact Mass [M + H]+ | Retention time (min, method) |
|---|---|---|---|---|
| 25 | 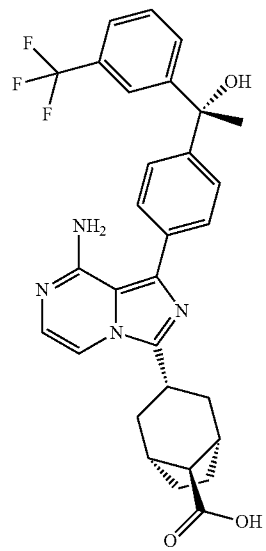 [SMILES: C[C@@](O)(c1ccc(-c2nc([C@H]3C[C@H]4CC[C@@H](C3)[C@H]4C(=O)O)n3ccnc(N)c23)cc1)c1cccc(C(F)(F)F)c1] | (3-endo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid | Calc'd 551.2, found 551.2 | 2.240(C) |
| 26 | 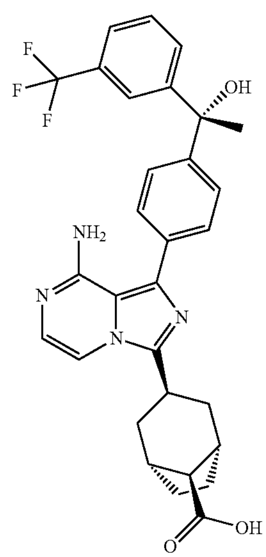 [SMILES: C[C@@](O)(c1ccc(-c2nc([C@@H]3C[C@H]4CC[C@@H](C3)[C@H]4C(=O)O)n3ccnc(N)c23)cc1)c1cccc(C(F)(F)F)c1] | (3-exo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid | Calc'd 551.2, found 551.2 | 1.969(C) |

TABLE 1-continued

| Example Number | Structure | IUPAC Name | Exact Mass [M + H]+ | Retention time (min, method) |
|---|---|---|---|---|
| 27 | 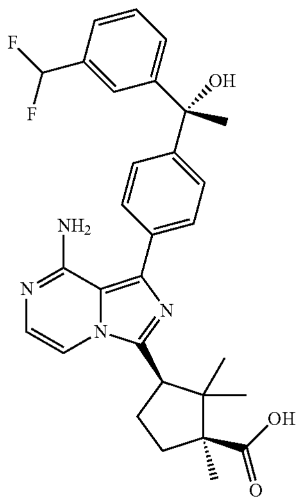 [SMILES: CC1(C)[C@H](c2nc(-c3ccc([C@@](C)(O)c4cccc(C(F)F)c4)cc3)c3c(N)nccn23)CC[C@]1(C)C(=O)O] | (1S,3R)-3-[8-amino-1-(4-{(1R)-1-[3-(difluoromethyl)phenyl]-1-hydroxyethyl}phenyl)imidazo[1,5-a]pyrazin-3-yl]-1,2,2-trimethylcyclopentanecarboxylic acid | Calc'd 535.3, found 535.2 | 2.162(C) |
| 28 | 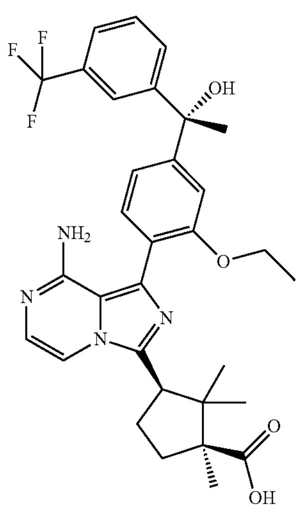 [SMILES: CCOc1cc([C@@](C)(O)c2cccc(C(F)(F)F)c2)ccc1-c1nc([C@@H]2CC[C@](C)(C(=O)O)C2(C)C)n2ccnc(N)c12] | (1S,3R)-3-[8-amino-1-(2-ethoxy-4-{(1S)-1-hydroxy-1-[3-(trifluoromethyl)phenyl]ethyl}phenyl)imidazo[1,5-a]pyrazin-3-yl]-1,2,2-trimethylcyclopentanecarboxylic acid | Calc'd 597.3, found 597.2 | 1.916(C) |

TABLE 1-continued

| Example Number | Structure | IUPAC Name | Exact Mass [M + H]+ | Retention time (min, method) |
|---|---|---|---|---|
| 29 | 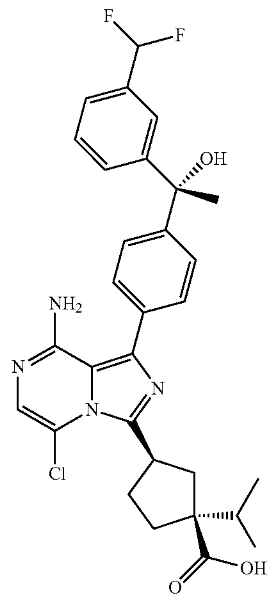 [SMILES: CC(C)[C@]1(C(=O)O)CC[C@@H](c2nc(-c3ccc([C@@](C)(O)c4cccc(C(F)F)c4)cc3)c3c(N)ncc(Cl)n23)C1] | (1S,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentane-carboxylic acid | Calc'd 569.2, found 569.2 | 2.438(C) |
| 30 | 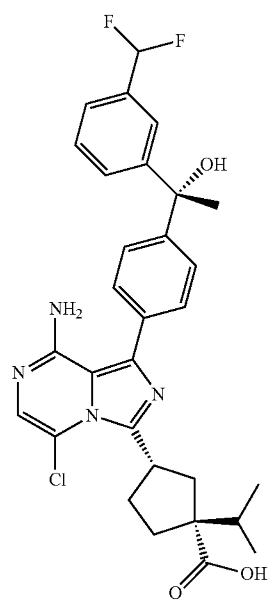 [SMILES: CC(C)[C@@]1(C(=O)O)CC[C@H](c2nc(-c3ccc([C@@](C)(O)c4cccc(C(F)F)c4)cc3)c3c(N)ncc(Cl)n23)C1] | (1R,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentane-carboxylic acid | Calc'd 569.2, found 569.2 | 2.433(C) |

TABLE 1-continued

| Example Number | Structure | IUPAC Name | Exact Mass [M + H]+ | Retention time (min, method) |
|---|---|---|---|---|
| 31 | 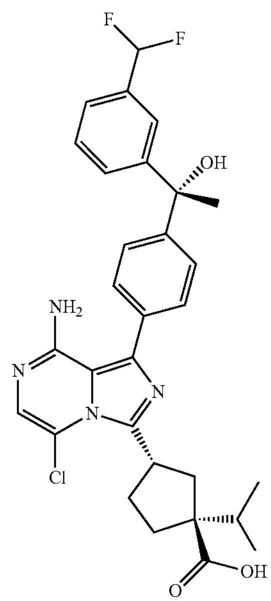 [SMILES: CC(C)[C@]1(C(=O)O)CC[C@H](c2nc(-c3ccc([C@@](C)(O)c4cccc(C(F)F)c4)cc3)c3c(N)ncc(Cl)n23)C1] | (1S,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid | Calc'd 569.2, found 569.1 | 2.428(C) |
| 32 | 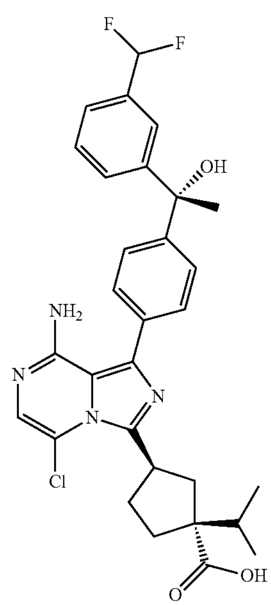 [SMILES: CC(C)[C@@]1(C(=O)O)CC[C@@H](c2nc(-c3ccc([C@@](C)(O)c4cccc(C(F)F)c4)cc3)c3c(N)ncc(Cl)n23)C1] | (1R,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid | Calc'd 569.2, found 569.2 | 2.431(C) |

TABLE 1-continued

| Example Number | Structure | IUPAC Name | Exact Mass [M + H]+ | Retention time (min, method) |
|---|---|---|---|---|
| 33 | 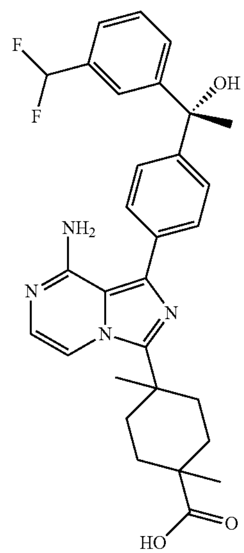 [SMILES: CC1(C(=O)O)CCC(C)(c2nc(-c3ccc([C@@](C)(O)c4cccc(C(F)F)c4)cc3)c3c(N)nccn23)CC1] | 4-[8-amino-1-(4-{(1R)-1-[3-(difluoromethyl)phenyl]-1-hydroxyethyl}phenyl)imidazo[1,5-a]pyrazin-3-yl]-1,4-dimethylcyclohexanecarboxylic acid | Calc'd 535.3, found 535.2 | 2.235(C) |
| 34 | 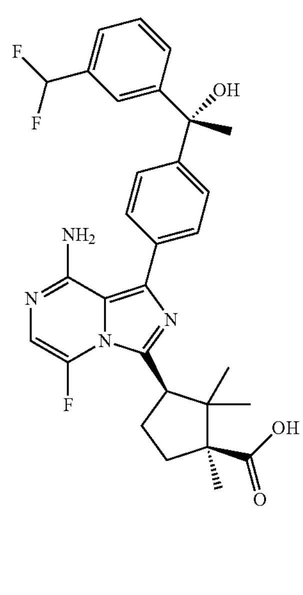 [SMILES: CC1(C)[C@H](c2nc(-c3ccc([C@@](C)(O)c4cccc(C(F)F)c4)cc3)c3c(N)ncc(F)n23)CC[C@]1(C)C(=O)O] | (1S,3R)-3-[8-amino-1-(4-{(1R)-1-[3-(difluoromethyl)phenyl]-1-hydroxyethyl}phenyl)-5-fluoroimidazo[1,5-a]pyrazin-3-yl]-1,2,2-trimethylcyclopentanecarboxylic acid | Calc'd 553.2, found 553.2 | 2.233(C) |

TABLE 1-continued

| Example Number | Structure | IUPAC Name | Exact Mass [M + H]+ | Retention time (min, method) |
|---|---|---|---|---|
| 35 | 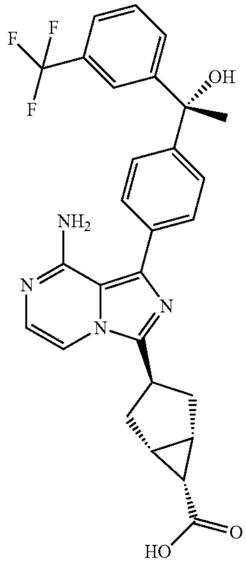 [SMILES: C[C@@](O)(c1ccc(-c2nc([C@@H]3C[C@@H]4[C@H](C3)[C@@H]4C(=O)O)n3ccnc(N)c23)cc1)c1cccc(C(F)(F)F)c1] | (1R,3r,5S,6s)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid | Calc'd 523.2, found 523.2 | 2.218(C) |
| 36 | 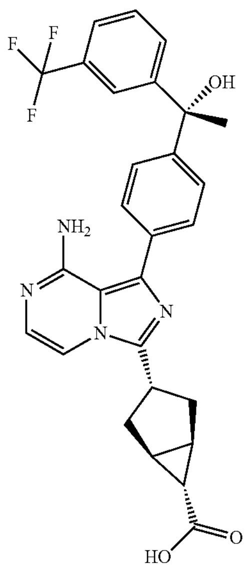 [SMILES: C[C@@](O)(c1ccc(-c2nc([C@@H]3C[C@@H]4[C@H](C3)[C@H]4C(=O)O)n3ccnc(N)c23)cc1)c1cccc(C(F)(F)F)c1] | (1R,3R,5S,6r)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid | Calc'd 523.2, found 523.2 | 2.180(C) |

Biological Activity

The Btk inhibitor compounds of the invention having Formula I inhibit the Btk kinase activity. All compounds of the invention have an IC50 of 10 μM or lower. In another aspect the invention relates to compounds of Formula I which have an IC50 of less than 100 nM. In yet another aspect the invention relates to compounds of Formula I which have an IC50 of less than 10 nM.

The term IC50 means the concentration of the test compound that is required for 50% inhibition of its maximum effect in vitro.

Btk Enzyme Activity Assay Methods

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM MgCl$_2$, 0.01% Brij-35, 1 mM EGTA, 0.05% BSA & 1 mM DTT) containing 5.09 pg/μL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-NH2) (SEQ-.ID.NO.: 1), and 100 μM ATP. The final reaction in each well of 10 μL consists of 50 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate: anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). IC$_{50}$ values were determined by 4 parameter robust fit of TR-FRET ratio values vs. (Log$_{10}$) compound concentrations.

The following Table 3 provides specific IC50 values for all the examples. The IC50 values set forth below were determined according to Assay method described above.

TABLE 2

| Compounds BTK binding potency | |
|---|---|
| Example number | BTK binding IC50 (nM) |
| Example 1 | 39.4 |
| Example 2 | 5.8 |
| Example 3 | 774.8 |
| Example 4 | 1000 |
| Example 5 | 19.0 |

TABLE 2-continued

| Compounds BTK binding potency | |
|---|---|
| Example number | BTK binding IC50 (nM) |
| Example 6 | 52.0 |
| Example 7 | 614.2 |
| Example 8 | 1.1 |
| Example 9 | 7.0 |
| Example 10 | 294.5 |
| Example 11 | 5.0 |
| Example 12 | 17.3 |
| Example 13 | 86.0 |
| Example 14 | 1000 |
| Example 15 | 104 |
| Example 16 | 7.6 |
| Example 17 | 55.1 |
| Example 18 | 178.1 |
| Example 19 | 4.1 |
| Example 20 | 135.6 |
| Example 21 | 56.1 |
| Example 22 | 6.2 |
| Example 23 | 28.7 |
| Example 24 | 6.3 |
| Example 25 | 39.9 |
| Example 26 | 33.5 |
| Example 27 | 0.78 |
| Example 28 | 1.2 |
| Example 29 | 2.8 |
| Example 30 | 32.3 |
| Example 31 | 133 |
| Example 32 | 41.8 |
| Example 33 | 11.4 |
| Example 34 | 2.4 |
| Example 35 | 15.7 |
| Example 36 | 1.1 |

What is claimed is:

1. A compound according to Formula I or a pharmaceutically acceptable salt thereof

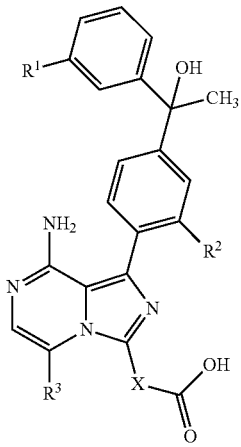
(I)

wherein:
n is 0, 1 or 2;
R¹ is (1-3C)alkyl, optionally substituted with one, two or three halogen;
R₂ is independently selected from the group consisting of methoxy, ethoxy, halogen, and hydroxyl;
R₃ is hydrogen, halogen or C(1-3) alkyl;
X is selected from the group consisting of:
  a) cyclopropyl;
  b) cyclopentyl;
  c) cyclohexyl;
  d) bicyclo[2.2.2]octanyl;
  e) bicyclo[3.2.1]octanyl;
  f) bicyclo[2.2.1]heptanyl;
  g) bicyclo[3.2.2]nonanyl;
  h) bicyclo[3.1.0]hexanyl;
  i) tricyclo[3.2.2.0$^{2,4}$]nonanyl; and
  j) tetrahydropyranyl;
each optionally substituted with one to four R⁴,
  wherein R⁴ is hydrogen, oxo, fluoro or (1-6C)alkyl.

2. A compound of Formula 1a, or a pharmaceutically acceptable salt thereof

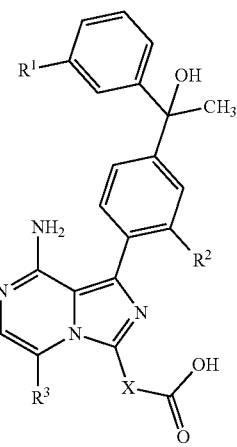
Formula Ia wherein:
R¹ is (1-3C)alkyl, optionally substituted with one, two or three halogen;
R² is hydrogen or (1-3C)alkoxy;
R³ is hydrogen or halogen;
X is selected from the group consisting of:
  a) cyclopropyl;
  b) cyclopentyl;
  c) cyclohexyl;
  d) bicyclo[2.2.2]octanyl;
  e) bicyclo[3.2.1]octanyl;
  f) bicyclo[2.2.1]heptanyl;
  g) bicyclo[3.2.2]nonanyl;
  h) bicyclo[3.1.0]hexanyl;
  i) tricyclo[3.2.2.0$^{2,4}$]nonanyl; and
  j) tetrahydropyranyl;
each optionally substituted with one to four R⁴,
  wherein R⁴ is hydrogen, oxo, fluoro or (1-6C)alkyl.

3. The compound of claim 1, wherein the compound is a compound having Formula Ib

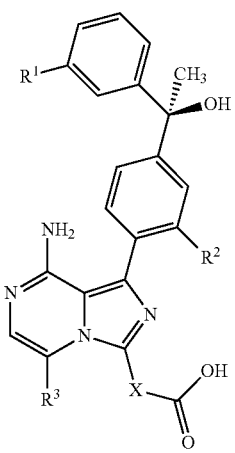
Formula Ib or a pharmaceutically acceptable salt thereof.

4. The compound of claim 1, wherein the compound is a compound having Formula Ic

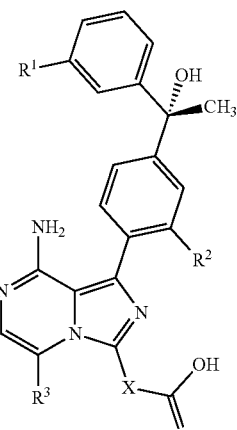
Formula Ic or a pharmaceutically acceptable salt thereof.

5. The compound of claim 1, or a pharmaceutically acceptable salt thereof, wherein R¹ is methyl, difluoromethyl or trifluoromethyl.

6. The compound of claim 1, or a pharmaceutically acceptable salt thereof,
wherein R³ is fluoro or chloro.

7. A compound selected from the group consisting of:
(R)-4-(8-amino-1-(4-(1-hydroxy-1-(3-(trifluoromethyl)phenyl)ethyl)phenyl)imidazo[1,5-a]pyrazin-3-yl)-1,4-dimethylcyclohexanecarboxylic acid;
4-[8-amino-1-(4-{(1S)-1-hydroxy-1-[3-(trifluoromethyl)phenyl]ethyl}phenyl)imidazo[1,5-a]pyrazin-3-yl]bicyclo[2.2.2]octane-1-carboxylic acid;
4-[8-amino-1-(4-{(1R)-1-hydroxy-1-[3-(trifluoromethyl)phenyl]ethyl}phenyl)imidazo[1,5-a]pyrazin-3-yl]bicyclo[2.2.2]octane-1-carboxylic acid;
(1S,3S)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclopentanecarboxylic acid;
(1S,3S)-3-[8-amino-1-(4-{(1R)-1-hydroxy-1-[3-(trifluoromethyl)phenyl]ethyl}phenyl)imidazo[1,5-a]pyrazin-3-yl]-1-(1-methylethyl)cyclopentanecarboxylic acid;
4-[8-amino-1-(4-{(1R)-1-hydroxy-1-[3-(trifluoromethyl)phenyl]ethyl}phenyl)imidazo[1,5-a]pyrazin-3-yl]-2,5-dioxobicyclo[2.2.2]octane-1-carboxylic acid;
1-[8-amino-1-(4-{(1R)-1-hydroxy-1-[3-(trifluoromethyl)phenyl]ethyl}phenyl)imidazo[1,5-a]pyrazin-3-yl]cyclopropanecarboxylic acid;
4-[8-amino-1-(4-{(1R)-1-hydroxy-1-[3-(trifluoromethyl)phenyl]ethyl}phenyl)imidazo[1,5-a]pyrazin-3-yl]bicyclo[2.2.1]heptane-1-carboxylic acid;
5-[8-amino-1-(4-{(1R)-1-hydroxy-1-[3-(trifluoromethyl)phenyl]ethyl}phenyl)imidazo[1,5-a]pyrazin-3-yl]bicyclo[3.2.2]nonane-1-carboxylic acid;
4-[8-amino-1-(4-{(1R)-1-hydroxy-1-[3-(trifluoromethyl)phenyl]ethyl}phenyl)imidazo[1,5-a]pyrazin-3-yl]tetrahydro-2H-pyran-4-carboxylic acid;
(1S,3R)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;
4-[8-amino-1-(4-{(1R)-1-hydroxy-1-[3-(trifluoromethyl)phenyl]ethyl}phenyl)imidazo[1,5-a]pyrazin-3-yl]-2,2,5,5-tetrafluorobicyclo[2.2.2]octane-1-carboxylic acid;
(1R,3S)-3-[8-amino-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;
(1S,3R)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexanecarboxylic acid;
(1R,3S)-3-[8-amino-1-(4-{(1S)-1-hydroxy-1-[3-(trifluoromethyl)phenyl]ethyl}phenyl)imidazo[1,5-a]pyrazin-3-yl]-1-(1-methylethyl)cyclohexanecarboxylic acid;
(1S,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;
(1R,3S)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;
(1S,3R)-3-[8-amino-1-(4-{(1R)-1-hydroxy-1-[3-(trifluoromethyl)phenyl]ethyl}phenyl)imidazo[1,5-a]pyrazin-3-yl]-1,3-dimethylcyclopentanecarboxylic acid;
4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid;
4-(8-amino-1-{2-ethoxy-4-[1-hydroxy-1-(3-methylphenyl)ethyl]phenyl}imidazo[1,5-a]pyrazin-3-yl)bicyclo[2.2.2]octane-1-carboxylic acid;
(1R,2R,5R)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexanecarboxylic acid;
5-[8-amino-1-(4-{(1R)-1-hydroxy-1-[3-(trifluoromethyl)phenyl]ethyl}phenyl)imidazo[1,5-a]pyrazin-3-yl]tricyclo[3.2.2.0~2,4~]nonane-1-carboxylic acid;
(1S,2S,5S)-5-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)cyclohexanecarboxylic acid;
(1S,3R)-3-[8-amino-5-fluoro-1-(4-{(1R)-1-hydroxy-1-[3-(trifluoromethyl)phenyl]ethyl}phenyl)imidazo[1,5-a]pyrazin-3-yl]-1,2,2-trimethylcyclopentanecarboxylic acid;
(3-endo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid;
(3-exo,8-syn)-3-[8-amino-1-(4-{(1R)-1-hydroxy-1-[3-(trifluoromethyl)phenyl]ethyl}phenyl)imidazo[1,5-a]pyrazin-3-yl]bicyclo[3.2.1]octane-8-carboxylic acid;
(1S,3R)-3-[8-amino-1-(4-{(1R)-1-[3-(difluoromethyl)phenyl]-1-hydroxyethyl}phenyl)imidazo[1,5-a]pyrazin-3-yl]-1,2,2-trimethylcyclopentanecarboxylic acid;
(1S,3R)-3-[8-amino-1-(2-ethoxy-4-{(1S)-1-hydroxy-1-[3-(trifluoromethyl)phenyl]ethyl}phenyl)imidazo[1,5-a]pyrazin-3-yl]-1,2,2-trimethylcyclopentanecarboxylic acid;
(1S,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;
(1R,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;
(1S,3S)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;
(1R,3R)-3-[8-amino-5-chloro-1-(4-{(1R)-1-[3-(difluoromethyl)phenyl]-1-hydroxyethyl}phenyl)imidazo[1,5-a]pyrazin-3-yl]-1-(1-methylethyl)cyclopentanecarboxylic acid;
4-[8-amino-1-(4-{(R)-1-[3-(difluoromethyl)phenyl]-1-hydroxyethyl)}phenyl)imidazo[1,5-a]pyrazin-3-yl]-1,4-dimethylcyclohexanecarboxylic acid;
(1S,3R)-3-[8-amino-1-(4-{(1R)-1-[3-(difluoromethyl)phenyl]-1-hydroxyethyl}phenyl)-5-fluoroimidazo[1,5-a]pyrazin-3-yl]-1,2,2-trimethylcyclopentanecarboxylic acid;
(1R,3R,5S,6S)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid; and
(1R,3R,5S,6R)-3-[8-amino-1-(4-{(1R)-1-hydroxy-1-[3-(trifluoromethyl)phenyl]ethyl}phenyl)imidazo[1,5-a]pyrazin-3-yl]bicyclo[3.1.0]hexane-6-carboxylic acid;
or a pharmaceutically acceptable salt thereof.

8. A pharmaceutical composition which comprises the compound of claim 1 or a pharmaceutically acceptable salt thereof and one or more pharmaceutically acceptable carriers.

* * * * *